United States Patent
Drolet et al.

(10) Patent No.: US 11,466,275 B2
(45) Date of Patent: Oct. 11, 2022

(54) NUCLEIC ACID COMPOUNDS FOR BINDING TO COMPLEMENT COMPONENT 3 PROTEIN

(71) Applicant: SomaLogic Operating Co., Inc., Boulder, CO (US)

(72) Inventors: Daniel W. Drolet, Boulder, CO (US); Chi Zhang, Boulder, CO (US); Daniel J. O'Connell, Boulder, CO (US); Shashi Gupta, Louisville, CO (US)

(73) Assignee: Somalogic Operating Co., Inc., Boulder, CO (US)

( * ) Notice: Subject to any disclaimer, the term of this patent is extended or adjusted under 35 U.S.C. 154(b) by 539 days.

(21) Appl. No.: 15/311,714

(22) PCT Filed: May 29, 2015

(86) PCT No.: PCT/US2015/033355
§ 371 (c)(1),
(2) Date: Nov. 16, 2016

(87) PCT Pub. No.: WO2015/184372
PCT Pub. Date: Dec. 3, 2015

(65) Prior Publication Data
US 2017/0166895 A1    Jun. 15, 2017

Related U.S. Application Data

(60) Provisional application No. 62/005,300, filed on May 30, 2014.

(51) Int. Cl.
*C12N 15/11* (2006.01)
*C12N 15/115* (2010.01)

(52) U.S. Cl.
CPC ........ *C12N 15/115* (2013.01); *C12N 2310/16* (2013.01); *C12N 2310/317* (2013.01); *C12N 2310/318* (2013.01); *C12N 2310/33* (2013.01); *C12N 2310/3341* (2013.01); *C12N 2320/10* (2013.01)

(58) Field of Classification Search
CPC .............. C12N 15/115; C12N 2310/16; C12N 15/1048
See application file for complete search history.

(56) References Cited

U.S. PATENT DOCUMENTS

| 8,927,509 B2 | 1/2015 | Shi et al. |
| 2002/0082227 A1 | 6/2002 | Henry |
| 2009/0004667 A1* | 1/2009 | Zichi ............... C12Q 1/6811 435/6.11 |
| 2012/0115752 A1* | 5/2012 | Zichi ............... C12N 15/1048 506/9 |
| 2012/0141382 A1* | 6/2012 | Shi ............... A61K 31/7088 424/9.323 |
| 2012/0231467 A1* | 9/2012 | Ochsner ........... C12N 15/115 435/6.12 |

FOREIGN PATENT DOCUMENTS

| JP | 2002503455 A | 2/2002 |
| JP | 2013523177 A | 6/2013 |
| WO | 97/42317 A1 | 11/1997 |
| WO | 9941271 A1 | 8/1999 |
| WO | 2011130195 A1 | 10/2011 |
| WO | 2013/152024 A1 | 10/2013 |

OTHER PUBLICATIONS

Bokisch et al., Third component of complement (C3): structural properties in relation to functions, PNAS, vol. 72, pp. 1989-1993. (Year: 1975).*
Mallik et al., "Commandeering a biological pathway using aptamer-derived molecular adaptors," Nucleic Acid Research, vol. 38, No. 7, Apr. 1, 2010, e93, 9 pages.
Mallik et al., Supplementary Data, Jan. 6, 2010, 3 pages. (http://nar.oxfordjournals.org/content/suppl/2010/01/06/gkp1207.DC1/nar-02316-met-s-2009-File007.pdf).
Lollo et al., "Beyond antibodies: New affinity reagents to unlock the proteome," Proteomics, vol. 14, No. 6, Mar. 20, 2014, pp. 638-644.
Gupta et al., "Chemically modified DNA aptamers bind Interleukin-6 with high affinity and inhibit signaling by blocking its interaction with Interleukin-6 Receptor," Journal of Biological Chemistry, vol. 289, No. 12, Mar. 21, 2014, pp. 8706-8719.
Ochsner et al., "Systematic selection of modified aptamer pairs for diagnostic sandwich assays," BioTechniques, Jan. 1, 2014, pp. 125-133, http://www.ncbi.nlm.nih.gov/pubmed/24641476.
Davies et al., "Unique motifs and hydrophobic interactions shape the binding of modified DNA ligands to protein targets," Proceedings of the National Academy of Sciences, vol. 109, No. 49, Nov. 8, 2012, p. 19971-19976.
International Search Report issued in corresponding PCT Application No. PCT/US/2015/033355, filed May 29, 2015, dated Sep. 2, 2015, 4 pages.

* cited by examiner

Primary Examiner — Dana H Shin
(74) Attorney, Agent, or Firm — McNeill Baur PLLC

(57) ABSTRACT

Described herein are aptamers capable of binding to human complement component 3 (C3) protein; compositions comprising a C3 binding aptamer with a C3-Protein; and methods of making and using the same.

24 Claims, 14 Drawing Sheets
Specification includes a Sequence Listing.

| Abbreviation | 5-dU Modification | Chemical Structure |
|---|---|---|
| Bn | benzylmethyl | 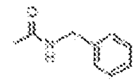 |
| Nap | 1-naphthylmethyl | 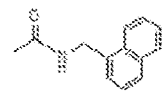 |
| PE | 2-phenylethyl | 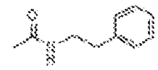 |
| PP | 3-phenylpropyl | 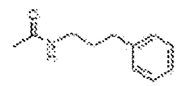 |
| Ib | iso-butyl | 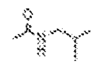 |
| FBn | 4-fluorobenzylmethyl | 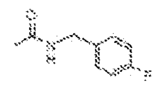 |
| 2Nap | 2-naphthylmethyl | 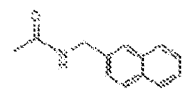 |
| Tyr | tyrosyl | 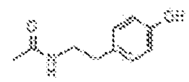 |
| NE | 1-naphthylethyl | 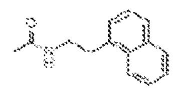 |
| MBn | 3,4-methylenedioxy benzyl | 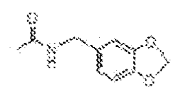 |
| MOE | morpholinoethyl | 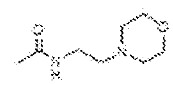 |
| BF | 3-benzofuranylethyl | 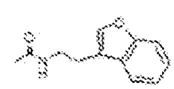 |
| BT | 3-benzothiophenylethyl | 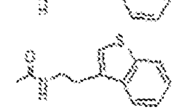 |
| 2NE | 2-naphthyl-2-ethyl | 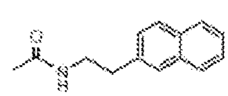 |
| Trp | 3-indole-2-ethyl |  | wherein

R'''' is selected from the group consisting of a branched or linear lower alkyl (C1-C20); halogen (F, Cl, Br, I); nitrile (CN); boronic acid ($BO_2H_2$); carboxylic acid (COOH); carboxylic acid ester (COOR''); primary amide ($CONH_2$); secondary amide (CONHR''); tertiary amide (CONR''R'''); sulfonamide ($SO_2NH_2$); N-alkylsulfonamide (SONHR'').

wherein

R'', R''' are independently selected from a group consisting of a branched or linear lower alkyl (C1-C2)); phenyl ($C_6H_5$); an R'''' substituted phenyl ring (R''''$C_6H_4$); wherein R'''' is defined above; a carboxylic acid (COOH); a carboxylic acid ester (COOR''''); wherein R'''' is a branched or linear lower alkyl (C1-C20); and cycloalkyl; wherein R'' = R''' = $(CH_2)_n$; wherein n = 2-10.

NUCLEIC ACID COMPOUNDS FOR BINDING TO COMPLEMENT COMPONENT 3 PROTEIN

This application is a national phase entry pursuant to 35 U.S.C. § 371 of International Application No. PCT/US2015/033355, filed May 29, 2015, which claims the benefit of U.S. Provisional Application No. 62/005,300, filed May 30, 2014, each of which is incorporated by reference herein in its entirety for any purpose.

FIELD

The present disclosure relates generally to the field of nucleic acids, and more specifically, to aptamers capable of binding to human complement component 3 (C3 or C3-Protein), compositions comprising a C3 binding aptamer and C3, and methods of inhibiting the biological function of C3 and methods of detecting C3 using such aptamers.

BACKGROUND

The complement system comprises a group of interacting proteins that includes soluble proteins found in blood and other bodily fluids as well as cell-bound proteins (Makrides, *Pharmacological Reviews* 1998, 50(1): 59-88). This system plays a major role in innate immunity which is required for host defense against pathogens and mediates pathogen cell lysis, immune cell chemotaxis, and phagocytosis (Janeway et al. Immunobiology: The Immune System in Health and Disease. 5th edition. New York: Garland Science; 2001).

Complement component 3 (C3) protein (a glycoprotein found in blood) is a member of this system and plays a central role in the pathway (Lambris, *Immunology Today* 1988, 9(12): 387-393). The human complement component 3 (C3) genes is located on the short arm of chromosome 19 (Lusis et al., *Proc. Natl. Acad. Sci. USA*, 1986, 83: 3929-3933) and is transcribed, processed and translated into pro-C3. Pro-C3 undergoes site specific endo-proteolytic cleavage upon secretion to yield circulating C3. C3 circulates as a protein containing two subunits (alpha chain 115 kDa and beta chain 75 kDa) linked by a disulfide bond. The concentration of C3-Protein in normal human serum is approximately 1.15 mg/mL (Kasperska-Zajac et al., *J. Inflammation* 2013, 10:22; doi: 10.1186/1476-9255-10-22).

Following its activation, the covalent binding of C3-Protein to surfaces initiates many effects of the complement system. Activation can be accomplished by the site-specific proteolysis of soluble C3-Protein into two proteins termed C3a and C3b. C3b covalently binds to surfaces where it acts to target particles for phagocytosis (opsonization) or initiates the terminal complement pathway leading to pathogen cell lysis. C3a is a so called anaphylatoxin, a mediator of diverse physiological functions such as smooth muscle cell contraction, vascular permeability, mast cell degranulation and chemotaxis of immune cells. Inhibitors of C3 that prevent the site-specific proteolytic activating event are desirable as they may prevent the biological functions of both C3a and C3b as well as the activation of the terminal complement pathway.

The complement system is generally tightly regulated in order to prevent tissue damage to the host (Thurman et al., *J. Immunol.* 2006, 176: 1305-1310). However, when deregulated, as can happen when one or more control mechanisms fail or by atypical immune system modulation, the resulting excess complement activation can lead to pathophysiology. For example, in both atypical hemolytic-uremic syndrome and age-related macular degeneration, alterations in the complement control protein factor H are implicated to lead to an increase in C3-convertase activity and thus to excess complement activation (Ferreira et al., *Mol. Immunol.* 2010, 47(13): 2187-2197). The over-activation of complement can then attack the host's own cells resulting in the tissue damage observed in these diseases. The complement system may also contribute to the tissue damage caused by many inflammatory disorders and ischemia/reperfusion injury. Therefore therapeutic agents that can inhibit the complement system, including those that inhibit the activity of C3, may prove beneficial. The present disclosure meets such needs by providing aptamers that can inhibit the bioactivity of human C3-Protein and prevent the release of C3a.

Determining the concentration of C3 in bodily fluids is useful as diagnostic tests for several diseases and conditions including, but not limited to, the diagnosis of acute inflammatory conditions, microbial infections, congenital C3 deficiency, acute glomerulonephritis, systemic lupus erythematosus, membranoproliferative glomerulonephritis and immune complex diseases (Nilsson et al., *Clin. Dev. Immunol.* 2012, 2012: Article ID 962702, 11 pages). At present, antibodies are the most common tool for detecting the C3. However, they suffer from several disadvantages, including stability (both tolerance of varying temperature and pH conditions, and a lack of recoverability from non-ideal conditions), which equates to a limited shelf-life, special storage requirements (e.g., cooling), aggregation and relatively costly production. The present disclosure addresses the problems encountered with antibodies by providing aptamers having binding specificity to human C3-Protein.

SUMMARY

The present disclosure describes aptamers capable of binding to human complement component 3 (C3) protein; these aptamers are shown to be inhibitors of the complement-mediated activation of C3 and therefore may be useful as diagnostic and therapeutic agents. Pharmaceutical compositions comprising C3-protein binding aptamers; and methods of making and using the same are described.

In some embodiments, an aptamer that binds C3 protein is provided. In some embodiments, an aptamer that binds C3 protein comprises the sequence 5'-KPGRMPDVD$_n$L-PAWPSVGPAYRPP-3' (SEQ ID NO: 152), wherein K is a C-5 modified pyrimidine, C, U, T, G, or a 3-carbon spacer; each P is independently, and for each occurrence, a C-5 modified pyrimidine; R is A or G; M is C, U, T, a C-5 modified pyrimidine, or a 3-carbon spacer; each D is independently, and for each occurrence, an A, C, or a 3-carbon spacer; each V is independently, and for each occurrence, an A, G, C, or a 3-carbon spacer; L is A, U, T or a C-5 modified pyrimidine; W is G or a 3-carbon spacer; S is C or a 3-carbon spacer; Y is C, U, or T; and n is 0 or 1. In some embodiments, the aptamer comprises the sequence 5'-KPGRMPDVD$_n$L-PAWPSVGPAYRPPM-3' (SEQ ID NO: 153), wherein each M is independently, and for each occurrence, C, U, T, a C-5 modified pyrimidine, or a 3-carbon spacer.

In some embodiments, an aptamer that binds C3 protein is provided. In some embodiments, an aptamer that binds C3 protein comprises the sequence 5'-KPGRMPDVD$_n$L-PAWPSVGPACGPP-3' (SEQ ID NO: 131), wherein K is a C-5 modified pyrimidine, C, U, T, G, or a 3-carbon spacer; each P is independently, and for each occurrence, a C-5 modified pyrimidine; R is A or G; M is C, U, T, a C-5 modified pyrimidine, or a 3-carbon spacer; each D is independently, and for each occurrence, an A, C, or a 3-carbon spacer; each V is independently, and for each occurrence, an A, G, C, or a 3-carbon spacer; L is A, U, T or a C-5 modified pyrimidine; W is G or a 3-carbon spacer; S is C or a 3-carbon spacer; and n is 0 or 1. In some embodiments, the aptamer comprises the sequence 5'-KPGRMPDVD$_n$L-PAWPSVGPACGPPM-3' (SEQ ID NO: 135), wherein each M is independently, and for each occurrence, C, U, T, a C-5 modified pyrimidine, or a 3-carbon spacer.

In some embodiments, an aptamer that binds C3 protein comprises the sequence 5'-KPGRMPXPAWPSVGPAYRPP-3' (SEQ ID NO: 154), wherein K is a C-5 modified pyrimidine, C, U, T, G, or a 3-carbon spacer; each P is independently, and for each occurrence, a C-5 modified pyrimidine; R is A or G; M is C, U, T a C-5 modified pyrimidine, or a 3-carbon spacer; V is A, G, C, or a 3-carbon spacer; W is G or a 3-carbon spacer; S is C or a 3-carbon spacer; Y is C, U, or T; and X is a linker selected from a substituted or unsubstituted $C_2$-$C_{20}$ linker, an alkylene glycol, and a polyalkylene glycol. In some embodiments, the aptamer comprises the sequence 5'-KPGRMPXPAWPSVGPAYRPPM-3' (SEQ ID NO: 155), wherein each M is independently, and for each occurrence, C, U, T, a C-5 modified pyrimidine, or a 3-carbon spacer.

In some embodiments, an aptamer that binds C3 protein comprises the sequence 5'-KPGRMPX-PAWPSVGPACGPP-3' (SEQ ID NO: 136), wherein K is a C-5 modified pyrimidine, C, U, T, G, or a 3-carbon spacer; each P is independently, and for each occurrence, a C-5 modified pyrimidine; R is A or G; M is C, U, T a C-5 modified pyrimidine, or a 3-carbon spacer; V is A, G, C, or a 3-carbon spacer; W is G or a 3-carbon spacer; S is C or a 3-carbon spacer; and X is a linker selected from a substituted or unsubstituted $C_2$-$C_{20}$ linker, an alkylene glycol, and a polyalkylene glycol. In some embodiments, the aptamer comprises the sequence 5'-KPGRMPX-PAWPSVGPACGPPM-3' (SEQ ID NO: 137), wherein each M is independently, and for each occurrence, C, U, T, a C-5 modified pyrimidine, or a 3-carbon spacer.

In any of the embodiments described above, K may be a C-5 modified pyrimidine, C or G; each M may be independently, and for each occurrence, C or a C-5 modified pyrimidine; and/or L may be A or C-5 modified pyrimidine.

In some embodiments, an aptamer that binds C3 protein comprises the sequence 5'-PAWPSVGPAYRPP-3' (SEQ ID NO: 156), wherein each P is independently, and for each occurrence, a C-5 modified pyrimidine; W is G or a 3-carbon spacer; S is C or a 3-carbon spacer; V is A, G or C; Y is C, U, or T; and R is G or A.

In some embodiments, an aptamer that binds C3 protein comprises the sequence 5'-PAWPSVGPACGPP-3' (SEQ ID NO: 134), wherein each P is independently, and for each occurrence, a C-5 modified pyrimidine; W is G or a 3-carbon spacer; S is C or a 3-carbon spacer; and V is A, G or C.

In some embodiments, an aptamer that binds C3 protein comprises a sequence that is at least 80%, at least 85%, at least 90%, at least 95%, at least 97%, at least 99%, or 100% identical to a sequence selected from SEQ ID NOs: 4 to 130 and 138 to 151, wherein each P is independently, and for each occurrence, a C-5 modified pyrimidine. In some embodiments, an aptamer that binds C3 protein comprises a sequence that is at least 80%, at least 85%, at least 90%, at least 95%, at least 97%, at least 99%, or 100% identical to a sequence selected from SEQ ID NOs: 4 to 28, 32 to 34, 37 to 75, 78 to 118, 121 to 130, and 139 to 151, wherein each P is independently, and for each occurrence, a C-5 modified pyrimidine.

In some embodiments, an aptamer that binds C3 protein comprises a first region and a second region, wherein the first region comprises the sequence 5'-PAGPC-3' (SEQ ID NO: 132) and the second region comprises the sequence 5'-GPAYRPP-3' (SEQ ID NO: 157), wherein each P is independently, and for each occurrence, a C-5 modified pyrimidine; Y is C, U, or T; and R is G or A.

In some embodiments, an aptamer that binds C3 protein comprises a first region and a second region, wherein the first region comprises the sequence 5'-PAGPC-3' (SEQ ID NO: 132) and the second region comprises the sequence 5'-GPACGPP-3' (SEQ ID NO: 133), wherein each P is independently, and for each occurrence, a C-5 modified pyrimidine.

In some embodiments, the 3'-end of the first region is covalently linked to the 5'-end of the second region. In some embodiments, the first region and the second region are covalently linked by at least one, two, three, four or five linkers, wherein each linkers is independently selected from a nucleotide, a substituted or unsubstituted $C_2$-$C_{20}$ linker, an alkylene glycol, and a polyalkylene glycol. In some embodiments, each linker is independently selected from a nucleotide, a 3-carbon spacer, and a hexaethylene glycol.

In some embodiments, an aptamer that binds C3 protein comprises the sequence 5'-PAGPC-3' (SEQ ID NO: 132), wherein each P is independently, and for each occurrence, a C-5 modified pyrimidine. In some embodiments, an aptamer that binds C3 protein comprises the sequence 5'-GPACGPP-3' (SEQ ID NO: 133), wherein each P is independently, and for each occurrence, a C-5 modified pyrimidine. In some embodiments, an aptamer that binds C3 protein comprises the sequence 5'-GPAYRPP-3' (SEQ ID NO: 157), wherein each P is independently, and for each occurrence, a C-5 modified pyrimidine; Y is C, U, or T; and R is G or A.

In some embodiments, an aptamer that binds C3 protein comprises the sequence of SEQ ID NO: 125, wherein each P is independently, and for each occurrence, a C-5 modified pyrimidine.

In some embodiments of the aptamers described herein, each C-5 modified pyrimidine is independently selected from: 5-(N-benzylcarboxamide)-2'-deoxyuridine (BndU), 5-(N-benzylcarboxamide)-2'-O-methyluridine, 5-(N-benzylcarboxamide)-2'-fluorouridine, 5-(N-phenethylcarboxamide)-2'-deoxyuridine (PEdU), 5-(N-thiophenylmethylcarboxamide)-2'-deoxyuridine (ThdU), 5-(N-isobutylcarboxamide)-2'-deoxyuridine (iBudU), 5-(N-tyrosylcarboxamide)-2'-deoxyuridine (TyrdU), 5-(N-3,4-methylenedioxybenzylcarboxamide)-2'-deoxyuridine (MBndU), 5-(N-4-fluorobenzylcarboxamide)-2'-deoxyuridine (FBndU), 5-(N-3-phenylpropylcarboxamide)-2'-deoxyuridine (PPdU), 5-(N-imidizolylethylcarboxamide)-2'-deoxyuridine (ImdU), 5-(N-isobutylcarboxamide)-2'-O-methyluridine, 5-(N-isobutylcarboxamide)-2'-fluorouridine, 5-(N-tryptaminocarboxamide)-2'-deoxyuridine (TrpdU), 5-(N—R-threoninylcarboxamide)-2'-deoxyuridine (ThrdU), 5-(N-tryptaminocarboxamide)-2'-O-methyluridine, 5-(N-tryptaminocarboxamide)-2'-fluorouridine, 5-(N-[1-(3-trimethylamonium) propyl]carboxamide)-2'-deoxyuridine chloride, 5-(N-naphthylmethylcarboxamide)-2'-deoxyuridine (NapdU), 5-(N-naphthylmethylcarboxamide)-2'-O-methyluridine, 5-(N-naphthylmethylcarboxamide)-2'-fluorouridine, 5-(N-[1-(2,3-dihydroxypropyl)]carboxamide)-2'-deoxyuridine), 5-(N-2-naphthylmethylcarboxamide)-2'-deoxyuridine (2NapdU), 5-(N-2-naphthylmethylcarboxamide)-2'-O-methyluridine, 5-(N-2-naphthylmethylcarboxamide)-2'-fluorouridine, 5-(N-1-naphthylethylcarboxamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine. In some embodiments, each C-5 modified pyrimidine is independently selected from: 5-(N-1-naphthylmethylcarboxyamide)-2'-deoxyuridine (NapdU), 5-(N-1-naphthylmethylcarboxyamide)-2'-O-methyluridine, 5-(N-1-naphthylmethylcarboxyamide)-2'-fluorouridine, 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine. In some embodiments, each C-5 modified pyrimidine is 5-(N-naphthylmethylcarboxyamide)-2'-deoxyuridine (NapdU).

In any of the embodiments described herein, the aptamer may comprise at least one 2'-O-methyl modified nucleotide.

In any of the embodiments described herein, the aptamer may be from about 24 to about 100 nucleotides in length, or from about 30 to about 60 nucleotides in length, or from about 28 to about 60 nucleotides in length, or from about 40 to about 50 nucleotides in length, or about 28 nucleotides in length. In any of the embodiments described herein, the aptamer may be 24 to 100 nucleotides in length, or 30 to 60 nucleotides in length, or 28 to 60 nucleotides in length, or 28 to 50 nucleotides in length, or 28 to 40 nucleotides in length, or 40 to 50 nucleotides in length, or 28 to 32 nucleotides in length.

In some embodiments, an aptamer described herein binds C3 protein and inhibits cleavage of C3 protein. In some embodiments, the C3 protein is human C3 protein.

In some embodiments, a composition is provided, comprising an aptamer described herein and a complement component 3 (C3) protein. In some such embodiments, the complement component 3 (C3) protein is a human complement component 3 (C3) protein.

In some embodiments, methods for inhibiting the cleavage of a complement component 3 (C3) protein are provided, comprising contacting a C3 protein with an aptamer described herein. In some embodiments, the C3 protein is in a sample in vitro. In some embodiments, the C3 protein is in a subject.

In some embodiments, methods for inhibiting at least one activity of the complement system are provided, comprising contacting components of the complement system with an aptamer described herein. In some embodiments, the components of the complement system are in a sample in vitro. In some embodiments, the components of the complement system are in a subject.

In some embodiments, methods for inhibiting cleavage of a complement component 3 (C3) protein in a subject are provided, comprising administering to the subject an effective amount of an aptamer described herein.

In some embodiments, methods for inhibiting at least one activity of the complement system in a subject are provided, comprising administering to the subject an effective amount of an aptamer described herein.

In some embodiments, methods of treating age-related macular degeneration, an autoimmune disease, a hematological disorder, an infectious disease, sepsis, an inflammatory disease, or a neurodegenerative disease are provided, comprising administering to a subject an effective amount of an aptamer described herein. In some embodiments, the autoimmune disease is selected from lupus erythematosus and rheumatoid arthritis. In some embodiments, the hematological disorder is paroxysmal nocturnal hemoglobinuria. In some embodiments, the inflammatory disease is selected from ischemia/reperfusion injury, arthritis, and nephritis. In some embodiments, the neurodegenerative disease is selected from Huntington's disease and Parkinson's disease.

In some embodiments, use of an aptamer described herein for inhibiting cleavage of C3 protein is provided. In some embodiments, use of an aptamer described herein for inhibiting at least one activity of the complement system is provided. In some embodiments, use of an aptamer described herein for treating age-related macular degeneration, an autoimmune disease, a hematological disorder, an infectious disease, sepsis, an inflammatory disease, or a neurodegenerative disease is provided. In some embodiments, the autoimmune disease is selected from lupus erythematosus and rheumatoid arthritis. In some embodiments, the hematological disorder is paroxysmal nocturnal hemoglobinuria. In some embodiments, the inflammatory disease is selected from ischemia/reperfusion injury, arthritis, and nephritis. In some embodiments, the neurodegenerative disease is selected from Huntington's disease and Parkinson's disease.

In some embodiments, methods for selecting an aptamer having binding affinity for a C3 protein are provided. In some embodiments, a method comprises: (a) contacting a candidate mixture with a C3 protein, wherein the candidate mixture comprises modified nucleic acids in which one, several or all pyrimidines in at least one, or each, nucleic acid of the candidate mixture comprises a C-5 modified pyrimidine; (b) exposing the candidate mixture to a slow off-rate enrichment process, wherein nucleic acids having a slow rate of dissociation from the target molecule relative to other nucleic acids in the candidate mixture bind the C3 protein, forming nucleic acid-target molecule complexes; (c) partitioning slow off-rate nucleic acids from the candidate mixture; and (d) amplifying the slow off-rate nucleic acids to yield a mixture of nucleic acids enriched in nucleic acid sequences that are capable of binding to the C3 protein with a slow off-rate, whereby a slow off-rate aptamer to the C3 protein molecule is selected. In some embodiments, the candidate mixture comprises nucleic acids comprising the sequence 5'-PAGPC-3' (SEQ ID NO: 132), wherein each P is independently, and for each occurrence, a C-5 modified pyrimidine. In some embodiments, the candidate mixture comprises nucleic acids comprising the sequence 5'-GPACGPP-3' (SEQ ID NO: 133), wherein each P is independently, and for each occurrence, a C-5 modified pyrimidine. In some embodiments, the candidate mixture comprises nucleic acids comprising the sequence 5'-GPAY-RPP-3' (SEQ ID NO: 157), wherein each P is independently, and for each occurrence, a C-5 modified pyrimidine; Y is C, U, or T; and R is G or A. In some embodiments, each nucleic acid is, independently, from about 24 to about 100 nucleotides in length, or from about 30 to about 60 nucleotides in length, or from about 28 to about 60 nucleotides in length, or from about 40 to about 50 nucleotides in length, or about 28 nucleotides in length. In some embodiments, each C-5 modified pyrimidine is independently selected from: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-tyrosylcarboxyamide)-2'-deoxyuridine (TyrdU), 5-(N-3,4-methylenedioxybenzylcarboxyamide)-2'-deoxyuridine (MBndU), 5-(N-4-fluorobenzylcarboxyamide)-2'-deoxyuridine (FBndU), 5-(N-3-phenylpropylcarboxyamide)-2'-deoxyuridine (PPdU), 5-(N-imidizolylethylcarboxyamide)-2'-deoxyuridine (ImdU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N—R-threoninylcarboxyamide)-2'-deoxyuridine (ThrdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine), 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine. In some embodiments, each C-5 modified pyrimidine is independently selected from: 5-(N-1-naphthylmethylcarboxyamide)-2'-deoxyuridine (NapdU), 5-(N-1-naphthylmethylcarboxyamide)-2'-O-methyluridine, 5-(N-1-naphthylmethylcarboxyamide)-2'-fluorouridine, 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine. In some embodiments, each C-5 modified pyrimidine is 5-(N-naphthylmethylcarboxyamide)-2'-deoxyuridine (NapdU). In some embodiments, a plurality of nucleic acids in the mixture comprise at least one 2'-O-methyl modified nucleotide. In some embodiments, a plurality of nucleic acids in the mixture comprise a C3-spacer, HEG linker or PEG linker. In some embodiments, the C3 protein is a human C3 protein.

The foregoing and other objects, features, and advantages of the invention will become more apparent from the following detailed description, which proceeds with reference to the accompanying figures.

BRIEF DESCRIPTION OF THE DRAWINGS

FIGS. 1A and 1B. (A) The twenty-five independently derived and active pattern 1 aptamer sequences are shown. The number of times an identical or equivalent (≤5 nucleotide differences) aptamer was sequenced from the Round 9 pool of over 40,000 sequences is shown. The nucleotides identical to the most frequently sequenced aptamer of pattern 1, 8491-3_3 are highlighted within each sequence. (B) Nucleotide position and consensus sequence (SEQ ID NO: 135) for aptamer pattern 1 is shown in the top two rows. Rows A, C, G and P (where A is adenine, C is cytosine and G is guanine, P is a NapdU) indicate the frequency at which these nucleotides are observed in aptamer pattern 1 at each of the 23 nucleotide positions that define the consensus sequence. In the consensus sequence, multiple nucleotide consensuses are indicated with the following single letter code. R=A or G; M=P or C, K=C, G or P; L=A or P; D=C or A; V=A, C or G. A single base insertion is allowed between positions 8 and 9. This insertion occurred with a frequency of 0.16. The "no insertion" frequency was 0.84.

FIG. 11 provides the definitions for R', R", and R'''.

DETAILED DESCRIPTION

I. Terms and Methods

Figure 2:
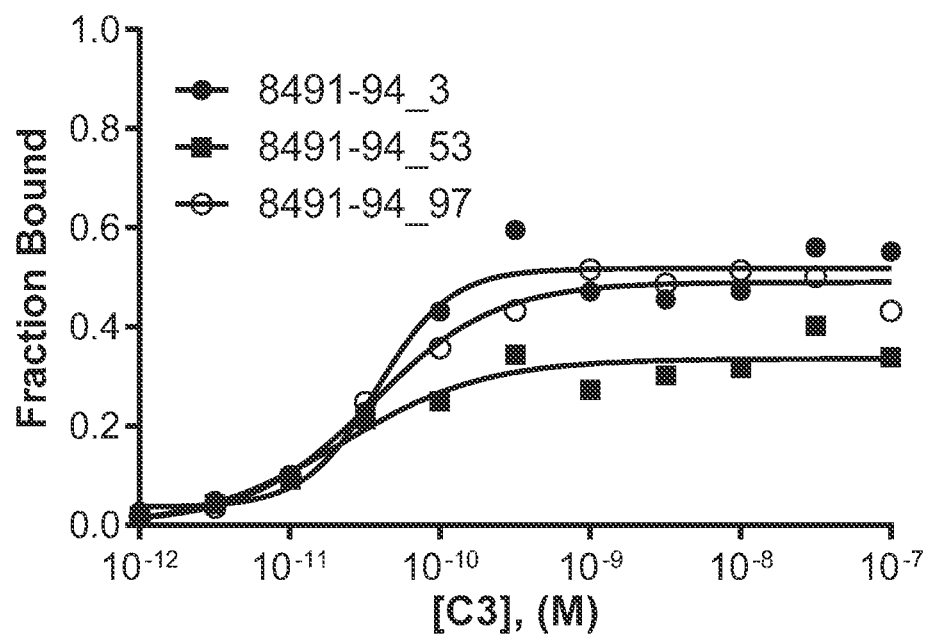
FIG. 2. Shown is a graphical representation of the fraction of bound DNA molecules (y-axis) plotted as a function of protein concentration (x-axis). Human C3-Protein concentration ranged from $1\times10^{-7}$ M to $1\times10^{-12}$ M, and the equilibrium binding constants ($K_d$) was calculated using $y=(\text{maximum.}-\text{minimum})(P_t)/(K_d+P_t)+\text{minimum}$. Aptamers 8491-94_3 (SEQ ID NO: 5), 8491-94_53 (SEQ ID NO: 58), and 8491-94_97 (SEQ ID NO: 125) bound to C3 with a $K_d$ of $3.13\times10^{-11}$ M, $3.34\times10^{-11}$ M and $5.49\times10^{-11}$ M, respectively.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Aptamer: The term aptamer, as used herein, refers to a non-naturally occurring nucleic acid that has a desirable action on a target molecule. Desirable actions include, but are not limited to, binding of the target, inhibiting the activity of the target, enhancing the activity of the target, altering the binding properties of the target (such as, for example, increasing or decreasing affinity of the target for a ligand, receptor, cofactor, etc.), inhibiting processing of the target (such as inhibiting protease cleavage of a protein target), enhancing processing of the target (such as increasing the rate or extent of protease cleavage of a protein target), and inhibiting or facilitating the reaction between the target and another molecule. An aptamer may also be referred to as a "nucleic acid ligand." In some embodiments, an aptamer is a SOMAmer. As used herein, the term "aptamer" includes aptamers and pharmaceutically acceptable salts thereof, unless specifically indicated otherwise.

In some embodiments, an aptamer specifically binds a target molecule, wherein the target molecule is a three dimensional chemical structure other than a polynucleotide that binds to the aptamer through a mechanism which is independent of Watson/Crick base pairing or triple helix formation, and wherein the aptamer is not a nucleic acid having the known physiological function of being bound by the target molecule. In some embodiments, aptamers to a given target include nucleic acids that are identified from a candidate mixture of nucleic acids, by a method comprising: (a) contacting the candidate mixture with the target, wherein nucleic acids having an increased affinity to the target relative to other nucleic acids in the candidate mixture can be partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids, whereby aptamers to the target molecule are identified. It is recognized that affinity interactions are a matter of degree; however, in this context, an aptamer that "specifically binds" its target means that the aptamer binds to its target with a much higher degree of affinity than it binds to other, non-target, components in a mixture or sample. An "aptamer" or "nucleic acid ligand" is a set of copies of one type or species of nucleic acid molecule that has a particular nucleotide sequence. An aptamer can include any suitable number of nucleotides. "Aptamers" refer to more than one such set of molecules. Different aptamers can have either the same or different numbers of nucleotides. Aptamers may comprise DNA, RNA, both DNA and RNA, and modified versions of either or both, and may be single stranded, double stranded, or contain double stranded or triple stranded regions, or any other three-dimensional structures.

Bioactivity: The term bioactivity, as used herein, refers to one or more intercellular, intracellular or extracellular process (e.g., cell-cell binding, ligand-receptor binding, cell signaling, etc.) which can impact physiological or pathophysiological processes.

C-5 Modified Pyrimidine: C-5 modified pyrimidine, as used herein, refers to a pyrimidine with a modification at the C-5 position. Examples of a C-5 modified pyrimidine include those described in U.S. Pat. Nos. 5,719,273 and 5,945,527. Certain nonlimiting examples of C-5 modified pyrimidines are provided herein.

C3 Aptamer: "C3 aptamer", as used herein, refers to an aptamer that is capable of binding to a C3-Protein.

C3-Spacer: A "C3-spacer" or "3 carbon spacer" or "C3 substitution", as used herein, refers to a linker comprising at least three carbons designed to span the same distance as a nucleotide, but lacking a ribose sugar and purine or pyrimidine base moiety. In some embodiments, a C3 spacer has the structure $(CH_2)_3$, wherein it is covalently linked to adjacent nucleotides or other moieties through phosphodiester or phosphorothioate bonds.

Components of the Complement System: Components of the complement system, as used herein, refers to one or more of the proteins that function in the complement pathway and are capable of initiating, activating, promoting and/or modulating the complement pathway. Thus, in the context of a reagent (e.g., aptamer) that is capable of inhibiting or substantially inhibiting the complement system as a result of contacting a sample comprising the components of the complement system, the reagent may, by way of example, interact, bind and/or interfere with the activity, binding and/or function of one or more of the proteins in the complement pathway.

Inhibit: The term inhibit, as used herein, means to reduce the biological activity of a target to an extent that the target has lost a measurable amount of activity; or to reduce the stability and/or reduce the activity of a target to an extent that the target no longer has measurable activity. In some embodiments, such inhibition may occur by affecting the interaction of the target with another moiety and/or the affecting processing of the target. As described herein, the target that may be inhibited is C3.

Modified: As used herein, the terms "modify", "modified", "modification", and any variations thereof, when used in reference to an oligonucleotide, means that the oligonucleotide comprises at least one non-natural moiety, such as at least one non-natural sugar moiety, at least one non-natural internucleoside linkage, at least one non-natural nucleotide base moiety, and/or at least one moiety that does not naturally occur in oligonucleotides (such as, for example, a 3 carbon spacer or a hexaethylene glycol (HEG)). In some embodiments, at least one of the four constituent nucleotide bases (i.e., A, G, T/U, and C) of the oligonucleotide is a modified nucleotide. In some such embodiments, the modified nucleotide comprises a base moiety that is more hydrophobic than the naturally-occurring base. In some embodiments, the modified nucleotide confers nuclease resistance to the oligonucleotide. In some embodiments, when an aptamer comprises one or more modified nucleotides that comprise hydrophobic base moieties, the aptamer binds to its target, such as a protein, through predominantly hydrophobic interactions. In some embodiments, such hydrophobic interactions result in high binding efficiency and stable co-crystal complexes. A pyrimidine with a substitution at the C-5 position is an example of a modified nucleotide. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers, in some embodiments, ranging from about 10 to about 80 kDa, PEG polymers, in some embodiments, ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Polynucleotides can also contain analogous forms of ribose or deoxyribose sugars that are generally known in the art, including 2'-O-methyl-, 2'-O-allyl, 2'-fluoro- or 2'-azidoribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

Modulate: As used herein, "modulate" means to alter, either by increasing or decreasing, the level, stability, processing, and/or activity of a target.

Nucleic Acid: As used herein, "nucleic acid," "oligonucleotide," and "polynucleotide" are used interchangeably to refer to a polymer of nucleotides and include DNA, RNA, DNA/RNA hybrids and modified versions of such entities. The terms "polynucleotide," "oligonucleotide," and "nucleic acid" include double- or single-stranded molecules as well as triple-helical molecules. The term nucleic acid includes aptamers, but is not limited thereto (i.e., the term includes other polymers of nucleotides).

Nuclease: As used herein, the term "nuclease" refers to an enzyme capable of cleaving the phosphodiester bond between nucleotide subunits of an oligonucleotide. As used herein, the term "endonuclease" refers to an enzyme that cleaves phosphodiester bond(s) at a site internal to the oligonucleotide. As used herein, the term "exonuclease" refers to an enzyme which cleaves phosphodiester bond(s) linking the end nucleotides of an oligonucleotide. Biological fluids typically contain a mixture of both endonucleases and exonucleases.

Nuclease Resistant: As used herein, the terms "nuclease resistant" and "nuclease resistance" refer to the reduced ability of an oligonucleotide to serve as a substrate for an endo- or exonuclease, such that, when contacted with such an enzyme, the oligonucleotide is either not degraded or is degraded more slowly or to a lesser extent than a control oligonucleotide of similar length and sequence but lacking one or more modifications of the oligonucleotide whose nuclease resistance is being measured.

Nucleotide: As used herein, the term "nucleotide" refers to a ribonucleotide or a deoxyribonucleotide, or a modified form thereof. Nucleotides include species that include purines (e.g., adenine, hypoxanthine, guanine, and the like) as well as pyrimidines (e.g., cytosine, uracil, thymine, and the like). When a base is indicated as "A", "C", "G", "U", or "T", it is intended to encompass both ribonucleotides and deoxyribonucleotides, and modified forms thereof.

Pharmaceutically Acceptable: Pharmaceutically acceptable, as used herein, means approved by a regulatory agency of a federal or a state government or listed in the U.S. Pharmacopoeia or other generally recognized pharmacopoeia for use in animals and, more particularly, in humans.

Pharmaceutically Acceptable Salt: Pharmaceutically acceptable salt of a compound (e.g., aptamer), as used herein, refers to a product that contains the compound and one or more additional pharmaceutically-acceptable atoms or groups bound to the compound through ionic bond(s). In some embodiments, a pharmaceutically acceptable salt is produced by contacting the compound with an acid or a base. A pharmaceutically acceptable salt may include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts. As used herein, the term "aptamer" includes aptamers and pharmaceutically acceptable salts thereof, unless specifically indicated otherwise.

Pharmaceutical Composition: Pharmaceutical composition, as used herein, refers to a formulation comprising a compound (such as an aptamer) in a form suitable for administration to an individual. A pharmaceutical composition is typically formulated to be compatible with its intended route of administration. Examples of routes of administration include, but are not limited to, intravitreal, enteral and parenteral, including, e.g., subcutaneous injection or infusion, intravenous injection or infusion, intraarticular injection, intra-artery injection and infusion, intraaqueous humor injection and implantation, and intravitreous injection and implantation.

Protein: As used herein, "protein" is used synonymously with "peptide," "polypeptide," or "peptide fragment." A "purified" polypeptide, protein, peptide, or peptide fragment is substantially free of cellular material or other contaminating proteins from the cell, tissue, or cell-free source from which the purified protein is obtained, or substantially free from chemical precursors or other chemicals when chemically synthesized.

SELEX: The term SELEX, as used herein, refers to generally to the selection for nucleic acids that interact with a target molecule in a desirable manner, for example binding with high affinity to a protein; and the amplification of those selected nucleic acids. SELEX may be used to identify aptamers with high affinity to a specific target molecule. The term SELEX and "SELEX process" may be used interchangeably. In some embodiments, methods of selecting aptamers that bind to a target molecule are provided, comprising: (a) preparing a candidate mixture of nucleic acids, wherein the candidate mixture comprises modified nucleic acids in which at least one pyrimidine in at least one, or in each, nucleic acid of the candidate mixture is chemically modified at the C5-position; (b) contacting the candidate mixture with a target molecule, wherein nucleic acids having an increased affinity to the target molecule relative to other nucleic acids in the candidate mixture bind the target molecule, forming nucleic acid-target molecule complexes; (c) partitioning the increased affinity nucleic acids from the remainder of the candidate mixture; and (d) amplifying the increased affinity nucleic acids to yield a mixture of nucleic acids enriched in nucleic acid sequences that are capable of binding to the target molecule with increased affinity, whereby an aptamer to the target molecule is identified. In certain embodiments, the method further includes performing a slow off-rate enrichment process.

Sequence Identity: Sequence identity, as used herein, in the context of two or more nucleic acid sequences is a function of the number of identical nucleotide positions shared by the sequences (i.e., % identity=number of identical positions/total number of positions in the shorter of the two sequences being compared×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST). For sequence comparisons, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith and Waterman, Adv. Appl. Math., 2:482, 1981, by the homology alignment algorithm of Needleman and Wunsch, J. Mol. Biol., 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M. et al., Current Protocols in Molecular Biology, pub. by Greene Publishing Assoc. and Wiley-Interscience (1987)). As used herein, when describing the percent identity of a nucleic acid, such as an aptamer, the sequence of which is at least, for example, about 95% identical to a reference nucleotide sequence, it is intended that the nucleic acid sequence is identical to the reference sequence except that the nucleic acid sequence may include up to five point mutations per each 100 nucleotides of the reference nucleic acid sequence. In other words, to obtain a desired nucleic acid sequence, the sequence of which is at least about 95% identical to a reference nucleic acid sequence, up to 5% of the nucleotides in the reference sequence may be deleted or substituted with another nucleotide, or some number of nucleotides up to 5% of the total number of nucleotides in the reference sequence may be inserted into the reference sequence (referred to herein as an insertion). These mutations of the reference sequence to generate the desired sequence may occur at the 5' or 3' terminal positions of the reference nucleotide sequence or anywhere between those terminal positions, interspersed either individually among nucleotides in the reference sequence or in one or more contiguous groups within the reference sequence.

SOMAmer: As used herein, a "SOMAmer" or Slow Off-Rate Modified Aptamer refers to an aptamer (including an aptamers comprising at least one nucleotide with a hydrophobic modification) with an off-rate ($t_{1/2}$) of ≥30 minutes, ≥60 minutes, ≥90 minutes, ≥120 minutes, ≥150 minutes, ≥180 minutes, ≥210 minutes, or ≥240 minutes. In some embodiments, SOMAmers are generated using the improved SELEX methods described in U.S. Pat. No. 7,947, 447, entitled "Method for Generating Aptamers with Improved Off-Rates".

Spacer: A spacer, as used herein, refers to a non-nucleoside small molecule(s) that forms part of a modified oligonucleotide, and which typically takes the place of a nucleoside in the modified oligonucleotide. Exemplary spacer sequences include, but are not limited to, polyethylene glycols, hydrocarbon chains (such as 3 carbon spacers), and other polymers or copolymers. In some embodiments, a spacer provides a covalent molecular scaffold connecting two regions (such as two consensus or conserved regions) of an aptamer while preserving aptamer activity. In certain aspects, the spacer sequence may be covalently attached to an adjacent nucleotide through the 3' or 5' position on sugar moiety (including a modified sugar moiety) of the nucleotide.

Substantially Inhibit(s): Substantially inhibit(s), as used herein, refers to a complete or partial block, for example, any measurable reduction or at least a 10%, 20%, 25%, 30%, 35%, 40%, 45%, 50%, 55%, 60%, 65%, 70%, 75%, 80% or 90% inhibition or reduction of an activity or effect relative to a control. In some embodiments, inhibition of the activity of a target or an effect on a target (such as cleavage of the target) is measured in the presence of an aptamer, and the control is substantially similar conditions in the absence of the aptamer. In some embodiments, the activity measured is the activity of the complement system. One of ordinary skill in the art can appreciate the different assays and methods that may be used to measure the activity level, and thus inhibition, of the complement system. An exemplary method that may be used to determine the degree of inhibition of the complement system includes any assay for complement mediated hemolysis, which is described in greater detail in Example 3. Another exemplary method includes measuring the degree of proteolytic cleavage of C3-Protein into C3a and C3b as described in greater detail in Example 4.

Target Molecule: Target molecule (or target), as used herein, refers to any compound or molecule having a three dimensional chemical structure other than a polynucleotide upon which an aptamer can act in a desirable manner. Non-limiting examples of a target molecule include a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc. Virtually any chemical or biological effector may be a suitable target. Molecules of any size can serve as targets. A target can also be modified in certain ways to enhance the likelihood or strength of an interaction between the target and the nucleic acid. A target may also include any minor variation of a particular compound or molecule, such as, in the case of a protein, for example, minor variations in its amino acid sequence, disulfide bond formation, glycosylation, lipidation, acetylation, phosphorylation, or any other manipulation or modification, including conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules.

Therapeutically Effective Amount: As used herein, the term "therapeutically effective amount" generally means the amount necessary to ameliorate at least one symptom of a disorder or condition to be prevented, reduced, or treated as described herein. The phrase "therapeutically effective amount" as it relates to the aptamers of the present disclosure means the aptamer dosage that provides the specific pharmacological response for which the aptamer is administered in a significant number of individuals in need of such treatment. It is emphasized that a therapeutically effective amount of an aptamer that is administered to a particular individual in a particular instance will not always be effective in treating the conditions/diseases described herein, even though such dosage is deemed to be a therapeutically effective amount by those of skill in the art.

The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Further, ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of mean±20% of the indicated range, value, or structure, unless otherwise indicated. As used herein, the terms "include" and "comprise" are open ended and are used synonymously. It should be understood that the terms "a" and "an" as used herein refer to "one or more" of the enumerated components. The use of the alternative (e.g. "or") should be understood to mean either one, both, or any combination thereof of the alternatives Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

II. Overview

The present invention provides aptamers that specifically bind C3 protein (sometimes referred to as "C3 aptamers"). In some embodiments, an aptamer inhibits cleavage of C3 protein.

In some embodiments, an aptamer that binds C3 protein is provided, wherein the aptamer comprises the sequence 5'-KPGRMPDVD$_n$LPAWPSVGPAYRPP-3' (SEQ ID NO: 152), wherein K is a C-5 modified pyrimidine, C, U, T, G, or a 3-carbon spacer; each P is independently, and for each occurrence, a C-5 modified pyrimidine; R is A or G; M is C, U, T, a C-5 modified pyrimidine, or a 3-carbon spacer; each D is independently, and for each occurrence, an A, C, or a 3-carbon spacer; each V is independently, and for each occurrence, an A, G, C, or a 3-carbon spacer; L is A, U, T or a C-5 modified pyrimidine; W is G or a 3-carbon spacer; S is C or a 3-carbon spacer; Y is C, U, or T; and n is 0 or 1. In some embodiments, the aptamer comprises the sequence 5'-KPGRMPDVD$_n$LPAWPSVGPAYRPPM-3' (SEQ ID NO: 153), wherein each M is independently, and for each occurrence, C, U, T, a C-5 modified pyrimidine, or a 3-carbon spacer.

In some embodiments, an aptamer that binds C3 protein is provided, wherein the aptamer comprises the sequence 5'-KPGRMPDVD$_n$LPAWPSVGPACGPP-3' (SEQ ID NO: 131), wherein K is a C-5 modified pyrimidine, C, U, T, G, or a 3-carbon spacer; each P is independently, and for each occurrence, a C-5 modified pyrimidine; R is A or G; M is C, U, T, a C-5 modified pyrimidine, or a 3-carbon spacer; each D is independently, and for each occurrence, an A, C, or a 3-carbon spacer; each V is independently, and for each occurrence, an A, G, C, or a 3-carbon spacer; L is A, U, T or a C-5 modified pyrimidine; W is G or a 3-carbon spacer; S is C or a 3-carbon spacer; and n is 0 or 1. In some embodiments, the aptamer comprises the sequence 5'-KPGRMPDVD$_n$LPAWPSVGPACGPPM-3' (SEQ ID NO: 135), wherein each M is independently, and for each occurrence, C, U, T, a C-5 modified pyrimidine, or a 3-carbon spacer.

In some embodiments, an aptamer that binds C3 protein is provided, wherein the aptamer comprises the sequence 5'-KPGRMPXPAWPSVGPAYRPP-3' (SEQ ID NO: 154), wherein K is a C-5 modified pyrimidine, C, U, T, G, or a 3-carbon spacer; each P is independently, and for each occurrence, a C-5 modified pyrimidine; R is A or G; M is C, U, T a C-5 modified pyrimidine, or a 3-carbon spacer; V is A, G, C, or a 3-carbon spacer; W is G or a 3-carbon spacer; S is C or a 3-carbon spacer; Y is C, U, or T; and X is a linker selected from a substituted or unsubstituted C$_2$-C$_{20}$ linker, an alkylene glycol, and a polyalkylene glycol. In some embodiments, the aptamer comprises the sequence 5'-KPGRMPXPAWPSVGPAYRPPM-3' (SEQ ID NO: 155), wherein each M is independently, and for each occurrence, C, U, T, a C-5 modified pyrimidine, or a 3-carbon spacer.

In some embodiments, an aptamer that binds to C3 protein is provided, wherein the aptamer comprises the sequence 5'-KPGRMPXPAWPSVGPACGPP-3' (SEQ ID NO: 136), wherein K is a C-5 modified pyrimidine, C, U, T, G, or a 3-carbon spacer; each P is independently, and for each occurrence, a C-5 modified pyrimidine; R is A or G; M is C, U, T a C-5 modified pyrimidine, or a 3-carbon spacer; V is A, G, C, or a 3-carbon spacer; W is G or a 3-carbon spacer; S is C or a 3-carbon spacer; and X is a linker selected from a substituted or unsubstituted C$_2$-C$_{20}$ linker, an alkylene glycol, and a polyalkylene glycol. In some embodiments, the aptamer comprises the sequence 5'-KPGRMPXPAWPSVGPACGPPM-3' (SEQ ID NO: 137), wherein each M is independently, and for each occurrence, C, U, T, a C-5 modified pyrimidine, or a 3-carbon spacer.

In any of the embodiments described above, K may be a C-5 modified pyrimidine, C or G; each M may be independently, and for each occurrence, C or a C-5 modified pyrimidine; and/or L may be A or C-5 modified pyrimidine.

In some embodiments, an aptamer that binds to C3 protein is provided, wherein the aptamer comprises the sequence 5'-PAWPSVGPAYRPP-3' (SEQ ID NO: 156), wherein each P is independently, and for each occurrence, a C-5 modified pyrimidine; W is G or a 3-carbon spacer; S is C or a 3-carbon spacer; V is A, G or C; Y is C, U, or T; and R is G or A.

In some embodiments, an aptamer that binds to C3 protein is provided, wherein the aptamer comprises the sequence 5'-PAWPSVGPACGPP-3' (SEQ ID NO: 134), wherein each P is independently, and for each occurrence, a C-5 modified pyrimidine; W is G or a 3-carbon spacer; and S is C or a 3-carbon spacer; V is A, G or C.

In some embodiments, an aptamer that binds to C3 protein is provided, wherein the aptamer comprises a sequence that is at least 80%, at least 85%, at least 90%, at least 95%, at least 97%, at least 99%, or 100% identical to a sequence selected from SEQ ID NOs: 4 to 130 and 138 to 151, wherein each P is independently, and for each occurrence, a C-5 modified pyrimidine. In some embodiments, each P is NapdU. In some embodiments, an aptamer that binds to C3 protein is provided, wherein the aptamer comprises a sequence that is at least 80%, at least 85%, at least 90%, at least 95%, at least 97%, at least 99%, or 100% identical to a sequence selected from SEQ ID NOs: 4 to 28, 32 to 34, 37 to 75, 78 to 118, 121 to 130, and 139 to 151, wherein each P is independently, and for each occurrence, a C-5 modified pyrimidine. In some embodiments, each P is NapdU.

In some embodiments, an aptamer that binds C3 protein is provided, wherein the aptamer comprises a first region and a second region, wherein the first region comprises the sequence 5'-PAGPC-3' (SEQ ID NO: 132) and the second region comprises the sequence 5'-GPAYRPP-3' (SEQ ID NO: 157), wherein each P is independently, and for each occurrence, a C-5 modified pyrimidine; Y is C, U, or T; and R is G or A. In some embodiments, an aptamer that binds to C3 protein is provided, wherein the aptamer comprises a first region and a second region, wherein the first region comprises the sequence 5'-PAGPC-3' (SEQ ID NO: 132) and the second region comprises the sequence 5'-GPACGPP-3' (SEQ ID NO: 133), wherein each P is independently, and for each occurrence, a C-5 modified pyrimidine.

In some embodiments, the 3'-end of the first region is covalently linked to the 5'-end of the second region. In some embodiments, the first region and the second region are covalently linked by at least one, two, three, four or five linkers, wherein each linkers is independently selected from a nucleotide, a substituted or unsubstituted $C_2$-$C_{20}$ linker, an alkylene glycol, and a polyalkylene glycol. In some embodiments, each linker is independently selected from a nucleotide, a 3-carbon spacer, and a hexaethylene glycol.

In some embodiments, an aptamer that binds to C3 protein is provided, wherein the aptamer comprises the sequence 5'-PAGPC-3' (SEQ ID NO: 132), wherein each P is independently, and for each occurrence, a C-5 modified pyrimidine. In some embodiments, an aptamer that binds C3 protein is provided, wherein the aptamer comprises the sequence 5'-GPACGPP-3' (SEQ ID NO: 133), wherein each P is independently, and for each occurrence, a C-5 modified pyrimidine. In some embodiments, an aptamer that binds C3 protein is provided, wherein the aptamer comprises the sequence 5'-GPAYRPP-3' (SEQ ID NO: 157), wherein each P is independently, and for each occurrence, a C-5 modified pyrimidine; Y is C, U, or T; and R is G or A.

In some embodiments, an aptamer that binds to C3 protein is provided, wherein the aptamer comprises the sequence of SEQ ID NO: 125, wherein each P is independently, and for each occurrence, a C-5 modified pyrimidine. In some embodiments, each P is NapdU.

In some embodiments of the aptamers described herein, each C-5 modified pyrimidine is independently selected from: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-tyrosylcarboxyamide)-2'-deoxyuridine (TyrdU), 5-(N-3,4-methylenedioxybenzylcarboxyamide)-2'-deoxyuridine (MBndU), 5-(N-4-fluorobenzylcarboxyamide)-2'-deoxyuridine (FBndU), 5-(N-3-phenylpropylcarboxyamide)-2'-deoxyuridine (PPdU), 5-(N-imidizolylethylcarboxyamide)-2'-deoxyuridine (ImdU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N—R-threoninylcarboxyamide)-2'-deoxyuridine (ThrdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine), 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine. In some embodiments, each C-5 modified pyrimidine is independently selected from: 5-(N-1-naphthylmethylcarboxyamide)-2'-deoxyuridine (NapdU), 5-(N-1-naphthylmethylcarboxyamide)-2'-O-methyluridine, 5-(N-1-naphthylmethylcarboxyamide)-2'-fluorouridine, 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine. In some embodiments, each C-5 modified pyrimidine is 5-(N-naphthylmethylcarboxyamide)-2'-deoxyuridine (NapdU).

In any of the embodiments described herein, the aptamer may comprise at least one 2'-O-methyl modified nucleotide.

In any of the embodiments described herein, the aptamer may be from about 24 to about 100 nucleotides in length, or from about 30 to about 60 nucleotides in length, or from about 28 to about 60 nucleotides in length, or from about 40 to about 50 nucleotides in length, or about 28 nucleotides in length. In any of the embodiments described herein, the aptamer may be 24 to 100 nucleotides in length, or 30 to 60 nucleotides in length, or 28 to 60 nucleotides in length, or 28 to 50 nucleotides in length, or 28 to 40 nucleotides in length, or 40 to 50 nucleotides in length, or 28 to 32 nucleotides in length.

In some embodiments, an aptamer described herein binds C3 protein and inhibits cleavage of C3 protein. In some embodiments, the C3 protein is human C3 protein.

In some embodiments, the C3 aptamer may include up to about 100 nucleotides, up to about 95 nucleotides, up to about 90 nucleotides, up to about 85 nucleotides, up to about 80 nucleotides, up to about 75 nucleotides, up to about 70 nucleotides, up to about 65 nucleotides, up to about 60 nucleotides, up to about 55 nucleotides, up to about 50 nucleotides, up to about 45 nucleotides, up to about 40 nucleotides, up to about 35 nucleotides, up to about 30 nucleotides, up to about 25 nucleotides, or up to about 20 nucleotides. In some embodiments, the C3 aptamer may consist of up to 100 nucleotides, up to 95 nucleotides, up to 90 nucleotides, up to 85 nucleotides, up to 80 nucleotides, up to 75 nucleotides, up to 70 nucleotides, up to 65 nucleotides, up to 60 nucleotides, up to 55 nucleotides, up to 50 nucleotides, up to 45 nucleotides, up to 40 nucleotides, up to 35 nucleotides, up to 30 nucleotides, up to 25 nucleotides, or up to 20 nucleotides.

In another aspect this disclosure, the C3 aptamer may be at least 99% identical, at least 95% identical, at least 90% identical, at least 85% identical, at least 80% identical, or at least 75% identical to any of SEQ ID NOs: 4 to 151. In another aspect this disclosure, the C3 aptamer may be at least 95% identical, at least 90% identical, at least 85% identical, at least 80% identical, or at least 75% identical to any of SEQ ID NOs: SEQ ID NOs: 4 to 28, 32 to 34, 37 to 75, 78 to 118, 121 to 130, and 139 to 151. In some embodiments, an aptamer that binds C3 is 95%, 96%, 97%, 98%, 99%, or 100% identical to a sequence selected from SEQ ID NOs: SEQ ID NOs: 4 to 28, 32 to 34, 37 to 75, 78 to 118, 121 to 130, and 139 to 151. In a related aspect, the fragments thereof are 25 to 49 nucleotides in length (or from 25, 26, 27, 28, 29, 30, 31, 32, 33, 34, 35, 36, 37, 38, 39, 40, 41, 42, 43, 44, 45, 46, 47, 48 or 49 nucleotides in length to 26, 27, 28, 29, 30, 31, 32, 33, 34, 35, 36, 37, 38, 39, 40, 41, 42, 43, 44, 45, 46, 47, 48 or 49 nucleotides in length). In some embodiments, an aptamer that binds C3 is 25, 26, 27, 28, 29, 30, 31, 32, 33, 34, 35, 36, 37, 38, 39, 40, 41, 42, 43, 44, 45, 46, 47, 48 or 49 nucleotides in length.

In another aspect this disclosure, the C3 aptamer may have a dissociation constant ($K_d$) for C3 of about 10 nM or less. In another exemplary embodiment, the C3 aptamer has a dissociation constant ($K_d$) for the C3 protein of about 15 nM or less. In yet another exemplary embodiment, the C3 aptamer has a dissociation constant ($K_d$) for the C3 protein of about 20 nM or less. In yet another exemplary embodiment, the C3 aptamer has a dissociation constant ($K_d$) for the C3 protein of about 25 nM or less. In yet another exemplary embodiment, the C3 aptamer has a dissociation constant ($K_d$) for the C3 protein of about 30 nM or less. In yet another exemplary embodiment, the C3 aptamer has a dissociation constant ($K_d$) for the C3 protein of about 35 nM or less. In yet another exemplary embodiment, the C3 aptamer has a dissociation constant ($K_d$) for the C3 protein of about 40 nM or less. In yet another exemplary embodiment, the C3 aptamer has a dissociation constant ($K_d$) for the C3 protein of about 45 nM or less. In yet another exemplary embodiment, the C3aptamer has a dissociation constant ($K_d$) for the C3 protein of about 50 nM or less. In yet another exemplary embodiment, the C3 aptamer has a dissociation constant ($K_d$) for the C3 protein in a range of about 2 pM to about 10 nM (or 2 pM, 3 pM, 4 pM, 5 pM, 6 pM, 7 pM, 8 pM, 9 pM, 10 pM, 15 pM, 20 pM, 25 pM, 30 pM, 35 pM, 40 pM, 45 pM, 50 pM, 60 pM, 70 pM, 80 pM, 90 pM, 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 900 pM, 950 pM, 1000 pM, 2 nM, 3 nM, 4 nM, 5 nM, 6 nM, 7 nM, 8 nM, 9 nM or 10 nM). In yet another exemplary embodiment, the C3 aptamer has a dissociation constant ($K_d$) for the C3 protein in a range of at least 2 pM (or at least 2 pM, 3 pM, 4 pM, 5 pM, 6 pM, 7 pM, 8 pM, 9 pM, 10 pM, 15 pM, 20 pM, 25 pM, 30 pM, 35 pM, 40 pM, 45 pM, 50 pM, 60 pM, 70 pM, 80 pM, 90 pM, 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 900 pM, 950 pM, 1000 pM, 2 nM, 3 nM, 4 nM, 5 nM, 6 nM, 7 nM, 8 nM, 9 nM or 10 nM). A suitable dissociation constant can be determined with a binding assay using a multi-point titration and fitting the equation $y=(max-min)(Protein)/(K_d+Protein)+min$ as described in Example 2. It is to be understood that the determination of dissociation constants is highly dependent upon the conditions under which they are measured and thus these numbers may vary significantly with respect to factors such as equilibration time, etc. In any of the embodiments described herein, the aptamer, nucleic acid molecule comprises nucleotides of DNA, RNA or a combination thereof.

SELEX

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands". The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can also be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides", which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-NH2), 2'-fluoro (2'-F), and/or 2'-O-methyl (2'-OMe). See also, U.S. Patent Application Publication 20090098549, entitled "SELEX and PHOTOSELEX", which describes nucleic acid libraries having expanded physical and chemical properties and their use in SELEX and photoSELEX.

SELEX can also be used to identify aptamers that have desirable off-rate characteristics. See U.S. Patent Application Publication 20090004667, entitled "Method for Generating Aptamers with Improved Off-Rates", which describes improved SELEX methods for generating aptamers that can bind to target molecules. As mentioned above, these slow off-rate aptamers are known as "SOMAmers." Methods for producing aptamers or SOMAmers and photoaptamers or SOMAmers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates will dissociate and not reform, while complexes with slow dissociation rates will remain intact. Additionally, the methods include the use of modified nucleotides in the production of candidate nucleic acid mixtures to generate aptamers or SOMAmers with improved off-rate performance.

A variation of this assay employs aptamers that include photoreactive functional groups that enable the aptamers to covalently bind or "photocrosslink" their target molecules. See, e.g., U.S. Pat. No. 6,544,776 entitled "Nucleic Acid Ligand Diagnostic Biochip". These photoreactive aptamers are also referred to as photoaptamers. See, e.g., U.S. Pat. Nos. 5,763,177, 6,001,577, 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands". After the microarray is contacted with the sample and the photoaptamers have had an opportunity to bind to their target molecules, the photoaptamers are photoactivated, and the solid support is washed to remove any non-specifically bound molecules. Harsh wash conditions may be used, since target molecules that are bound to the photoaptamers are generally not removed, due to the covalent bonds created by the photoactivated functional group(s) on the photoaptamers.

In both of these assay formats, the aptamers or SOMAmers are immobilized on the solid support prior to being contacted with the sample. Under certain circumstances, however, immobilization of the aptamers or SOMAmers prior to contact with the sample may not provide an optimal assay. For example, pre-immobilization of the aptamers or SOMAmers may result in inefficient mixing of the aptamers or SOMAmers with the target molecules on the surface of the solid support, perhaps leading to lengthy reaction times and, therefore, extended incubation periods to permit efficient binding of the aptamers or SOMAmers to their target molecules. Further, when photoaptamers or photoSOMAmers are employed in the assay and depending upon the material utilized as a solid support, the solid support may tend to scatter or absorb the light used to effect the formation of covalent bonds between the photoaptamers or photoSOMAmers and their target molecules. Moreover, depending upon the method employed, detection of target molecules bound to their aptamers or photoSOMAmers can be subject to imprecision, since the surface of the solid support may also be exposed to and affected by any labeling agents that are used. Finally, immobilization of the aptamers or SOMAmers on the solid support generally involves an aptamer or SOMAmer-preparation step (i.e., the immobilization) prior to exposure of the aptamers or SOMAmers to the sample, and this preparation step may affect the activity or functionality of the aptamers or SOMAmers.

SOMAmer assays that permit a SOMAmer to capture its target in solution and then employ separation steps that are designed to remove specific components of the SOMAmer-target mixture prior to detection have also been described (see U.S. Patent Application Publication 20090042206, entitled "Multiplexed Analyses of Test Samples"). The described SOMAmer assay methods enable the detection and quantification of a non-nucleic acid target (e.g., a protein target) in a test sample by detecting and quantifying a nucleic acid (i.e., a SOMAmer). The described methods create a nucleic acid surrogate (i.e., the SOMAmer) for detecting and quantifying a non-nucleic acid target, thus allowing the wide variety of nucleic acid technologies, including amplification, to be applied to a broader range of desired targets, including protein targets.

Embodiments of the SELEX process in which the target is a peptide are described in U.S. Pat. No. 6,376,190, entitled "Modified SELEX Processes Without Purified Protein." In the instant case, the target is the C3-Protein.

Complement Component 3 (C3) Protein

The native human circulating C3-Protein used in the SELEX process was purified from blood and obtained from Quidel® Corporation, San Diego, Calif. (catalog number A401). For binding and activity studies circulating native C3-Protein from Quidel was used as was circulating human C3-Protein obtained from COMPLEMENT TECHNOLOGY, Inc., Tyler, Tex. (catalog number A113).

Chemical Modifications in Aptamers

Aptamers may contain modified nucleotides that improve its properties and characteristics. Non-limiting examples of such improvements include, in vivo stability, stability against degradation, binding affinity for its target, and/or improved delivery characteristics.

Examples of such modifications include chemical substitutions at the ribose and/or phosphate and/or base positions of a nucleotide. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-$NH_2$), 2'-fluoro (2'-F), and/or 2'-O-methyl (2'-OMe). See also, U.S. Patent Application Publication No. 20090098549, entitled "SELEX and PHOTOSELEX," which describes nucleic acid libraries having expanded physical and chemical properties and their use in SELEX and photoSELEX.

Specific examples of a C-5 modification include substitution of deoxyuridine at the C-5 position with a substituent independently selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) as illustrated immediately below.

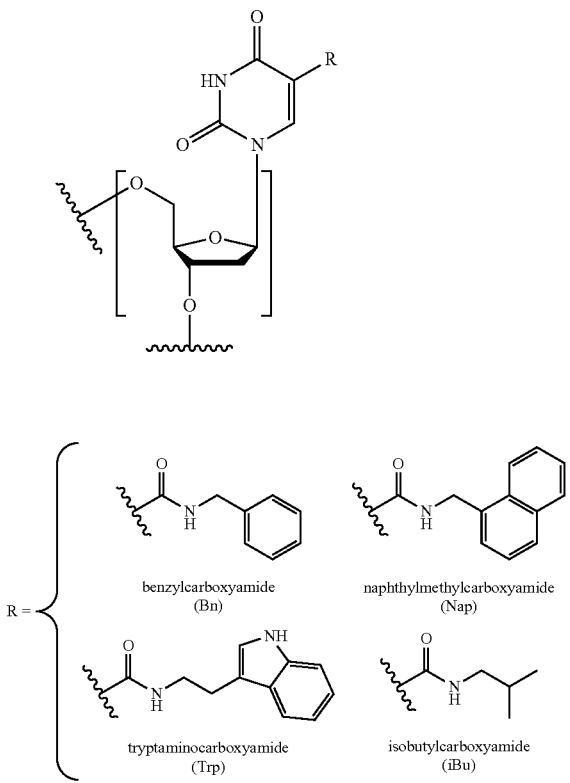

Chemical modifications of a C-5 modified pyrimidine can also be combined with, singly or in any combination, 2'-position sugar modifications, modifications at exocyclic amines, and substitution of 4-thiouridine and the like.

Representative C-5 modified pyrimidines include: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl] carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine or 5-(N-[1-(2,3-dihydroxypropyl)]carboxyamide)-2'-deoxyuridine).

In some embodiments, each X, Y, and/or Z is independently selected from 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PedU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine, and 5-(N-[1-(2,3-dihydroxypropyl)]carboxyamide)-2'-deoxyuridine). In some embodiments, each Z is 5-(N-benzylcarboxyamide)-2'-deoxyuridine (BndU).

If present, a modification to the nucleotide structure can be imparted before or after assembly of the polynucleotide. A sequence of nucleotides can be interrupted by non-nucleotide components. A polynucleotide can be further modified after polymerization, such as by conjugation with a labeling component.

Further, C-5 modified pyrimidine nucleotides include the following:

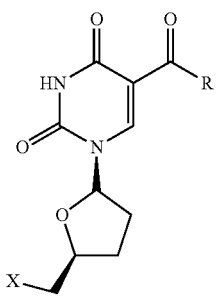

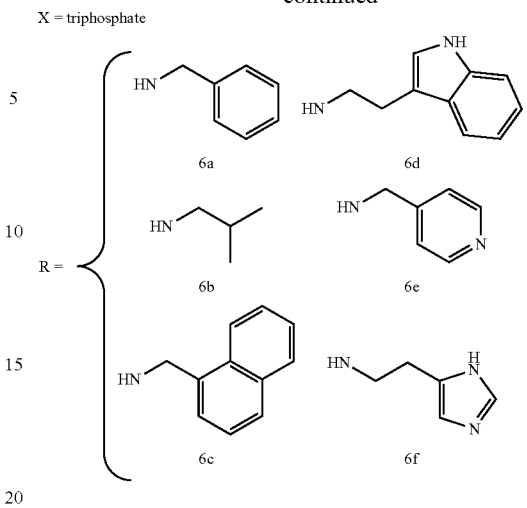

In some embodiments, the modified nucleotide confers nuclease resistance to the oligonucleotide. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

The present disclosure further provides for a formulation comprising two or more nucleic acid sequences selected from the group consisting of SEQ ID NOs: 4-130 and 138-151, wherein P is independently, and for each occurrence, a C-5 modified pyrimidine.

In another aspect, the C-5 modified pyrimidine is independently selected from: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-tyrosylcarboxyamide)-2'-deoxyuridine (TyrdU), 5-(N-3,4-methylenedioxybenzylcarboxyamide)-2'-deoxyuridine (MBndU), 5-(N-4-fluorobenzylcarboxyamide)-2'-deoxyuridine (FBndU), 5-(N-3-phenylpropylcarboxyamide)-2'-deoxyuridine (PPdU), 5-(N-imidizolylethylcarboxyamide)-2'-deoxyuridine (ImdU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N—R-threoninylcarboxyamide)-2'-deoxyuridine (ThrdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine), 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine.

In another aspect, the C-5 modified pyrimidine is independently selected from: 5-(N-1-naphthylmethylcarboxyamide)-2'-deoxyuridine (NapdU), 5-(N-1-naphthylmethylcarboxyamide)-2'-O-methyluridine, 5-(N-1-naphthylmethylcarboxyamide)-2'-fluorouridine, 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine.

In another aspect, the C-5 modified pyrimidine is 5-(N-naphthylmethylcarboxyamide)-2'-deoxyuridine (NapdU).

In another aspect, the two or more nucleic acid molecules of the formulation further comprises at least one additional modification selected from the group consisting of a 2'-O-methyl modified nucleotide, C3-spacer and a combination thereof.

In another aspect, the two or more nucleic acid molecules of the formulation further comprise at least one nucleotide position is substituted with a HEG linker or PEG linker and/or further comprises a HEG linker or PEG linker.

In another aspect, the two or more nucleic acid molecules of the formulation are each, independently, from about 24 to about 100 nucleotides in length, or from about 30 to about 60 nucleotides in length, or from about 40 to about 50 nucleotides in length; or further comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 additional nucleotides.

In another aspect, the complement component 3 (C3) protein is a human complement component 3 (C3) protein.

Pharmaceutical Compositions Comprising Aptamers

In some embodiments, pharmaceutical compositions comprising at least one aptamer described herein and at least one pharmaceutically acceptable carrier are provided. Suitable carriers are described in "Remington: The Science and Practice of Pharmacy, Twenty-first Edition," published by Lippincott Williams & Wilkins, which is incorporated herein by reference. Pharmaceutical compositions that include at least one aptamer described herein and at least one pharmaceutically acceptable carrier may also include one or more active agents that is not a C3 inhibitor.

The aptamers described herein can be utilized in any pharmaceutically acceptable dosage form, including, but not limited to, injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the aptamers described herein can be formulated: (a) for administration selected from any of intravitreal, oral, pulmonary, intravenous, intraarterial, intrathecal, intra-articular, rectal, ophthalmic, colonic, parenteral, intracisternal, intravaginal, intraperitoneal, local, buccal, nasal, and topical administration; (b) into a dosage form selected from any of liquid dispersions, gels, aerosols, ointments, creams, tablets, sachets and capsules; (c) into a dosage form selected from any of lyophilized formulations, dry powders, fast melt formulations, controlled release formulations, delayed release formulations, extended release formulations, pulsatile release formulations, and mixed immediate release and controlled release formulations; or (d) any combination thereof.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfate; (4) chelating agents such as ethylenediaminetetraacetic acid; (5) buffers such as acetates, citrates or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition should be sterile and should be fluid to the extent that easy syringability exists. The pharmaceutical composition should be stable under the conditions of manufacture and storage and should be preserved against the contaminating action of microorganisms such as bacteria and fungi.

The term "stable", as used herein, means remaining in a state or condition that is suitable for administration to a subject.

The carrier can be a solvent or dispersion medium, including, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol, and inorganic salts such as sodium chloride, in the composition. Prolonged absorption of the injectable compositions can be brought about by including in the composition an agent which delays absorption, for example, aluminum monostearate and gelatin.

Sterile injectable solutions can be prepared by incorporating the active reagent (e.g., an aptamer) in an appropriate amount in an appropriate solvent with one or a combination of ingredients enumerated above, as desired, followed by filtered sterilization. Generally, dispersions are prepared by incorporating at least one aptamer into a sterile vehicle that contains a basic dispersion medium and any other desired ingredient. In the case of sterile powders for the preparation of sterile injectable solutions, exemplary methods of preparation include vacuum drying and freeze-drying, both of which will yield a powder of an aptamer plus any additional desired ingredient from a previously sterile-filtered solution thereof.

In some embodiments, an aptamer is formulated for intravitreal injection. Suitable formulations for intravitreal administration are described, e.g., in "Remington: The Science and Practice of Pharmacy, Twenty-first Edition," published by Lippincott Williams & Wilkins. Ocular drug delivery is discussed, e.g., in Rawas-Qalaji et al. (2012) Curr. Eye Res. 37: 345; Bochot et al. (2012) J. Control Release 161:628; Yasukawa et al. (2011) Recent Pat. Drug Deliv. Formul. 5: 1; and Doshi et al. (2011) Semin. Ophthalmol. 26: 104. In some embodiments, a pharmaceutical composition comprising an aptamer is administered by intravitreal injection once per week, once per two weeks, once per three weeks, once per four weeks, once per five weeks, once per six weeks, once per seven weeks, once per eight weeks, once per nine weeks, once per 10 weeks, once per 11 weeks, once per 12 weeks, or less often than once per 12 weeks.

Oral compositions generally include an inert diluent or an edible carrier. They can be enclosed, for example, in gelatin capsules or compressed into tablets. For the purpose of oral therapeutic administration, the aptamer can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from a pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams, as generally known in the art. The reagents can also be prepared in the form of suppositories (e.g., with conventional suppository bases such as cocoa butter and other glycerides) or retention enemas for rectal delivery.

In some embodiments, an aptamer is prepared with a carrier that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of an aptamer may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

In some cases, it may be especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of an aptamer calculated to produce the desired therapeutic effect in association with the required pharmaceutical carrier. The specification for the dosage unit forms of aptamers described herein are dictated by and directly dependent on the characteristics of the particular aptamer and the particular therapeutic effect to be achieved, and the limitations inherent in the art of compounding such an active agent for the treatment of individuals.

Pharmaceutical compositions comprising at least one aptamer can include one or more pharmaceutical excipients. Examples of such excipients include, but are not limited to, binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel PH101 and Avicel PHI 02, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, and including magnesium stearate, colloidal silicon dioxide, such as Aerosil 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel PH101 and Avicel PHI 02; lactose such as lactose monohydrate, lactose anhydrous, and Pharmatose DCL21; dibasic calcium phosphate such as Emcompress; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In various embodiments, the formulations described herein are substantially pure. As used herein, "substantially pure" means the active ingredient (e.g., an aptamer) is the predominant species present (i.e., on a molar basis it is more abundant than any other individual species in the composition). In some embodiments, a substantially purified fraction is a composition wherein the active ingredient comprises at least about 50 percent (on a molar basis) of all macromolecular species present. Generally, a substantially pure composition will include more than about 80% of all macromolecular species present in the composition. In various embodiments, a substantially pure composition will include at least about 85%, at least about 90%, at least about 95%, or at least about 99% of all macromolecular species present in the composition. In various embodiments, the active ingredient is purified to homogeneity (contaminant species cannot be detected in the composition by conventional detection methods) wherein the composition consists essentially of a single macromolecular species.

Kits Comprising Aptamers

The present disclosure provides kits comprising any of the aptamers described herein. Such kits can comprise, for example, (1) at least one aptamer; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus.

Methods of Treatment

The present disclosure provides methods of preventing or treating {e.g., alleviating one or more symptoms of) medical conditions through the use of an aptamer described herein. The methods comprise administering a therapeutically effective amount of such aptamers to a subject in need thereof. The described aptamers can also be used for prophylactic therapy. In some embodiments, the aptamer is administered intravitreally. In some embodiments, the aptamer is administered orally or intravenously.

The aptamer used in methods of treatment can be an aptamer described herein, a pharmaceutically acceptable salt thereof, a prodrug thereof, or a pharmaceutically acceptable salt of a prodrug thereof.

The individual or subject can be any animal (domestic, livestock or wild), including, but not limited to, cats, dogs, horses, pigs and cattle, and preferably humans. As used herein, the terms patient, individual, and subject may be used interchangeably.

As used herein, "treating" describes the management and care of a patient for the purpose of treating a disease, condition, or disorder and includes the administration of an aptamer to prevent the onset of the symptoms or complications of a disease, condition or disorder; to alleviate symptoms or complications of the disease, condition, or disorder; or to eliminate the presence of the disease, condition or disorder in the patient. More specifically, "treating" includes reversing, attenuating, alleviating, minimizing, suppressing or halting at least one deleterious symptom or effect of a disease (disorder) state, disease progression, disease causative agent or other abnormal condition. Treatment is generally continued as long as symptoms and/or pathology ameliorate.

As used herein, "preventing" means preventing in whole or in part; ameliorating or controlling; reducing, lessening, or decreasing; or retarding or halting.

In various embodiments, the disclosed compositions and methods are used to treat age-related macular degeneration, autoimmune diseases, hematological disorders, infectious diseases, sepsis, inflammatory diseases, or neurodegenerative diseases.

In some embodiments, the disclosed compounds or pharmaceutically acceptable salts thereof, or prodrugs, can be administered in combination with other treatments that improve or eradicate the disease conditions described above. Compositions including the disclosed aptamers may contain, for example, more than one aptamer. In some examples, a composition containing one or more aptamers is administered in combination with another useful agent for treating the disease (e.g., an agent useful for treating age-related macular degeneration, an autoimmune disease, a hematological disorder, an infectious disease, sepsis, an inflammatory disease, or a neurodegenerative disease). In some embodiments, the currently available dosage forms of the known therapeutic agents for use in such combinations will be suitable.

"Combination therapy" (or "co-therapy") includes the administration of an aptamer composition and at least one second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present disclosure. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dose having a fixed ratio of each therapeutic agent or in multiple, single doses for each of the therapeutic agents.

The dosage regimen utilizing the aptamers is selected in accordance with a variety of factors, including, for example, type, species, age, weight, gender and medical condition of the subject; the severity of the condition to be treated; the route of administration; the renal and hepatic function of the subject; and the particular aptamer or salts thereof employed. An ordinarily skilled physician or veterinarian can readily determine and prescribe the effective amount of the composition required to prevent, counter or arrest the progress of the condition.

In general, the dosage, i.e., the therapeutically effective amount, ranges from about 1 µg to about 100 mg/kg body weight of the subject being treated, per day.

The following examples are provided to illustrate certain particular features and/or embodiments. These examples should not be construed to limit the disclosure to the particular features or embodiments described.

EXAMPLES

Example 1

Selection and Identification of Aptamers Having Binding Specificity to C3-Protein This example provides the representative method for the selection and production of DNA aptamers to the human C3-Protein.

Preparation of Candidate Mixture

A candidate mixture of partially randomized ssDNA oligonucleotides was prepared by polymerase extension of a DNA primer annealed to a biotinylated ssDNA template (shown in Table 1 below). The candidate mixture contained a 40 nucleotide randomized cassette containing dATP, dGTP, dCTP and 5-(N-naphthylmethylcarboxyamide)-2'-deoxyuridine triphosphate (NapdUTP).

TABLE 1

Sequences of Template and Primers

| Oligonucleotide Designation | Sequence (5'→3') | SEQ ID NO: |
|---|---|---|
| Template 1 | AB'AB'TTT TTT TTGTG TCT GTC TGT GTC CTC-(N)$_{40}$-GGAGTGGTAGAGGACTGG | 1 |
| Primer 1 | ATATATATCCAGTCCTCTACCACTCC | 2 |
| Primer 2 | AB'AB'TT TTT TTT GTG TCT GTC TGT GTC CTC | 3 |

B' = biotin

Five milliliters of a 50% slurry of Streptavidin Plus Ultra-Link Resin (PIERCE) was washed once with 2.5 mL of SB18T0.05 (40 mM HEPES (4-(2-Hydroxyethyl)piperazine-1-ethanesulfonic acid) buffer adjusted to pH 7.5 with NaOH, 102 mM NaCl, 5 mM KCl, 5 mM MgCl2 and 0.05% TWEEN 20) and thrice with 2.5 mL of 16 mM NaCl. Twenty nanomoles of template 1 (SEQ ID NO: 1) possessing two biotin residues (designated as B' in the sequence) and 40 randomized positions (designated as $N_{40}$ in the sequence) were added to the washed UltraLink SA beads and rotated at 37° C. for 30 minutes. The beads were then washed three times with 16 mM NaCl. Between each wash, the beads were recovered by centrifugation. The beads, now containing the captured template, were suspended in a 1.25 mL of extension reaction buffer [containing 24 nmol of primer (SEQ ID NO: 2), 1× SQ20 buffer (120 mM Tris-HCl, pH7.8, 10 mM KCl, 7 mM MgSO$_4$, 6 mM (NH$_4$)$_2$SO$_4$, 0.001% BSA and 0.1% Triton X-100), 187.5 units of KOD XL DNA Polymerase (EMD MILLIPORE), and 0.5 mM each of dATP, dCTP, dGTP and NapdUTP. The beads were allowed to incubate at 68° C. for 2 hours. The beads were then washed three times with 16 mM NaCl. The aptamer library was eluted from the beads with 1 mL of 20 mM NaOH. The eluted library and immediately neutralized with 15 µL of 1N HCl and 10 µL HEPES pH 7.5 and 1 µL 10% TWEEN-20. The library was concentrated with an AMICON Ultracel YM-10 filter to approximately 0.2 mL and the concentration of library determine by ultraviolet absorbance spectroscopy.

Labeling of Target Protein for Immobilization

Alexa488 Labeling of Target Protein

Untagged human C3-Protein purified from normal serum (QUIDEL, catalog number A401) was labeled by covalent coupling of Alexa Fluor® 488 (Molecular Probes™) to primary amines. C3-Protein (263 pmol in 68 μL) was mixed with a 137-fold molar excess of Alexa Fluor® 488 reactive dye and the reaction was allowed to incubate at room temperature for 2 hours. Unreacted label was removed using a Zeba™ spin desalting column (PIERCE) and the buffer exchanged into SB18T0.05.

Biotin Labeling of Human C3-Protein

Untagged human C3-Protein purified from normal serum (QUIDEL, catalog number A401) was biotinylated by covalent coupling of NHS-PEO4-biotin (PIERCE, EZ-Link NHS-PEG4-Biotin) to residues containing primary amines. Protein (200 pmol in 75 μL) was mixed with a 7-fold molar excess of NHS-PEG4-biotin and the reaction was allowed to incubate at 4° C. for 16 hours. After the reaction was completed, buffer was exchanged and unreacted NHS-PEG4-biotin removed by ultrafiltration using YM3 filters (MILLIPORE). The exchange buffer was SB18T0.05.

Immobilization of Target Protein

Alexa-fluor® 488 labeled target protein was immobilized on protein G magnetic beads (Dynabeads®, LIFE TECHNOLOGIES, or hereinafter referred to as protein G beads) for Round 1 through Round 4 of the SELEX process. Antibody coated beads were prepared by mixing 10 mg of beads with 70 μg of rabbit IgG anti-Alexa Fluor® 488 (INVITROGEN, MOLECULAR PROBES, A11094) in 1 mL of SB18T0.05 buffer. The mixture was allowed to incubate at 37° C. for 30 minutes. To remove unbound antibody, the beads were washed three times with 14 mL of SB18T0.05. Finally, the beads were suspended in 1 mL (10 mg/mL) of SB18T0.05 and stored at 4° C. until use.

Biotin labeled target protein was immobilized on MYONE-SA paramagnetic beads (MYONE SA, INVITROGEN, or hereinafter referred to as SA beads) for Round 5 through Round 9 of the SELEX process. Beads (50 mgs) were prepared by washing three times with 14 mL of SB18T0.05. Finally, the beads were suspended at 10 mgs/mL in SB18T0.05 and stored at 4° C. until use.

Aptamer Selection with Slow Off-Rate Enrichment Process

A total of nine rounds of the SELEX process were completed with selection for affinity and slow off-rate. Prior to each round a counter selection was performed to reduce background and to reduce the likelihood of obtaining aptamers with nonspecific binding to protein. Counter selections were performed as follows.

For Round 1, 100 μL of the DNA candidate mixture containing approximately 1 nmole of DNA in SB18T0.05 was heated at 95° C. for 5 minutes and then cooled to 70° C. for 5 minutes, then to 48° C. for 5 minutes and then transferred to a 37° C. block for 5 minutes. The sample was then combined with 10 μL of protein competitor mixture (0.1% HSA, 10 μM casein, and 10 μM prothrombin in SB18T0.05), and 1 mg (100 μL) of protein G beads and incubated at 37° C. for 10 minutes with mixing. Beads were removed by magnetic separation.

For Rounds 2-9, a 65 μL aliquot of the DNA candidate mixture obtained from the previous round (65% of eDNA obtained from previous round) was mixed with 16 μL of 5× SB18T0.05. The sample was heated to 95° C. and cooled to 37° C. at a rate of 0.1° C./second. The sample was then combined with 9 μL of protein competitor mixture (0.1% HSA, 10 μM casein, and 10 μM prothrombin in SB18T0.05), and 0.1 mg (10 μL) of protein G beads (Rounds 2-4) or SA beads (Rounds 5-9) and incubated at 37° C. for 10 minutes with mixing. Beads were removed by magnetic separation.

Following the first counter selection the target protein was pre-immobilized on protein G beads for the Round 1 selection process. To accomplish this, 2 mg of protein G beads with immobilized anti-Alexa Fluor® 488 antibody were mixed with 50 pmoles of Alexa-fluor® 488 labeled target protein and incubated for 30 minutes at 37° C. Unbound target was removed by washing the beads with SB18T0.05. The counter-selected-DNA candidate mixture (100 μL) was added to the beads and incubated at 37° C. for 60 minutes with mixing. No slow off-rate enrichment process was employed in the first Round and beads were simply washed 5 times with 100 μL SB18T0.05. Following the washes, the bound aptamer was eluted from the beads by adding 170 μL of 20 mM NaOH, and incubating at 37° C. for 5 minutes with mixing. The aptamer-containing-eluate (165 μL) was transferred to a new tube after magnetic separation of the beads and the solution neutralized by addition of 41 μL of 25 mM Tris-HCl pH 7.5 containing 80 mM HCl.

For Rounds 2-9, selections were performed with the DNA candidate mixture and target protein as described below while, in parallel, an identical selection was performed with the DNA candidate mixture, but without the target protein. Comparison of the Ct values obtained from PCR for the sample with target protein (signal S) and sample without target protein (background B) were used as a guide to reduce the target concentration in the next round. If the delta Ct value was greater than 4, but less than 8, the target protein was reduced three fold in the next round. If the delta Ct value was greater than 8, the target was reduced 10-fold in the next round.

For Round 2, labeled target protein (5 pmoles in 10 μL) was mixed with 40 μL of counter selected DNA candidate mixture and incubated at 37° C. for 15 minutes. A slow off-rate enrichment process was begun by adding 50 μL of 10 mM dextran sulfate followed by the immediate addition of 0.2 mg of protein G beads with immobilized anti-Alexa Fluor® 488 antibody. This was allowed to incubate for 15 minutes at 37° C. with mixing. Beads were then washed one time with 30% glycerol in SB18T0.05 and 5 times with 100 μL of SB18T0.05. The aptamer strand was eluted from the beads by adding 85 μL of 20 mM NaOH, and incubating at 37° C. for 5 minutes with mixing. Beads were removed by magnetic separation and 80 μL of aptamer eluate was transferred to a new tube and neutralized with 20 μL of solution consisting of 25 mM Tris-HCl pH 7.5 and 80 mM HCl. Rounds 3 and 4 were performed as described for Round 2 except dextran sulfate was added 15 minutes prior to the addition of protein G beans with immobilized anti-Alexa Fluor® 488 antibody. Also, no glycerol wash was performed.

Rounds 5 through 9 were performed using biotin labeled target protein. For Round 5, target (1.6 pmoles in 10 μL) was mixed with 40 μL of counter-selected-DNA candidate mixture and incubated at 37° C. for 15 minutes with mixing. A slow off-rate enrichment process was then begun by adding 50 μL of 10 mM dextran sulfate and the mixture allowed to incubate for an additional 15 minutes with mixing. SA beads (0.2 mg) were added in order to capture the target protein-aptamer complexes (15 minutes incubation at 37° C. with mixing). Beads were then washed 5 times with 100 μL of SB18T0.05. Bound aptamers were eluted from the beads by adding 85 μL of 20 mM NaOH, and incubating at 37° C. for 5 minutes with mixing. Beads were removed by magnetic separation and 80 μL of aptamer eluate was transferred to a new tube and neutralized with 20 μL of solution consisting of 25 mM Tris-HCl pH 7.5 and 80 mM HCl.

Round 6 was performed as Round 5 except that a 30 minute dextran challenge was utilized and labeled target protein captured with 0.05 mg of SA beads. Rounds 7 and 8 were performed like Round 6 except that only 0.16 pmoles of target protein was utilized. SELEX process Round 9 was performed as Round 8 except that only 0.05 pmoles of target protein was utilized.

Aptamer Amplification and Purification

Selected aptamer DNA from each round was amplified and quantified by QPCR. 48 μL DNA was added to 12 μL QPCR Mix (10× KOD DNA Polymerase Buffer; Novagen #71157, diluted to 5×, 25 mM $MgCl_2$, 5 μM forward PCR primer (Primer 1, SEQ ID NO: 2), 5 μM biotinylated reverse PCR primer (Primer 2, SEQ ID NO: 3), 5× SYBR Green I, 0.075 U/μL KOD XL DNA Polymerase, and 1 mM each dATP, dCTP, dGTP, and dTTP) and thermal cycled in A BIO-RAD MyIQ QPCR instrument with the following protocol: 1 cycle of 96° C. for 15 seconds, 55° C. for 10 seconds, and 69° C. for 30 minutes; followed by 30 cycles of 96° C. for 15 seconds, 69° C. for 1 minute. Quantification was done with the instrument software and the number of copies of DNA selected, with and without target protein, was compared to determine signal/background ratios.

Following amplification, the PCR product was captured on SA beads via the biotinylated antisense strand. 1.25 mL SA beads (10 mg/mL) were washed once with 14 mL 20 mM NaOH, twice with 14 mL SB18T0.05, resuspended in 1.25 mL 3 M NaCl+0.05% TWEEN, and stored at 4° C. 25 μL SA beads (10 mg/mL in 3 M NaCl) were added to 50 μL double-stranded QPCR products and incubated at 25° C. for 15 minutes with mixing. The beads were washed once with 16 mM NaCl and then the "sense" strand was eluted from the beads by adding 100 μL 20 mM NaOH, and incubating at 37° C. for 1 minute with mixing. The eluted strand was discarded and the beads were washed 3 times with SB18T0.05 and once with 16 mM NaCl.

Aptamer sense strand containing NapdU was prepared by primer extension from the immobilized antisense strand. The beads were suspended in 40 μL primer extension reaction mixture (1× Primer Extension Buffer (120 mM Tris-HCl pH 7.8, 10 mM KCl, 7 mM $MgSO_4$, 6 mM $(NH_4)_2SO_4$, 0.1% TRITON X-100 and 0.001% bovine serum albumin), 3 μM forward primer (Primer 1, SEQ ID NO: 2), 0.5 mM each dATP, dCTP, dGTP, and NapdUTP, and 0.015 U/μL KOD XL DNA Polymerase) and incubated at 68° C. for 60 minutes with mixing. The beads were washed 3 times with SB18T0.05, and the aptamer strand was eluted from the beads by adding 85 μL of 20 mM NaOH, and incubating at 37° C. for 1 minute with mixing. 80 μL aptamer eluate was transferred to a new tube after magnetic separation, neutralized with 20 μL of 80 mM HCl, buffered with 5 μL of 0.1 M HEPES, pH 7.5.

Selection Stringency and Feedback

The relative target protein concentration of the selection step was lowered each round in response to the QPCR signal (Δ Ct) following the rule below:

If $\Delta Ct < 4$, $[P]_{(i+1)} = [P]_{(i)}$

If $4 \leq \Delta Ct < 8$, $[P]_{(i+1)} = [P]_{(i)}/3.2$

If $\Delta Ct \geq 8$, $[P]_{(i+1)} = [P]_{(i)}/10$

Where [P]=protein concentration and i=current round number.

After each selection round, the convergence state of the enriched DNA mixture was determined. 10 μL double-stranded QPCR product was diluted to 200 μL with 4 mM $MgCl_2$ containing 1× SYBR Green I. Samples were analyzed for convergence using a $C_0t$ analysis which measures the hybridization time for complex mixtures of double stranded oligonucleotides. Samples were thermal cycled with the following protocol: 3 cycles of 98° C. for 1 minute, 85° C. for 1 minute; 2 cycles of 98° C. for 1 minute, then 85° C. for 30 minutes. During the 30 minutes at 85° C., fluorescent images were measured at 5-second intervals. The fluorescence intensity was plotted as a function of the logarithm of time, and an increased rate of hybridization with each SELEX round was observed, indicating sequence convergence.

Enriched Pool Sequencing & Aptamer Identification

After nine rounds of the SELEX process, the converged pool was sequenced. Sequence preparation was performed as follows. The pool was amplified by PCR using SELEX library-specific primers containing a unique barcode/index sequence (unique sequence identifier for each pool). Individual PCR products were quantified using a Quant-iT™ PicoGreen® dsDNA Reagent (LIFE TECHNOLOGIES) assay, combined at equimolar concentrations, and concentrated/buffer exchanged using an AMICON Ultra-0.5 Centrifugal Filter Device (MILLIPORE). The mixture was then purified by SDS-polyacrylamide gel electrophoresis (PAGE), and the eluate concentrated using an Amicon Ultra-0.5 Centrifugal Filter Device and visualized by PAGE to confirm the size, purity and yield of the final mix. The sample was submitted to SeqWright Genomic Services (GE HEALTHCARE, Houston, Tex.) for Ion Torrent PGM sequencing. From a sequence pool containing over 40,000 sequences, 384 were randomly selected and analyzed for convergence using custom software that determines sequence counts/copy number and identifies common convergence patterns using a local-alignment algorithm. Sequences with the greatest representation/copy number in the pool and at least one sequence from every convergence pattern were chosen for further characterization. Convergence pattern 1 was originally identified from sequences 8491-3_3 (SEQ ID NO: 4), 8491-94_3 (SEQ ID NO: 5), 8491-189_3 (SEQ ID NO: 8) and 8491-282_3 (SEQ ID NO: 9). The consensus domain derived from these four sequences was used to identify other members of convergence pattern 1 within the entire Round 9 sequence pool of over 40,000 sequences.

Aptamer Synthesis

For determination of the binding and inhibitory potential, individual aptamers were prepared by solid phase synthesis. The modified deoxyuridine-5-carboxamide amidite reagent used for solid-phase synthesis was prepared by: condensation of 5'-O-(4,4'-dimethoxytrityl)-5-trifluoroethoxycarbonyl-2'-deoxyuridine (Nomura et al. (1997) Nucl. Acids Res. 25:2784) with the appropriate [1-naphthylmethylamine] primary amine ($RNH_2$, 1.2 eq; $Et_3N$, 3 eq.; acetonitrile; 60° C.; 4 h); 3'-O-phophitidylation with 2-cyanoethyl-N,N-diisopropylchlorophosphoramidite (1.2 eq.; $iPr_2EtN$, 3 eq.; $CH_2Cl_2$; −10 to 0° C.; 4 h); and purification by flash chromatography on neutral silica gel (Still, et al. (1978) *J. Org. Chem.* 43:2923). Aptamers were prepared by solid phase synthesis using the phosphoramidite method (Beaucage and Caruthers (1981) *Tetrahedron Lett.* 22:1859) with some adjustments to the protocol to account for the unique base modifications described herein. Detrytilation was accomplished with 10% dichloroacetic acid in toluene for 45 seconds; coupling was achieved with 0.1 M phosphoramidites in 1:1 acetonitrile:dichloromethane activated by 5-benzylmercaptotetrazole and allowed to react 3 times for 5 minutes; capping and oxidation were performed according to instrument vendor recommendations. Deprotection was effected with gaseous ammonia or methylamine under optimized pressure, time, and temperature in a Parr stainless steel reactor. Products were eluted with deionized water into suitable 96-well plates, statistically sampled ($\sqrt{N}+1$) for LCMS characterization, quantified by UV spectrophotometry, and tested for protein binding affinity in buffered aqueous solution.

Example 2

Equilibrium Binding Constant ($K_d$) for Aptamers to C3-Protein

This example provides the method used herein to measure aptamer-C3-Protein binding affinities and to determine $K_d$. Briefly, radiolabeled DNA-aptamer ($^{32}$P) was heated for 3 minutes at 95° C. in SB18T0.01 buffer (40 mM HEPES, pH 7.5, 125 mM NaCl, 5 mM KCl, 5 mM MgCl$_2$, 0.01% TWEEN-20) and slowly cooled to 37° C. Complexes were formed by mixing radiolabeled DNA at about $1\times10^{-11}$ M with recombinant C3-Protein at a range of concentrations of $1\times10^{-7}$ M to $1\times10^{-12}$ M in SB18T0.01 buffer in a reaction volume of 60 µL, and incubating at 37° C. for 60 minutes. A portion of each reaction (5 µL) was transferred to a nylon membrane and dried to determine total counts in each reaction. Complexes were captured on ZORBAX resin (30 ng/µL, AGILENT), passed through a multi-screen HV Plate (MILLIPORE) under vacuum, and washed with 180 µL SB18T0.01 buffer to separate protein-bound complexes from unbound DNA. The nylon membrane and multi-screen HV Plate were imaged with a FUJI FLA-3000 Phosphorimager® and the amount of radioactivity in each sample was quantified using ImageQuant™ analysis software. The fraction of captured DNA was plotted as a function of C3-Protein concentration ($P_t$), and the equilibrium binding constants ($K_d$) were determined using the following formulation: y=(max−min) $(P_t)/(K_d+P_t)$+min.

Figure 3:
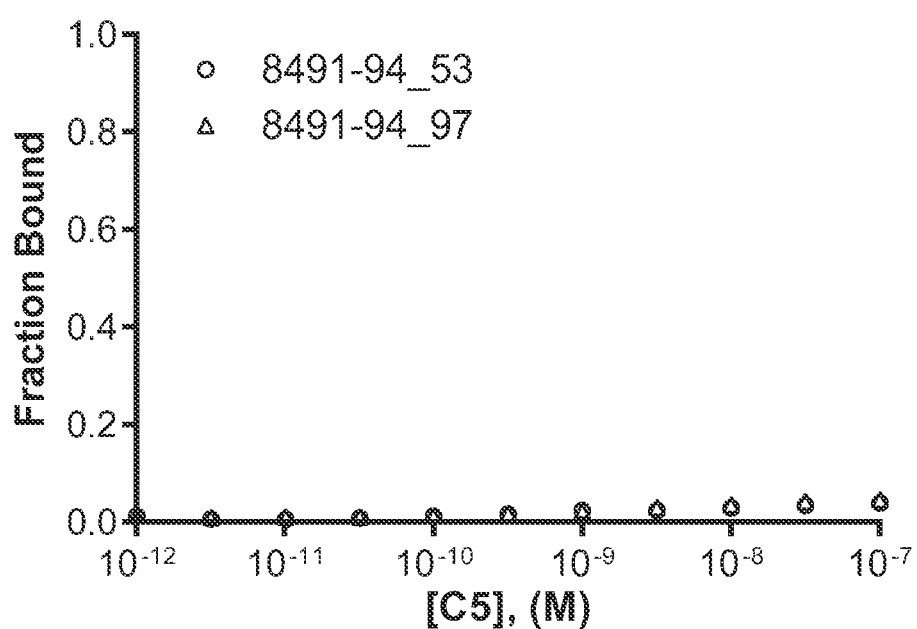
FIG. 3. Shown is a graphical representation of the fraction of bound DNA molecules (y-axis) plotted as a function of control protein human C5 concentration (x-axis). C5 protein concentration ranged from $1\times10^{-7}$ M to $1\times10^{-12}$ M. No discernible binding of 8491-94_53 (SEQ ID NO: 58) or 8491-94_97 (SEQ ID NO: 125) to human C5 protein was detected.

As an illustrated example, FIG. 2 shows a graph depicting the binding curves to human C3-Protein. DNA aptamers 8491-94_3 (SEQ ID NO: 5), 8491-94_53 (SEQ ID NO: 58), and 8491-94_97 (SEQ ID NO: 125) bind to C3-Protein with a $K_d$ of $3.13\times10^{-11}$ M, $3.34\times10^{-11}$ M and $5.49\times10^{-11}$ M, respectively. FIG. 3 shows a graph depicting binding of aptamers 8491-94_53 (SEQ ID NO: 58) and 8491-94_97 (SEQ ID NO: 125) to human C5 protein. No apparent binding to human C5 protein is detected illustrating the specificity of these aptamers for C3-Protein.

Table 2 shows the aptamer sequences and affinity for C3 of members of convergence pattern 1.

TABLE 2

Representative sequences of convergence pattern 1. Sequences shown as converged in the random region. All sequences also contain 5 bases of the 5'- and 3' primers (not shown) as well as a 3'-3' linked deoxythymidine at the 3'-terminus (not shown).

| Aptamer ID. No. | Sequence (5'→3') | $K_d$ (M) | SEQ ID NO. |
|---|---|---|---|
| 8491-3_3 | G-A-G-C-A-P-P-G-A-C-P-C-A-A-P-A-G-P-C-C-G-P-A-C-G-P-P-P-G-G-C-C-G-G-G-C-A-G-G-G | 1.19e-10 | 4 |
| 8491-94_3 | C-C-G-G-P-G-A-C-P-C-A-A-P-A-G-P-C-C-G-P-A-C-G-P-P-C-C-C-G-P-C-C-G-A-A-C-G-C-G | 3.13e-11 | 5 |
| 8491-389_3 | A-P-G-P-C-G-G-C-G-P-P-P-G-G-C-P-C-A-A-P-A-G-P-C-C-G-P-A-C-G-P-P-P-P-A-C-G-C-G-P | 2.95e-11 | 6 |
| 8491-390_3 | P-A-C-A-A-A-G-C-G-A-P-P-G-G-C-P-C-G-A-P-A-G-P-C-A-G-P-A-C-G-P-P-P-C-P-C-G-C-P-C | 4.12e-10 | 7 |
| 8491-189_3 | A-G-A-C-P-G-P-A-G-P-P-G-A-C-P-C-C-A-P-A-G-P-C-C-G-P-A-C-G-P-P-P-A-C-A-C-A-P-P-G | 3.35e-11 | 8 |
| 8491-282_3 | P-A-C-G-G-P-P-G-G-C-P-C-C-A-P-A-G-P-C-A-G-P-A-C-G-P-P-P-A-C-G-A-P-A-C-C-C-C | 2.70e-10 | 9 |
| 8491-395_3 | C-C-G-G-P-G-A-C-P-C-A-A-P-A-G-P-C-C-G-P-A-C-G-P-P-P-G-G-C-C-G-G-G-C-A-G-G-G | 3.52e-9 | 10 |
| 8491-394_3 | C-P-P-A-A-A-G-G-G-P-C-G-P-P-G-A-C-P-C-C-A-P-A-G-P-C-C-G-P-A-C-G-P-P-P-C-C-G-A | 4.48e-10 | 11 |
| 8491-397_3 | G-P-C-P-G-G-C-P-A-A-C-P-P-A-G-P-C-C-G-P-A-C-G-P-P-C-G-P-G-A-G-C-G-P-G-A-P-P-A-P | 3.11e-9 | 12 |
| 8491-396_3 | P-G-P-P-G-A-C-P-C-A-C-A-P-A-G-P-C-C-G-P-A-C-G-P-P-P-A-C-G-G-C-A-A-P-A-G-C-A-C-A | 3.11e-10 | 13 |
| 8491-393_3 | G-A-G-C-A-P-P-G-A-C-P-C-A-A-P-A-G-P-C-C-G-P-A-C-G-P-P-P-G-G-C-C-C-G-P-P-C-A-C-A-A-G | 2.5e-10 | 14 |
| 8491-406_3 | G-A-G-C-A-P-P-G-A-C-P-C-A-A-P-A-G-P-C-C-G-P-A-C-G-P-P-C-C-C-G-G-P-C-P-G-A-A-C-G-P-G | 2.47e-9 | 15 |
| 8491-387_3 | C-P-A-A-C-A-C-G-G-C-C-G-A-G-P-P-G-A-C-P-C-C-C-A-P-A-G-P-C-C-G-P-A-C-G-P-P-P-G-C | 5.19e-10 | 16 |

TABLE 2-continued

Representative sequences of convergence pattern 1. Sequences shown as converged in the random region. All sequences also contain 5 bases of the 5'- and 3' primers (not shown) as well as a 3'-3' linked deoxythymidine at the 3'-terminus (not shown).

| Aptamer ID. No. | Sequence (5'→3') | $K_d$ (M) | SEQ ID NO. |
|---|---|---|---|
| 8491-405_3 | A-P-G-P-C-G-G-C-G-P-P-P-G-A-C-P-C-A-A-P-A-G-P-C-C-G-P-A-C-G-P-P-P-G-G-C-C-G-G-G-C-A-G-G-G | 1.59e-10 | 17 |
| 8491-388_3 | A-C-G-G-P-G-A-C-P-C-C-A-P-A-G-P-C-C-G-P-A-C-G-P-P-C-C-C-G-C-G-G-A-C-G-C-A-C-C | 7.1e-10 | 18 |
| 8491-403_3 | G-A-G-C-A-P-P-G-A-C-P-C-A-A-P-A-G-P-C-C-G-P-A-C-G-P-P-P-P-P-P-G-G-G-C-C-G-G-G-G-G-G-C-A-G | 1.53-10 | 19 |
| 8491-385_3 | G-A-G-C-A-P-P-G-A-C-P-C-A-A-P-A-G-P-C-C-G-P-A-C-G-P-P-P-P-P-G-A-C-C-G-G-G-G-C-A-G-G-G-G | 1.46-10 | 20 |
| 8491-407_3 | G-A-G-C-A-P-P-G-A-C-P-C-A-A-P-A-G-P-C-C-G-P-A-C-G-P-P-P-P-A-C-G-C-G-P | 2.08e-10 | 21 |
| 8491-402_3 | P-C-C-C-A-C-A-C-G-A-C-G-A-A-P-P-P-G-A-C-P-C-A-A-P-A-G-P-C-G-P-A-C-G-P-P-P-P-A | 7.39e-11 | 22 |
| 8491-408_3 | C-A-A-G-C-C-P-C-P-C-G-G-P-P-P-G-G-C-P-A-A-A-P-A-G-P-C-C-G-P-A-C-G-P-P-P-P-C-A-C | 1.61e-10 | 23 |
| 8491-400_3 | P-P-G-A-C-P-C-G-A-P-A-G-P-C-C-G-P-A-C-G-P-P-P-G-C-G-G-A-A-P-A-C-C-A-G-C-P-G-A-C | 1.20e-9 | 24 |
| 8491-404_3 | G-A-G-C-P-P-P-P-P-P-G-A-C-P-C-A-A-P-P-A-G-P-C-C-G-P-A-C-G-P-P-P-P-P-P-G-G-C-C-G-G-G-C-A-G-G-G | 1.85e-10 | 25 |
| 8491-386_3 | A-G-C-A-A-C-P-P-G-A-C-P-C-A-A-P-A-G-P-C-C-G-P-A-C-G-P-P-P-A-P-G-C-G-A-G-A-A-C-A | 1.04e-10 | 26 |
| 8491-399_3 | C-P-A-P-G-A-G-G-C-P-G-A-P-P-C-A-A-P-A-G-P-C-A-G-P-A-C-G-P-P-C-G-C-C-C-A-P-C | 8.61e-9 | 27 |
| 8491-409_3 | P-C-C-C-P-P-P-G-G-C-P-C-G-A-P-A-G-P-C-G-G-P-A-C-G-P-P-P-P-G-G-G-A-G-G-C-G-P-G | 3.16e-10 | 28 |
| 8491-401_3 | G-A-G-P-A-C-P-P-C-G-A-C-P-C-A-A-P-A-G-P-C-C-G-P-P-A-C-G-P-P-P-G-G-C-C-G-G-C-A-G-G-C | NB | 29 |
| 8491-398_3 | C-G-P-G-A-C-P-C-G-A-P-G-A-G-P-C-A-P-A-G-P-C-G-G-P-P-C-C-G-P-C-C-G-A-A-C-G-C-G | NB | 30 |

P-NapdU
NB-No Binding

Example 3

Inhibition of Complement Mediated Hemolysis

This example provides the method used herein to measure aptamer-inhibition of complement mediated hemolysis of antibody coated sheep red blood cells. A 1:20 dilution of C3-Protein depleted human serum (COMPLEMENT TECHNOLOGIES catalog number A314) is mixed with 20 or 25 nM human C3-Protein (as indicated) and antibody coated sheep erythrocytes ($7 \times 10^7$ cells/mL) COMPLEMENT TECHNOLOGIES catalog number B200) with or without aptamers at the indicated final concentration. Control samples without addition of aptamers or without addition of C3-Protein and aptamers is also included along with a positive control in which all erythrocytes were lysed. Samples were diluted and the assay performed in a total volume of 0.075 mL in gelatin veronal buffer (GVB++; 0.1% gelatin, 0.15 mM calcium chloride, 0.5 mM magnesium chloride 5 mM Veronal, 145 mM NaCl, 0.025% $NaN_3$, pH 7.3, COMPLEMENT TECHNOLOGIES catalog number B102) and incubated for 30 min at 37° C. Samples were centrifuged (200×g for 10 minutes) and the absorbance of the supernatant at 412 nm was measured following a 1 in 4 dilution in GVB++ buffer. The ability of aptamers of convergence pattern 1 to inhibit complement-mediated hemolysis is shown in FIG. 4 and FIG. 5.

Figure 4:
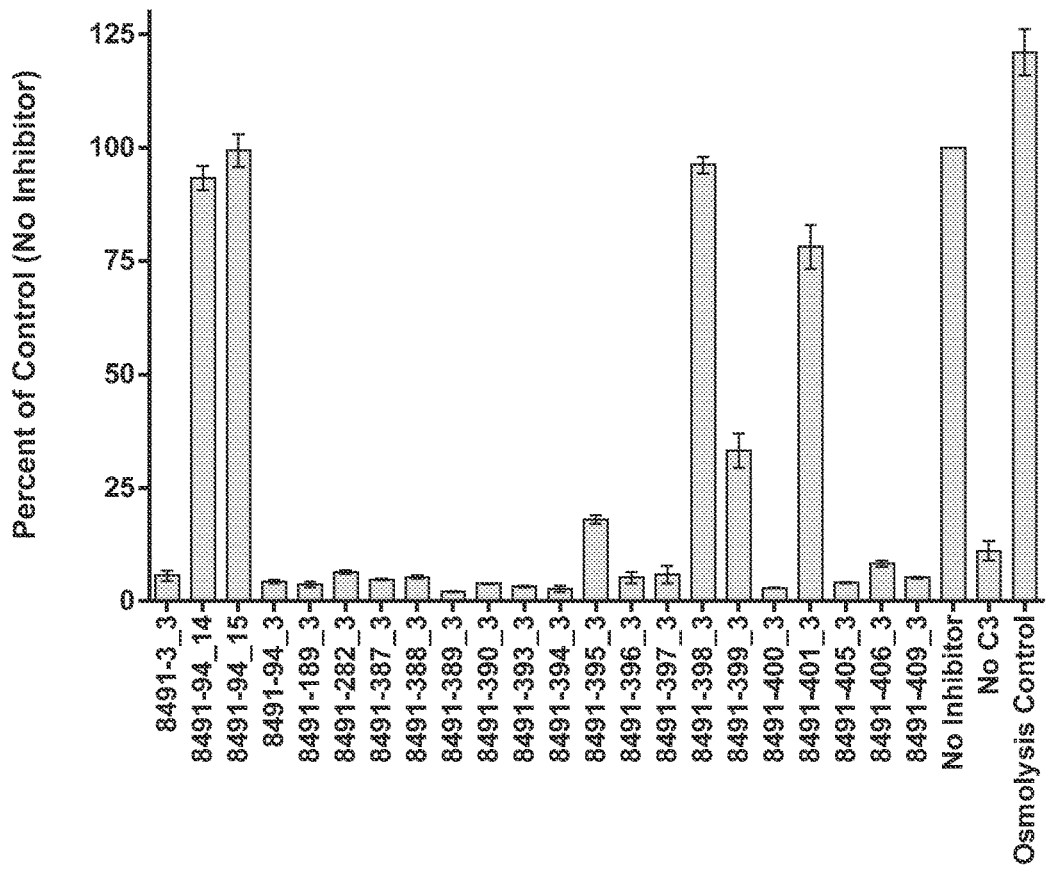
FIG. 4. Pattern 1 sequences inhibit complement-mediated hemolysis of antibody coated sheep red blood cells in human serum. Experiments were performed as described in Example 3 using 25 nM human C3-Protein and 1 µM of the indicated aptamer. Each bar displays the median percent hemolysis of two independent experiments relative to the "no inhibitor control". The osmolysis control shows the relative percent absorbance at 412 nm when all the red blood cells are lysed. Error bars indicate the range of the two experiments. Non-binding aptamers 8491-94_14 (SEQ ID NO:35); 8491-94_15 (SEQ ID NO: 36); 8491-398_3 (SEQ ID NO: 30) and 8491-401_3 (SEQ ID NO: 29) inhibited lysis by less than 25%. C3-protein binding aptamers 8491-3_3 (SEQ ID NO: 4); 8491-94_3 (SEQ ID NO: 5); 8491-189_3 (SEQ ID NO: 8); 8491-282_3 (SEQ ID NO: 9); 8491-387_3 (SEQ ID NO: 16); 8491-388_3 (SEQ ID NO: 18); 8491-389_3 (SEQ ID NO: 6); 8491-390_3 (SEQ ID NO: 7); 8491-393_3 (SEQ ID NO: 14); 8491-394_3 (SEQ ID NO: 11); 8491-395_3 (SEQ ID NO: 10); 8491-396_3 (SEQ ID NO: 13); 8491-397_3 (SEQ ID NO: 12); 8491-399_3 (SEQ ID NO: 27); 8491-400_3 (SEQ ID NO: 24); 8491-405_3 (SEQ ID NO: 17); 8491-406_3 (SEQ ID NO: 15) and 8491-409_3 (SEQ ID NO: 28) inhibited lysis by greater than 50%.
Figure 5:
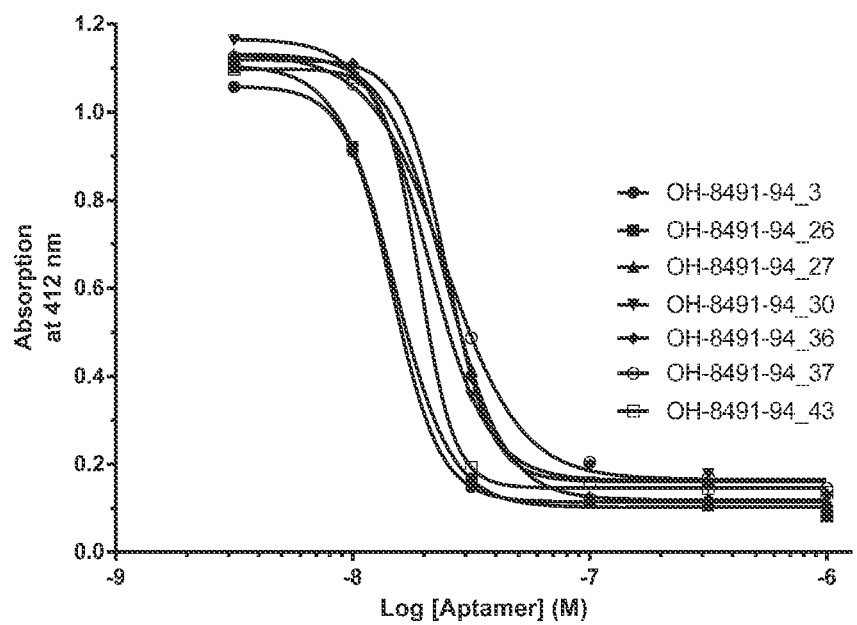
FIGS. 5A and 5B. Inhibition of complement-mediated hemolysis of antibody coated sheep red blood cells in human serum by 8491-94_3 (SEQ ID NO: 5) and its derivatives. Experiments were performed as described in Example 3 using various concentrations of aptamers as shown in the figure with a fixed concentration (20 nM) of human C3-Protein. Data are fit to a 4-parameter logistic equation to determine the $IC_{50}$. Panel (A) shows that 8491-94_3 inhibits with an $IC_{50}$ of 14.8 nM while 8491-94_26 (SEQ ID NO: 54), 8491-94_27 (SEQ ID NO: 55), 8491-94_30 (SEQ ID NO:60), 8491-94_36 (SEQ ID NO: 66), 8491_94_37 (SEQ ID NO: 67) and 8491-94_43 (SEQ ID NO: 73) inhibit with $IC_{50}$ values of 15.1 nM, 24.6 nM, 20.9 nM, 25.0 nM, 24.7 nM and 19.2 nM, respectively. Panel (B) shows that the aptamer, 8491-94_53 (SEQ ID NO: 58), inhibits with an $IC_{50}$ of 17.1 nM while aptamers 8491-94_90 (SEQ ID NO: 118), 8491-94_97 (SEQ ID NO: 125) and 8491-94_100 (SEQ ID NO: 128) inhibit with $IC_{50}$ values of 18.9 nM, 15.6 nM, and 19.7 nM, respectively.
Figure 5:
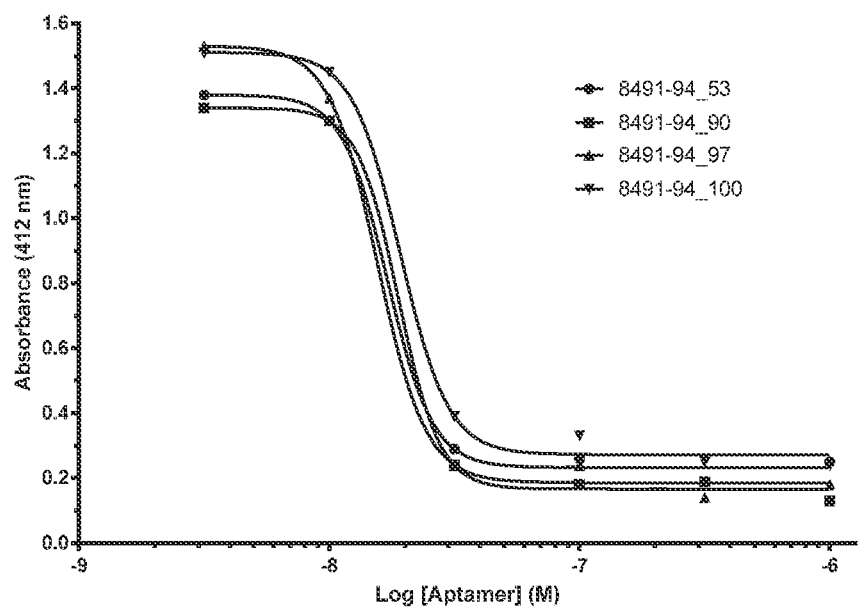

Aptamers of convergence pattern 1 were found to have the desired high affinity binding (Table 2) and inhibition properties (FIG. 4). Twenty-seven independent sequences were identified within this pattern from the original sequence pool of over 40,000 sequences. All 27 sequences were tested for binding to human C3-Protein. Twenty-five were found to bind to human C3-Protein with high affinity (Table 2). Twenty of these sequences were also tested for their ability to inhibit complement-mediated hemolysis of antibody coated sheep red blood cells (FIG. 4). The 18 aptamers that were strong inhibitors in the hemolytic assay were those that bound to C3-Protein with high affinity. Those that did not bind to C3-Protein were not inhibitors (<25% inhibition). As further controls, two sequences were tested for binding to C3-Protein and for inhibition of C3-Protein in which a single NapdU modified nucleotide within the 8491-94_3 sequence (SEQ ID NO: 5) was replaced with a deoxythymidine nucleotide. These two sequences, 8491-94_14 (SEQ ID NO: 35) and 8491-94_15 (SEQ ID NO: 36), did not bind to C3-Protein with high affinity (see Table 3 below) or inhibit hemolysis (FIG. 4). These data indicate that high affinity binding to C3-Protein is required for the observed inhibition properties and that the modified NapdU nucleotides contribute substantially to the overall affinity of binding.

Figure 1:
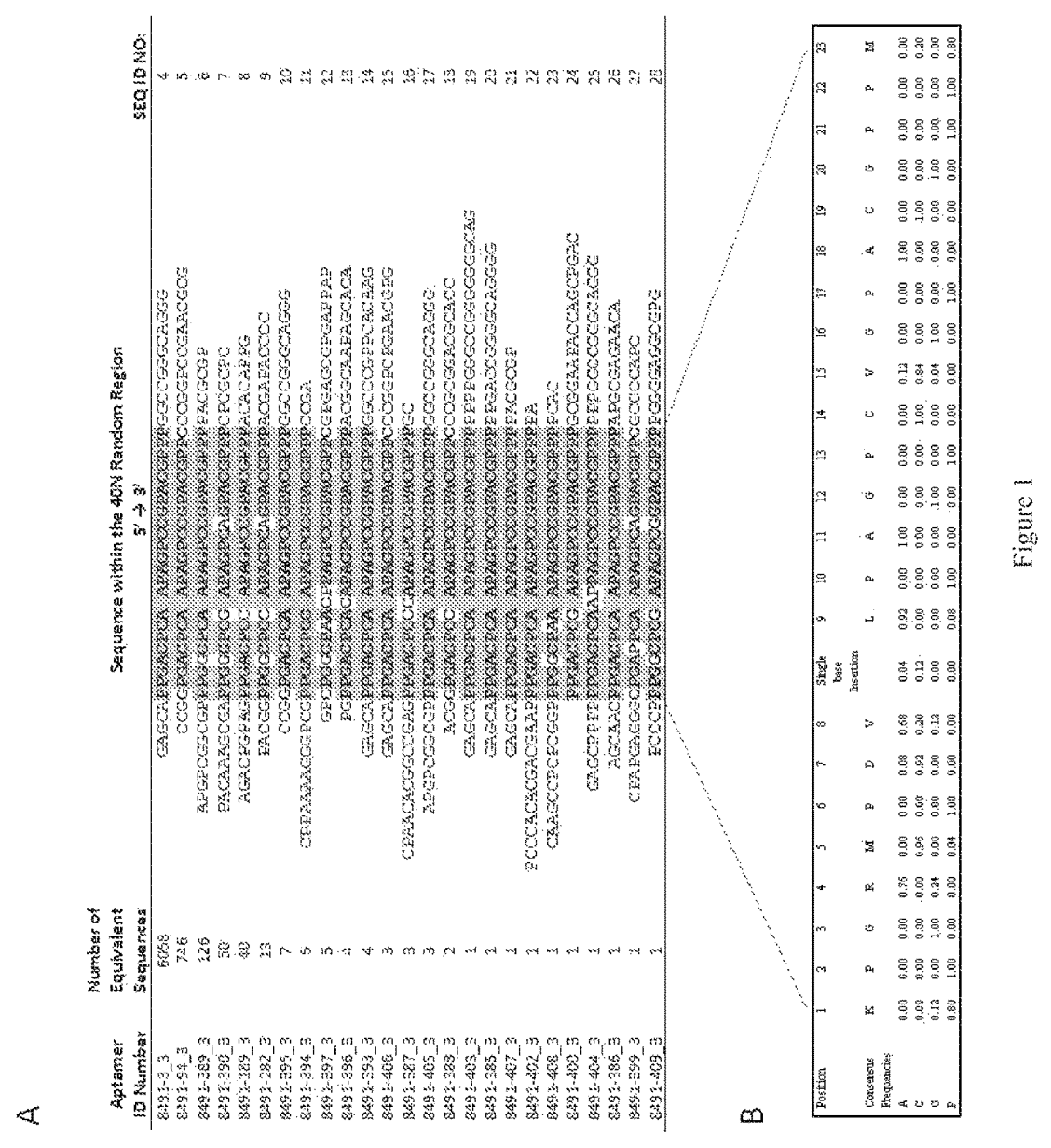

After excluding two sequences shown not to bind to C3-Protein, the remaining 25 sequences were aligned to reveal a consensus domain 23 nucleotides in length (FIG. 1). The number of times each sequence was identified is shown in this figure. Sequences with more than 5 nucleotide differences from any other sequence were considered to be independently selected sequences. Sequences with 1 to 5 nucleotide differences from any specific sequence shown in FIG. 1 are included in the total sequence count for that sequence. This domain is characterized by having a conserved NapdU base (P) at positions 2, 6, 10, 13, 17, 21 and 22. Position 1 was a P in 20 of the 25 sequences, a guanine (G) in 3 sequences [8491-94_3 (SEQ ID NO: 5), 8491-395_3 (SEQ ID NO: 10) and 8491-388_3 (SEQ ID NO: 18)] and a cytosine (C) in two sequences [8491-397 (SEQ ID NO: 12) and 8491-399 (SEQ ID NO: 27)]. Position 3 is a G while position 4 is a purine base where A occurs 19 times and G occurs 6 times. Position 5 is a C in all but one sequence [8491-399_3 (SEQ ID NO: 27)], where it is a P. Position 7 is a C in 23 of the sequences and an A in two sequences [8491-397_3 (SEQ ID NO: 12) and 8499-408_3 (SEQ ID NO: 23)]. Position 8 is an A in 17 sequences of the 25 sequences under consideration, a C in 5 sequences and a G in 3 sequences. A single base insertion (C or A) within the consensus motif between positions 8 and 9 is observed in 4 sequences [8491-387 (SEQ ID NO: 16), 8491-396 (SEQ ID NO: 13), 8491-397 (SEQ ID NO: 12), and 8491-404 (SEQ ID NO: 25)]. Position 9 is an A except in two sequences [8491-404 (SEQ ID NO: 25) and 8491-397 (SEQ ID NO: 12)] where it is a P. One of these sequences was shown to bind to C3-Protein with a $K_d$ of 3.1 nM [8491-397_3 (SEQ ID NO: 12)]. Positions 10-14 are absolutely conserved with the sequence 5'-P-A-G-P-C-3' (SEQ ID NO: 132). Position 15 is a C except in three sequences where it is an A [8491-390_3 (SEQ ID NO: 7), 8491-282_3 (SEQ ID NO: 9) and 8491-399_3 (SEQ ID NO: 27)] and one sequence where it is a G [8491-409_3 (SEQ ID NO: 28)]. Positions 16-22 are entirely conserved in those sequences that bind to C3-Protein. These positions contain the sequence 5'-G-P-A-C-G-P-P-3' (SEQ ID NO: 133). Of the 25 sequences under consideration, position 23 is a P in 20 cases but is a C in 5 cases.

Of these high affinity inhibitors of human C3-Protein, sequence 8491-94_3 (SEQ ID NO: 5) was chosen for post-SELEX modification to identify improved properties and characteristics. As shown in FIG. 5A, this sequence could inhibit the hemolysis of antibody coated sheep red blood cells in this system with an $IC_{50}$ of 14.8 nM.

Example 4

Inhibition of C3a Release

Figure 6:
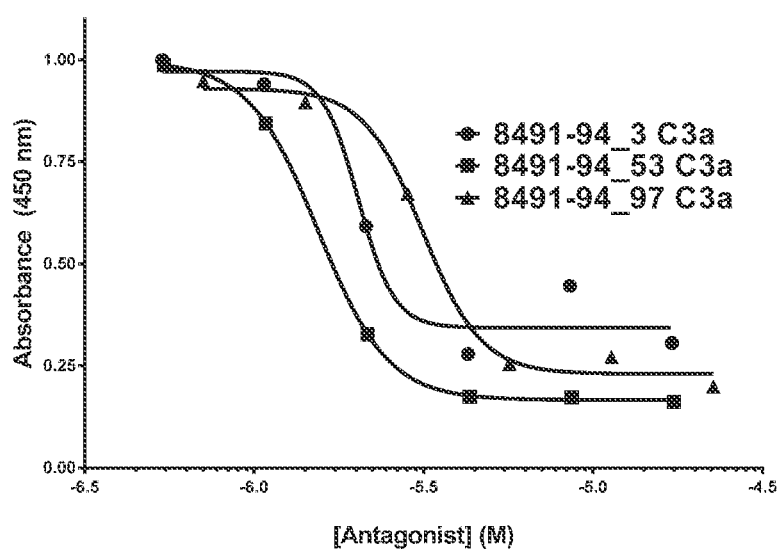
FIG. 6. Inhibition of C3a release (in 34% normal human serum) by 8491-94_3 (SEQ ID NO: 5), 8491-94_53 (SEQ ID NO: 58) and 8491-94_97 (SEQ ID NO: 125) following zymosan-A-induced complement activation. Experiments were performed as described in Example 4. Data are fit to a 4-parameter logistic equation to determine the $IC_{50}$ values of 2 μM, 1.5 μM, and 3 μM for 8491-94_3 (SEQ ID NO: 5), 8491-94_53 (SEQ ID NO: 58) and 8491-94_97 (SEQ ID NO: 125), respectively.
Figure 12:
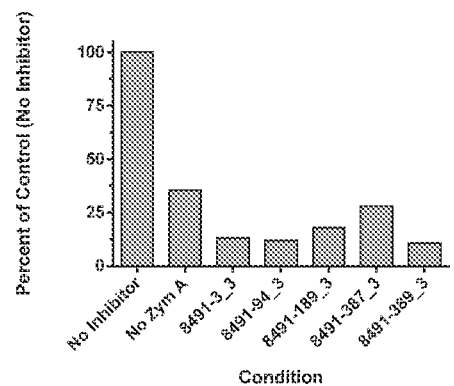
FIGS. 12A and 12B. (A) Inhibition of C3a release in 10% normal human serum by the pattern 1 SOMAmers 8491-3_3 (SEQ ID NO: 4), 8491-94_3 (SEQ ID NO: 5), 8491-189_3 (SEQ ID NO: 8), 8491-387_3 (SEQ ID NO: 16) and 8491-389_3 (SEQ ID NO: 6) following zymosan-A-induced complement activation. The aptamer concentration was 2 μM and the experiment was performed as described in Example 4. Data are presented as the percent of the signal obtained from the no inhibitor control. (B) Control experiment demonstrating that 8491-3_3 (SEQ ID NO: 4), (8491-94_3 (SEQ ID NO: 5), 8491-189_3 (SEQ ID NO: 8), 8491-387_3 (SEQ ID NO: 16) and 8491-389_3 (SEQ ID NO: 6) do not materially interfere with the assay for C3a release. Data are presented as the percent of the signal obtained from the no inhibitor control.
Figure 12:
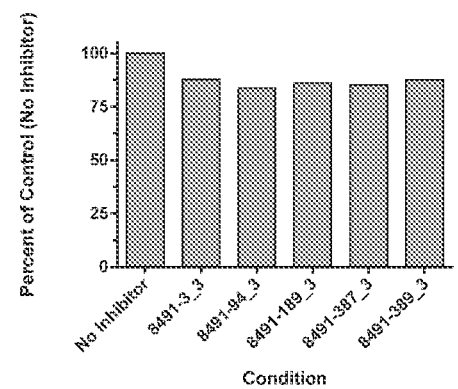

This example provides the method used herein to measure the ability of an aptamer to prevent the proteolytic cleavage of C3-Protein into C3a and C3b and therefore prevent the activation of human C3-Protein. The principal of the assay is to initiate the alternative pathway of the complement system in human serum with preactivated Zymosan (COMPLEMENT TECHNOLOGIES catalog number B400) in the presence or absence of an aptamer. When the pathway is initiated, C3a is released and then rapidly metabolized into C3a desArg by endopeptidase already present in the serum. The relative amount of C3a desArg is then measured using the DB OptEIA™ human C3a enzyme-linked immunosorbent assay (ELISA) kit (BD BIOSCIENCES, San Diego, Calif. catalog number 550499) according to the manufacturer's directions. Normal human serum (COMPLEMENT TECHNOLOGIES catalog number NHS) is diluted to 10% or 34% in gelatin veronal buffer (0.1% gelatin, 5 mM Veronal, 145 mM NaCl, 0.025% NaN$_3$, pH 7.3, COMPLEMENT TECHNOLOGIES catalog number B101) containing 10 nM magnesium EGTA (COMPLEMENT TECHNOLOGIES catalog number B106) with or without the addition of an aptamer at a predetermined concentration. The complement cascade is initiated by the addition of Zymosan-A (0.5 mg/mL) and the complement cascade allowed to proceed for 30 minutes at 37° C. Zymosan-A is then removed from the solution by centrifugation (7,000×g for 4 minutes) at room temperature and the sample diluted appropriately for measurement by the human C3a ELISA kit. As a control for the possibility of aptamer interference with the performance of the C3a desArg ELISA, aptamers are added after the 30 minute reaction. The ability of the representative convergence pattern 1 sequences, 8491-3_3 (SEQ ID NO: 4), (8491-94_3 (SEQ ID NO: 5), 8491-189_3 (SEQ ID NO: 8), 8491-387_3 (SEQ ID NO: 16) and 8491-389_3 (SEQ ID NO: 6) to inhibit C3a release following zymosan-A-induced complement activation is shown in FIG. 12A. As shown in FIG. 12B, the observed inhibition is not due to aptamer interference of the C3a detection system (C3a desArg ELISA). In this control, the aptamer is added after the complement cascade has run such that the aptamer is present at the same concentration as in the corresponding inhibition experiment shown in FIG. 12A. In FIG. 6 the pattern 1 member, 8491-94_3 (SEQ ID NO: 5), is shown to inhibit C3a release in 34% normal human serum, with an $IC_{50}$ of 2 µM.

Deoxythymidine Substitution for NapdU in the 8491-94_3 (50-mer).

A deoxythymidine (dT) walk was performed on 8491-94_3 (SEQ ID NO: 5). A single dT was substituted for one of eight positions containing a modified nucleotide (NapdU). The dT walk is meant to determine the contribution of each modified nucleotide for high affinity binding Modified nucleotides not required for high affinity binding could potentially be substituted by a non-modified base or deleted. In this table, "P" denotes NapdU while A, T, C, and G denote the naturally occurring deoxyribonucleotides and "NB" denotes no binding up to 100 nM human C3-Protein. The results of this walk are shown in Table 4. Substitution for the first seven modified (the seven closest to the 5'-terminus) nucleotides decreased affinity for C3-Protein relative to the 50-mer without any substitutions. Substitution of the NapdU closest to the 3'-terminus did not significantly impact binding.

TABLE 3

Deoxythymidine (T) substitutions for NapdU modified bases (P) in the 50-mer 8491-94_3 (SEQ ID NO: 5). All sequences contain a 3'-3' linked deoxythymidine at the 3'-terminus (not shown).

| Aptamer ID. No. | Sequence (5'→3') | $K_d$ (M) | SEQ ID NO. |
|---|---|---|---|
| 8491-94_11 | A-C-T-C-C-C-G-G-T-G-A-C-P-C-A-A-P-A-G-P-C-C-G-P-A-C-G-P-P-C-C-C-G-G-P-C-C-G-A-A-C-G-C-G-G-A-G-G-A | 2.95e-08 | 32 |
| 8491-94_12 | A-C-T-C-C-C-G-G-P-G-A-C-T-C-A-A-P-A-G-P-C-C-G-P-A-C-G-P-P-C-C-C-G-G-P-C-C-G-A-A-C-G-C-G-G-A-G-G-A | 8.57e-09 | 33 |
| 8491-94_13 | A-C-T-C-C-C-G-G-P-G-A-C-P-C-A-A-T-A-G-P-C-C-G-P-A-C-G-P-P-C-C-C-G-G-P-C-C-G-A-A-C-G-C-G-G-A-G-G-A | 4.17e-08 | 34 |
| 8491-94_14 | A-C-T-C-C-C-G-G-P-G-A-C-P-C-A-A-P-A-G-T-C-C-G-P-A-C-G-P-P-C-C-C-G-G-P-C-C-G-A-A-C-G-C-G-G-A-G-G-A | 1.00e-06 | 35 |
| 8491-94_15 | A-C-T-C-C-C-G-G-P-G-A-C-P-C-A-A-P-A-G-P-C-C-G-T-A-C-G-P-P-C-C-C-G-G-P-C-C-G-A-A-C-G-C-G-G-A-G-G-A | 1.00e-06 | 36 |
| 8491-94_16 | A-C-T-C-C-C-G-G-P-G-A-C-P-C-A-A-P-A-G-P-C-C-G-P-A-C-G-T-P-C-C-C-G-G-P-C-C-G-A-A-C-G-C-G-G-A-G-G-A | 6.94e-08 | 37 |
| 8491-94_17 | A-C-T-C-C-C-G-G-P-G-A-C-P-C-A-A-P-A-G-P-C-C-G-P-A-C-G-P-T-C-C-C-G-G-P-C-C-G-A-A-C-G-C-G-G-A-G-G-A | 2.88e-09 | 38 |
| 8491-94_18 | A-C-T-C-C-C-G-G-P-G-A-C-P-C-A-A-P-A-G-P-C-C-G-P-A-C-G-P-P-C-C-C-G-G-T-C-C-G-A-A-C-G-C-G-G-A-G-G-A | 4.21e-11 | 39 |

Truncation of the 50-mer 8491-94_3 (SEQ ID NO: 5).

Sequence 8491-94_3 (SEQ ID NO: 5) was chosen for post-SELEX modification and analysis, and has been truncated to the 28-mer 8491-94_53 (SEQ ID NO: 58) in a series of deletion experiments (Table 4). The truncated sequence maintains high affinity for human C3-Protein and still contains the 23 nucleotide consensus motif as described above. The modified nucleotide that did not contribute significantly to high affinity binding as shown above is removed in this 28-mer. Representative truncations were also tested for their ability to inhibit C3-protein in the hemolytic assay performed with C3-depleted human sera fortified with 20 nM (final concentration) C3-Protein (FIG. 5). 8491-94_26 (SEQ ID NO: 54), 8491-94_27 (SEQ ID NO: 55), and 8491-94_53 (SEQ ID NO: 58) were able to inhibit hemolysis with $IC_{50}$ values of 15.1 nM 24.6 nM and 17.1 nM, respectively. The 28-mer truncate, 8491-94_53 (SEQ ID NO: 58), was also shown to inhibit C3a release in 34% normal human serum with an $IC_{50}$ of 1.5 μM (FIG. 6).

TABLE 4

Truncations of the 50-mer sequence 8491-94_3 (SEQ ID NO: 5). All sequences contain a 3'-3' linked deoxythymidine at the 3'-terminus (not shown).

| Aptamer ID. No. | Sequence (5'→3') | $K_d$ | SEQ ID NO. |
|---|---|---|---|
| 8491-94_4 | A-C-T-C-C-C-G-G-P-G-A-C-P-C-A-A-P-A-G-P-C-C-G-P-A-C-G-P-P-C-C-C-G-G-P-C-C-G-A-A-C-G-C-G-G-A | 2.91e-11 | 40 |
| 8491-94_5 | A-C-T-C-C-C-G-G-P-G-A-C-P-C-A-A-P-A-G-P-C-C-G-P-A-C-G-P-P-C-C-C-G-G-P-C-C-G-A-A-C-G-C | 2.98e-11 | 41 |
| 8491-94_6 | A-C-T-C-C-C-G-G-P-G-A-C-P-C-A-A-P-A-G-P-C-C-G-P-A-C-G-P-P-C-C-C-G-G-P-C-C-G-A-A | 1.90e-11 | 42 |
| 8491-94_7 | A-C-T-C-C-C-G-G-P-G-A-C-P-C-A-A-P-A-G-P-C-C-G-P-A-C-G-P-P-C-C-C-G-G-P-C-C | 1.94e-11 | 43 |
| 8491-94_8 | C-C-C-G-G-P-G-A-C-P-C-A-A-P-A-G-P-C-C-G-P-A-C-G-P-P-C-C-C-G-G-P-C-C-G-A-A-C-G-C-G-G-A-G-G-A | 3.69e-11 | 44 |
| 8491-94_9 | C-G-G-P-G-A-C-P-C-A-A-P-A-G-P-C-C-G-P-A-C-G-P-P-C-C-C-G-G-P-C-C-G-A-A-C-G-C-G-G-A-G-G-A | 2.43e-10 | 45 |

TABLE 4-continued

Truncations of the 50-mer sequence 8491-94_3 (SEQ ID NO: 5). All sequences contain a 3'-3' linked deoxythymidine at the 3'-terminus (not shown).

| Aptamer ID. No. | Sequence (5'→3') | $K_d$ | SEQ ID NO. |
|---|---|---|---|
| 8491-94_10 | P-G-A-C-P-C-A-A-P-A-G-P-C-C-G-P-A-C-G-P-P-C-C-C-G-G-P-C-C-G-A-A-C-G-C-G-G-A-G-G-A | 7.60e-09 | 46 |
| 8491-94_19 | A-C-T-C-C-C-C-G-G-P-G-A-C-P-C-A-A-P-A-G-P-C-C-G-P-A-C-G-P-P-C-C-C-G-G | 5.59E-11 | 47 |
| 8491-94_20 | A-C-T-C-C-C-C-G-G-P-G-A-C-P-C-A-A-P-A-G-P-C-C-G-P-A-C-G-P-P-C-C | 1.14e-09 | 48 |
| 8491-94_21 | A-C-T-C-C-C-C-G-G-P-G-A-C-P-C-A-A-P-A-G-P-C-C-G-P-A-C-G-P-P | 2.49e-10 | 49 |
| 8491-94_22 | C-C-C-G-G-P-G-A-C-P-C-A-A-P-A-G-P-C-C-G-P-A-C-G-P-P-C-C-C-G-G-P-C-C-G-A-A-C-G-C-G-G-A-G-G-A | 1.03e-10 | 50 |
| 8491-94_23 | C-C-G-G-P-G-A-C-P-C-A-A-P-A-G-P-C-C-G-P-A-C-G-P-P-C-C-C-G-G-P-C-C-G-A-A-C-G-C-G-G-A-G-G-A | 6.21e-11 | 51 |
| 8491-94_24 | C-C-C-C-G-G-P-G-A-C-P-C-A-A-P-A-G-P-C-C-G-P-A-C-G-P-P-C-C-C-G-G-P-C-C | 5.35e-11 | 52 |
| 8491-94_25 | C-C-C-C-G-G-P-G-A-C-P-C-A-A-P-A-G-P-C-C-G-P-A-C-G-P-P-C-C-C-G-G | 9.28e-11 | 53 |
| 8491-94_26 | C-C-G-G-P-G-A-C-P-C-A-A-P-A-G-P-C-C-G-P-A-C-G-P-P-C-C-C-G-G | 5.11e-11 | 54 |
| 8491-94_27 | C-C-G-G-P-G-A-C-P-C-A-A-P-A-G-P-C-C-G-P-A-C-G-P-P-C-C-C-G | 6.58e-11 | 55 |
| 8491-94_28 | C-C-G-G-P-G-A-C-P-C-A-A-P-A-G-P-C-C-G-P-A-C-G-P-P-C-C-C | 2.65e-10 | 56 |
| 8491-94_29 | C-G-G-P-G-A-C-P-C-A-A-P-A-G-P-C-C-G-P-A-C-G-P-P-C-C-C-G-G | 5.81e-11 | 57 |
| 8491-94_53 | C-G-G-P-G-A-C-P-C-A-A-P-A-G-P-C-C-G-P-A-C-G-P-P-C-C-C-G | 3.34e-11 | 58 |
| 8491-94_87 | C-G-G-P-G-A-C-P-C-A-A-P-A-G-P-C-C-G-P-A-C-G-P-P-C-C-G | 1.54e-10 | 59 |

C3-Spacer Single Substitutions in 8491-94_26 (SEQ ID NO: 54).

The first Round of post-SELEX modifications of the C3 aptamer was a C3-Spacer walk at all positions in the 30-mer 8491-94_26 (SEQ ID NO: 54)) except for those positions containing a NapdU. The C3-Spacer walk is meant to identify bases not required for high affinity binding that could potentially be removed altogether, replaced with a 3-carbon spacer (C3-Spacer) or other linkers such as hexaethylene glycol (Heg) or polyethylene glycol (PEG) linkers. The results for the C3-Spacer substitutions are shown in Table 5. In this table, "P" denotes NapdU, "C3" denotes C3-Spacer; A, C, and G denote the naturally occurring deoxyribonucleotides and "NB" denotes no binding up to 100 nM C3-Protein. Several sites tolerated a C3-Spacer substitution. Substitution of a C3-Spacer at three internal position showed enhanced binding to C3-Protein compared to 8491-94_26 (SEQ ID NO: 54). These were positions 8, 18, and 26 relative to the 5'-terminus of 8491-94_26 (SEQ ID NO: 54). Substitution at position 8 created aptamer 8491-94_36 (SEQ ID NO: 66) which bound to C3-Protein with an affinity dissociation constant ($K_d$) of 31.5 pM while substitution at position 18 or 26 created aptamers 8491-94_43 (SEQ ID NO: 73) and [8491-94_48 (SEQ ID NO: 78)], respectively, which bound to C3-Protein with $K_d$ values of 14.2 pM and 30.2 pM, respectively.

A single Heg or C3-Spacer ("C3") substitution or multiple C3-Spacer substitutions were made at the equivalent position in the 28-mer aptamer 8491-94_53 (Table 6). Of note, substitution of three C3-Spacer groups at positions 7, 17 and 25 (numbering relative to the 5'-terminus of 8491-94_53) lead to an aptamer with a $K_d$ of 22.1 pM compared to 33.4 pM for 8491-94_53 (SEQ ID NO: 58).

Individual sequences containing C3-Spacer groups maintained the ability to inhibit C3-Protein in the hemolysis assay (FIG. 5). Sequences 8491-94_30 (SEQ ID NO: 60), 8491-94_36 (SEQ ID NO: 66), 8491-94_37 (SEQ ID NO: 67) and 8491-94_43 (SEQ ID NO: 73) were able to inhibit hemolysis in this assay with $IC_{50}$ values of 20.9 nM 25.0 nM, 24.7, and 19.2 nM, respectively.

TABLE 5

C3-Spacer substitutions in the 30-mer 8491-94_26 (SEQ ID NO: 54). All sequences contain a 3'-3' linked deoxythymidine at the 3'-terminus (not shown).

| Aptamer ID. No. | Sequence (5'→3') | $K_d$ (M) | SEQ ID NO. |
|---|---|---|---|
| 8491-94_30 | C3-C-G-G-P-G-A-C-P-C-A-A-P-A-G-P-C-C-G-P-A-C-G-P-P-C-C-C-G-G | 6.22e-11 | 60 |
| 8491-94_31 | C-C3-G-G-P-G-A-C-P-C-A-A-P-A-G-P-C-C-G-P-A-C-G-P-P-C-C-C-G-G | 1.4e-10 | 61 |
| 8491-94_32 | C-C-C3-G-P-G-A-C-P-C-A-A-P-A-G-P-C-C-G-P-A-C-G-P-P-C-C-C-G-G | 7.8e-10 | 62 |
| 8491-94_33 | C-C-G-C3-P-G-A-C-P-C-A-A-P-A-G-P-C-C-G-P-A-C-G-P-P-C-C-C-G-G | 2.45e-10 | 63 |
| 8491-94_34 | C-C-G-G-P-C3-A-C-P-C-A-A-P-A-G-P-C-C-G-P-A-C-G-P-P-C-C-C-G-G | 1.41e-8 | 64 |
| 8491-94_35 | C-C-G-G-P-G-C3-C-P-C-A-A-P-A-G-P-C-C-G-P-A-C-G-P-P-C-C-C-G-G | 5.67e-9 | 65 |
| 8491-94_36 | C-C-G-G-P-G-A-C3-P-C-A-A-P-A-G-P-C-C-G-P-A-C-G-P-P-C-C-C-G-G | 3.15e-11 | 66 |
| 8491-94_37 | C-C-G-G-P-G-A-C-P-C3-A-A-P-A-G-P-C-C-G-P-A-C-G-P-P-C-C-C-G-G | 9.22e-11 | 67 |
| 8491-94_38 | C-C-G-G-P-G-A-C-P-C-C3-A-P-A-G-P-C-C-G-P-A-C-G-P-P-C-C-C-G-G | 1.48e-10 | 68 |
| 8491-94_39 | C-C-G-G-P-G-A-C-P-C-A-C3-P-A-G-P-C-C-G-P-A-C-G-P-P-C-C-C-G-G | 3.10e-10 | 69 |
| 8491-94_40 | C-C-G-G-P-G-A-C-P-C-A-A-P-C3-G-P-C-C-G-P-A-C-G-P-P-C-C-C-G-G | 1.99e-9 | 70 |
| 8491-94_41 | C-C-G-G-P-G-A-C-P-C-A-A-P-A-C3-P-C-C-G-P-A-C-G-P-P-C-C-C-G-G | 5.98e-10 | 71 |
| 8491-94_42 | C-C-G-G-P-G-A-C-P-C-A-A-P-A-G-P-C3-C-G-P-A-C-G-P-P-C-C-C-G-G | 8.60e-10 | 72 |
| 8491-94_43 | C-C-G-G-P-G-A-C-P-C-A-A-P-A-G-P-C-C3-G-P-A-C-G-P-P-C-C-C-G-G | 1.42e-11 | 73 |
| 8491-94_44 | C-C-G-G-P-G-A-C-P-C-A-A-P-A-G-P-C-C-C3-P-A-C-G-P-P-C-C-C-G-G | 1.28e-9 | 74 |
| 8491-94_45 | C-C-G-G-P-G-A-C-P-C-A-A-P-A-G-P-C-C-G-P-C3-C-G-P-P-C-C-C-G-G | 2.28e-7 | 75 |
| 8491-94_46 | C-C-G-G-P-G-A-C-P-C-A-A-P-A-G-P-C-C-G-P-A-C3-G-P-P-C-C-C-G-G | NB | 76 |
| 8491-94_47 | C-C-G-G-P-G-A-C-P-C-A-A-P-A-G-P-C-C-G-P-A-C-C3-P-P-C-C-C-G-G | NB | 77 |
| 8491-94_48 | C-C-G-G-P-G-A-C-P-C-A-A-P-A-G-P-C-C-G-P-A-C-G-P-P-C3-C-C-G-G | 3.02e-11 | 78 |
| 8491-94_49 | C-C-G-G-P-G-A-C-P-C-A-A-P-A-G-P-C-C-G-P-A-C-G-P-P-P-C-C3-C-G-G | 2.66e-10 | 79 |
| 8491-94_50 | C-C-G-G-P-G-A-C-P-C-A-A-P-A-G-P-C-C-G-P-A-C-G-P-P-P-C-C-C3-G-G | 4.48e-10 | 80 |
| 8491-94_51 | C-C-G-G-P-G-A-C-P-C-A-A-P-A-G-P-C-C-G-P-A-C-G-P-P-P-C-C-C-C3-G | 2.27e-10 | 81 |
| 8491-94_52 | C-C-G-G-P-G-A-C-P-C-A-A-P-A-G-P-C-C-G-P-A-C-G-P-P-P-C-C-C-G-C3 | 5.04e-11 | 82 |

TABLE 6

C3-Spacer and hexaethylene glycol (Heg) spacer substitutions in the 28-mer 8491-94_53. All sequences contain a 3'-3' linked deoxythymidine at the 3'-terminus (not shown).

| Aptamer ID. No. | Sequence (5'→3') | $K_d$ (M) | SEQ ID NO. |
| --- | --- | --- | --- |
| 8491-94_54 | C-G-G-P-G-A-C3-P-C-A-A-P-A-G-P-C-C3-G-P-A-C-G-P-P-C3-C-C-G | 2.21E-11 | 83 |
| 8491-94_55 | C-G-G-P-G-A-C3-P-C3-A-A-P-A-G-P-C-C3-G-P-A-C-G-P-P-C3-C-C-G | 4.15E-11 | 84 |
| 8491-94_56 | C-G-G-P-G-A-C-P-C-A-A-P-A-G-P-C-C3-G-P-A-C-G-P-P-C3-C-C-G | 4.64E-11 | 85 |
| 8491-94_57 | C-G-G-P-G-A-C-P-Heg-P-A-G-P-C-C-G-P-A-C-G-P-P-C-C-C-G | 2.45E-10 | 86 |
| 8491-94_58 | C-G-G-P-G-A-C-P-C-A-A-P-A-G-P-C-C3-G-P-A-C-G-P-P-C-C-C-G | 7.87E-10 | 87 |

2'-O-Methyl Single Substitutions in 8491-94_53 (SEQ ID NO: 58).

To enhance the nuclease resistance of the truncated NapdU-containing Slow Off Rate Modified Aptamer (SOMAmer) 8491-94_53 (SEQ ID NO: 58), 2'-O-methyl (2'-OMe) groups were incorporated at nucleotide positions in which binding to C3-Protein was not significantly affected. The effect on protein binding of any individual 2'-OMe addition is not predictable a priori. Therefore, a "2'-OMe walk" was performed in which several variants of aptamer 8491-94_53 (SEQ ID NO: 58) were created in which each variant contained only a single modified nucleotide. The binding affinity of each variant was determined (Sequence ID Numbers 88 through 115).

2'-O-methyl substitutions were made in order to identify positions that could tolerate this nuclease-resistant substitution. The sequences and the binding affinities of each construct are shown in Table 7. In this table a superscript 1 ([1]) demotes a nucleotide with a 2'-O-methyl substitution, a "P" denotes NapdU, an "A", "C" and "G" denote the naturally occurring nucleobases and "NB" denotes no binding up to 100 nM human C3-Protein. A substitution could be made in 18 positions while maintaining a $K_d$ below 100 pM.

TABLE 7

2'-O-methyl and deoxythymidine substitutions in 28-mer 8491-94_53 (SEQ ID NO: 58). All sequences contain a 3'-3' linked deoxythymidine at the 3'-terminus (not shown).

| Aptamer ID. No. | Sequence (5'→3') | $K_d$ (M) | SEQ ID NO. |
| --- | --- | --- | --- |
| 8491-94_59 | C[1]-G-G-P-G-A-C-P-C-A-A-P-A-G-P-C-C-G-P-A-C-G-P-P-C-C-C-G | 3.42e-11 | 88 |
| 8491-94_60 | C-G[1]-G-P-G-A-C-P-C-A-A-P-A-G-P-C-C-G-P-A-C-G-P-P-C-C-C-G | 5.37e-11 | 89 |
| 8491-94_61 | C-G-G[1]-P-G-A-C-P-C-A-A-P-A-G-P-C-C-G-P-A-C-G-P-P-C-C-C-G | 2.37e-11 | 90 |
| 8491-94_62 | C-G-G-P[1]-G-A-C-P-C-A-A-P-A-G-P-C-C-G-P-A-C-G-P-P-C-C-C-G | 9.18e-11 | 91 |
| 8491-94_63 | C-G-G-P-G[1]-A-C-P-C-A-A-P-A-G-P-C-C-G-P-A-C-G-P-P-C-C-C-G | 2.68e-11 | 92 |
| 8491-94_64 | C-G-G-P-G-A[1]-C-P-C-A-A-P-A-G-P-C-C-G-P-A-C-G-P-P-C-C-C-G | 5.12e-10 | 93 |
| 8491-94_65 | C-G-G-P-G-A-C[1]-P-C-A-A-P-A-G-P-C-C-G-P-A-C-G-P-P-C-C-C-G | 3.16e-11 | 94 |
| 8491-94_66 | C-G-G-P-G-A-C-P[1]-C-A-A-P-A-G-P-C-C-G-P-A-C-G-P-P-C-C-C-G | 1.49e-10 | 95 |
| 8491-94_67 | C-G-G-P-G-A-C-P-C[1]-A-A-P-A-G-P-C-C-G-P-A-C-G-P-P-C-C-C-G | 6.99e-11 | 96 |
| 8491-94_68 | C-G-G-P-G-A-C-P-C-A[1]-A-P-A-G-P-C-C-G-P-A-C-G-P-P-C-C-C-G | 4.24e-11 | 97 |

TABLE 7-continued

2'-O-methyl and deoxythymidine substitutions in 28-mer 8491-94_53 (SEQ ID NO: 58). All sequences contain a 3'-3' linked deoxythymidine at the 3'-terminus (not shown).

| Aptamer ID. No. | Sequence (5'→3') | $K_d$ (M) | SEQ ID NO. |
|---|---|---|---|
| 8491-94_69 | C-G-G-P-G-A-C-P-C-A-A$^1$-P-A-G-P-C-C-G-P-A-C-G-P-P-C-C-C-G | 2.72e-10 | 98 |
| 8491-94_70 | C-G-G-P-G-A-C-P-C-A-A-P$^1$-A-G-P-C-C-G-P-A-C-G-P-P-C-C-C-G | 3.38e-10 | 99 |
| 8491-94_71 | C-G-G-P-G-A-C-P-C-A-A-P-A$^1$-G-P-C-C-G-P-A-C-G-P-P-C-C-C-G | 2.56e-11 | 100 |
| 8491-94_72 | C-G-G-P-G-A-C-P-C-A-A-P-A-G$^1$-P-C-C-G-P-A-C-G-P-P-C-C-C-G | 6.17e-09 | 101 |
| 8491-94_73 | C-G-G-P-G-A-C-P-C-A-A-P-A-G-P$^1$-C-C-G-P-A-C-G-P-P-C-C-C-G | 1.32e-09 | 102 |
| 8491-94_74 | C-G-G-P-G-A-C-P-C-A-A-P-A-G-P-C$^1$-C-G-P-A-C-G-P-P-C-C-C-G | 1.92e-10 | 103 |
| 8491-94_75 | C-G-G-P-G-A-C-P-C-A-A-P-A-G-P-C-C$^1$-G-P-A-C-G-P-P-C-C-C-G | 2.14e-10 | 104 |
| 8491-94_76 | C-G-G-P-G-A-C-P-C-A-A-P-A-G-P-C-C-G$^1$-P-A-C-G-P-P-C-C-C-G | 9.30e-10 | 105 |
| 8491-94_77 | C-G-G-P-G-A-C-P-C-A-A-P-A-G-P-C-C-G-P$^1$-A-C-G-P-P-C-C-C-G | 2.62e-11 | 106 |
| 8491-94_78 | C-G-G-P-G-A-C-P-C-A-A-P-A-G-P-C-C-G-P-A$^1$-C-G-P-P-C-C-C-G | 7.18e-11 | 107 |
| 8491-94_79 | C-G-G-P-G-A-C-P-C-A-A-P-A-G-P-C-C-G-P-A-C$^1$-G-P-P-C-C-C-G | 2.73e-10 | 108 |
| 8491-94_80 | C-G-G-P-G-A-C-P-C-A-A-P-A-G-P-C-C-G-P-A-C-G$^1$-P-P-C-C-C-G | 6.78e-11 | 109 |
| 8491-94_81 | C-G-G-P-G-A-C-P-C-A-A-P-A-G-P-C-C-G-P-A-C-G-P$^1$-P-C-C-C-G | 2.43e-11 | 110 |
| 8491-94_82 | C-G-G-P-G-A-C-P-C-A-A-P-A-G-P-C-C-G-P-A-C-G-P-P$^1$-C-C-C-G | 1.18e-11 | 111 |
| 8491-94_83 | C-G-G-P-G-A-C-P-C-A-A-P-A-G-P-C-C-G-P-A-C-G-P-P-C$^1$-C-C-G | 4.88e-11 | 112 |
| 8491-94_84 | C-G-G-P-G-A-C-P-C-A-A-P-A-G-P-C-C-G-P-A-C-G-P-P-C-C$^1$-C-G | 7.38e-11 | 113 |
| 8491-94_85 | C-G-G-P-G-A-C-P-C-A-A-P-A-G-P-C-C-G-P-A-C-G-P-P-C-C-C$^1$-G | 5.24e-11 | 114 |
| 8491-94_86 | C-G-G-P-G-A-C-P-C-A-A-P-A-G-P-C-C-G-P-A-C-G-P-P-C-C-C-G$^1$ | 3.44e-11 | 115 |

Multiple 2'-O-Methyl Substitutions or Multiple 2'-O-Methyl Substitutions with C3-Spacer Substitutions in 8491-94_53 (SEQ ID NO: 58).

In order to maximize resistance to nucleases, aptamers with multiple 2'-O-methyl substitutions are desired. The addition of C3-Spacer or Heg moieties in combination with multiple 2'-O-methyl substitutions may potentially further increase nuclease stability. Based upon the binding information of the 2'-OMe walk above, a number of aptamers were created in which several 2'-OMe additions were incorporated within each aptamer with or without the simultaneous substitution of C3-Spacers or Heg moieties for cytosine nucleotides previously identified to allow such substitution (Sequence ID Numbers 116 through 130). In addition, base substitutions at certain positions were explored in combination with several 2'-OMe substitutions with or without the simultaneous substitution of a C3-Spacer (Sequence ID Numbers 138 through 151). The sequences constructed and the associated binding affinity is shown in Table 8. In this table a superscript 1 ($^1$) demotes a nucleotide with a 2'-O-methyl substitution, a "P" denotes NapdU, a "C3" denotes a 3-carbon spacer, a "Heg" denotes a hexaethylene glycol, "A", "C", "T", "U", and "G" denote the naturally occurring nucleobases, and "NB" denotes no binding up to 100 nM human C3-Protein. Not all combinations maintained high affinity binding. For example 8491-94_91 (SEQ ID NO: 119) 8491-94_92 (SEQ ID NO: 120), and 8491-94_126 (SEQ ID NO: 138) showed no discernible binding activity.

However, other combinations including 8491-94_97 (SEQ ID NO: 125), which contains seventeen 2'-O-methyl nucleotides, still maintains high affinity binding to human C3-Protein. Representative sequences were tested for their ability to inhibit C3-Protein in the hemolysis assay (FIG. 5b). Aptamers 8491-94_90 (SEQ ID NO: 118), 8491-94_97 (SEQ ID NO: 125) and 8491-94_100 (SEQ ID NO: 128) inhibit with $IC_{50}$ values of 18.9 nM, 15.6 nM, and 19.7 nM, respectively. In addition, aptamer 8491-94_97 (SEQ ID NO: 125) is shown to inhibit C3a release in 34% normal human serum with an $IC_{50}$ value of 3 μM (FIG. 6).

TABLE 8

Multiple 2'-O-methyl substitutions or multiple 2'-O-methyl substitutions with or without C3-Spacer and/or nucleotide substitutions in 28-mer aptamer 8491-94_53 (SEQ ID NO: 58). All sequences contain a 3'-3' linked deoxythymidine at the 3'-terminus (not shown).

| Aptamer ID. No. | Sequence (5'→3') | $K_d$ (M) | SEQ ID NO. |
|---|---|---|---|
| 8491-94_88 | $C^1$-G-G1-P-$G^1$-A-$C^1$-P-C-A-A-P-$A^1$-G-P-C-C-G-P-A-C-G-P-P-C-C-C-$G^1$ | 2.48E-11 | 116 |
| 8491-94_89 | $C^1$-G-$G^1$-P-$G^1$-A-C1-P-C-$A^1$-A-P-$A^1$-G-P-C-C-G-P-A-C-G-P-P-C-C-C-$G^1$ | 1.73E-11 | 117 |
| 8491-94_90 | $C^1$-$G^1$-$G^1$-P-$G^1$-A-$C^1$-P-C-$A^1$-A-P-$A^1$-G-P-C-C-G-P-A-C-G-P-P-C-$C^1$-$C^1$-$G^1$ | 4.24E-12 | 118 |
| 8491-94_91 | $C^1$-G-$G^1$-P-$G^1$-A-$C^1$-P-C-$A^1$-A-P-$A^1$-G-P-C-C-G-$P^1$-A-C-G-$P^1$-$P^1$-C-C-C-$G^1$ | NB | 119 |
| 8491-94_92 | $C^1$-G-$G^1$-P-$G^1$-A-$C^1$-P-C-$A^1$-A-P-$A^1$-G-P-C-C-G-$P^1$-A-C-G-$P^1$-$P^1$-$C^1$-C-C-$G^1$ | NB | 120 |
| 8491-94_93 | $C^1$-$G^1$-$G^1$-P-$G^1$-A-$C^1$-P-C-$A^1$-A-P-$A^1$-G-P-C-C-G-$P^1$-A-C-G-$P^1$-$P^1$-C-$C^1$-$C^1$-$G^1$ | 1.52e-11 | 121 |
| 8491-94_94 | $C^1$-$G^1$-$G^1$-P-$G^1$-A-$C^1$-P-C-$A^1$-A-P-$A^1$-G-P-C-C-G-$P^1$-A-C-G-$P^1$-$P^1$-$C^1$-$C^1$-$C^1$-$G^1$ | 5.57e-11 | 122 |
| 8491-94_95 | $C^1$-$G^1$-$G^1$-P-$G^1$-A-$C^1$-P-C-$A^1$-A-P-$A^1$-G-P-C-C-G-$P^1$-$A^1$-C-G-$P^1$-$P^1$-$C^1$-$C^1$-$C^1$-$G^1$ | 3.57e-11 | 123 |
| 8491-94_96 | $C^1$-$G^1$-$G^1$-P-$G^1$-A-$C^1$-P-$C^1$-$A^1$-A-P-$A^1$-G-P-C-C-G-$P^1$-$A^1$-C-G-$P^1$-$P^1$-$C^1$-$C^1$-$C^1$-$G^1$ | 3.64e-11 | 124 |
| 8491-94_97 | $C^1$-$G^1$-$G^1$-P-$G^1$-A-$C^1$-P-$C^1$-$A^1$-A-P-$A^1$-G-P-C-C-G-$P^1$-$A^1$-C-$G^1$-$P^1$-$P^1$-$C^1$-$C^1$-$C^1$-$G^1$ | 5.49e-11 | 125 |
| 8491-94_98 | $C^1$-$G^1$-$G^1$-P-$G^1$-A-$C^1$-P-$C^1$-$A^1$-A-P-$A^1$-G-P-C-C-C3-G-$P^1$-$A^1$-C-$G^1$-$P^1$-$P^1$-$C^1$-$C^1$-$C^1$-$G^1$ | 9.50e-11 | 126 |
| 8491-94_99 | $C^1$-$G^1$-$G^1$-P-$G^1$-A-C1-P-C1-$A^1$-A-P-$A^1$-G-P-C-C3-G-$P^1$-$A^1$-C-$G^1$-$P^1$-$P^1$-C3-$C^1$-$C^1$-$G^1$ | 1.67e-10 | 127 |
| 8491-94_100 | $C^1$-$G^1$-$G^1$-P-$G^1$-A-C3-P-$C^1$-$A^1$-A-P-$A^1$-G-P-C-C3-G-$P^1$-$A^1$-C-$G^1$-$P^1$-$P^1$-C3-$C^1$-$C^1$-$G^1$ | 7.94e-11 | 128 |
| 8491-94_101 | $C^1$-$G^1$-$G^1$-P-$G^1$-A-$C^1$-P-$C^1$-$A^1$-A-P-$A^1$-G-P-C-C-G-P-$A^1$-C-$G^1$-P-P-$C^1$-$C^1$-$C^1$-$G^1$ | 2.19e-10 | 129 |
| 8491-94_102 | $C^1$-$G^1$-$G^1$-P-$G^1$-A-C3-P-C-$A^1$-A-P-$A^1$-G-P-C-C3-G-P-A-C-G-P-P-C3-$C^1$-$C^1$-$G^1$ | 6.03e-11 | 130 |
| 8491-94_126 | $C^1$-A-$G^1$-P-$G^1$-A-$C^1$-P-$C^1$-$A^1$A-P-$A^1$-G-P-C-C-A-$P^1$-$A^1$-C-A-$P^1$-$P^1$-$C^1$-$C^1$-$C^1$-A | NB | 138 |
| 8491-94_127 | $G^1$-$G^1$-$G^1$-P-$G^1$-A-$C^1$P-$C^1$-$A^1$-A-P-$A^1$-G-P-C-C-G-$P^1$-$A^1$-C-$G^1$-$P^1$-$P^1$-$C^1$-$C^1$-$C^1$-$C^1$ | 4.5e-11 | 139 |
| 8491-94_128 | T-$G^1$-$G^1$-P-$G^1$-A-$C^1$-P-$C^1$-$A^1$-A-P-$A^1$-G-P-C-C-G-$P^1$-$A^1$-C-$G^1$-$P^1$-$P^1$-$C^1$-$C^1$-$C^1$-$A^1$ | 3.8e-11 | 140 |
| 8491-94_129 | T-$G^1$-$G^1$-P-$G^1$-A-$C^1$-P-$C^1$-$A^1$-A-P-$A^1$-G-P-C-C3-G-$P^1$-$A^1$-C-$G^1$-$P^1$-$P^1$-$C^1$-$C^1$-$C^1$-$A^1$ | 1.79e-11 | 141 |
| 8491-94_130 | T-$G^1$-$G^1$-P-$G^1$-A-$C^1$-P-$C^1$-$A^1$-A-P-$A^1$-G-P-C-C-G-$P^1$-$A^1$-T-$G^1$-$P^1$-$P^1$-$C^1$-$C^1$-$C^1$-$A^1$ | 1.79e-08 | 142 |
| 8491-94_131 | T-$G^1$-$G^1$-P-$G^1$-A-$C^1$-P-$C^1$-$A^1$-A-P-$A^1$-G-P-C-C3-G-$P^1$-$A^1$-T-$G^1$-$P^1$-$P^1$-$C^1$-$C^1$-$C^1$-$A^1$ | 5.64e-09 | 143 |

TABLE 8-continued

Multiple 2'-O-methyl substitutions or multiple 2'-O-methyl substitutions with or without C3-Spacer and/or nucleotide substitutions in 28-mer aptamer 8491-94_53 (SEQ ID NO: 58). All sequences contain a 3'-3' linked deoxythymidine at the 3'-terminus (not shown).

| Aptamer ID. No. | Sequence (5'→3') | $K_d$ (M) | SEQ ID NO. |
|---|---|---|---|
| 8491-94_132 | C¹-G¹-G¹-P-G¹-A-C¹-P-C¹-A¹-A-P-A¹-G-P-C-C-G-P¹-A¹-T-G¹-P¹-P¹-C¹-C¹-C¹-G¹ | 1.27e-08 | 144 |
| 8491-94_133 | C¹-G¹-G¹-P-G¹-A-C¹-P-C¹-A¹-A-P-A¹-G-P-C-C3-G-P¹-A¹-T-G¹P¹-C¹-C¹-C¹-G¹ | 5.06e-09 | 145 |
| 8491-94_134 | G¹-G¹-G¹-P-G¹-A-C¹-P-C¹-A¹-A-P-A¹-G-P-C-C3-G-P¹-A¹-C-G¹-P¹-P¹-C¹-C¹-C¹-C¹ | 1.07e-10 | 146 |
| 8491-94_135 | G¹-G¹-G¹-P-G¹-A-C¹-P-C¹-A¹-A-P-A¹-G-P-C-C-G-P¹-A¹-C-A¹-P¹-P¹-C¹-C¹-C¹-C¹ | 1.53e-08 | 147 |
| 8491-94_136 | G¹-G¹-G¹-P-G¹-A-C¹-P-C¹-A¹-A-P-A¹-G-P-C-C3-G-P¹-A¹-C-A¹-P¹-P¹-C¹-C¹-C¹-C¹ | 9.10e-09 | 148 |
| 8491-94_137 | U¹-G¹-G¹-P-G¹-A-C¹-P-C¹-A¹-A-P-A¹-G-P-C-C3-G-P¹-A¹-C-G¹-P¹-P¹-C¹-C¹-C¹-A¹ | 1.19e-10 | 149 |
| 8491-94_138 | U¹-G¹-G¹-P-G¹-A-C¹-P-C¹-A¹-A-P-A¹-G-P-C-C3-G-P¹-A¹-C-A¹-P¹-P¹-C¹-C¹-C¹-A¹ | 1.82e-08 | 150 |
| 8491-94_139 | U¹-G¹-G¹-P-G¹-A-C¹-P-C¹-A¹-A-P-A¹-G-P-C-C-G-P¹-A¹-C-A¹-P¹-P¹-C¹-C¹-C¹-A1 | 2.67e-08 | 151 |

¹Nucleotide containing a 2'-OMe sugar.

Example 5

Determination of Aptamer Sensitivity to Digestion by DNase I or Dnase II

This example provides a summary of the general methods and materials used herein to determine the sensitivity of an aptamer to digestion by deoxyribonuclease I (DNase I) or deoxyribonuclease II (DNase II). For the DNase I aptamer stability assay polyacrylamide-gel-purified aptamers at a final concentration of 250 nM were incubated with 2 units/mL of recombinant human DNase I (CELL SCIENCES, Cat No. CSI10719) in nuclease buffer (10 mM Tris HCl pH 7.6, 2.5 mM MgCl$_2$, 0.5 mM CaCl$_2$) at 37° C. in a total reaction volume of 100 µL. At various times, a 15 µL aliquot was collected and the reaction stopped by adding an equal volume of 2× gel loading buffer (93.85% formamide, 0.2% SDS, 20 mM Na$_2$EDTA, 0.05% xylene cylanol and 0.1% Orange G) and heating at 95° C. for 2 minutes. Digestion products were separated from full-length aptamer by polyacrylamide gel electrophoresis using a 15% polyacrylamide denaturing gel (8 M urea). Electrophoresis was performed at 200 V for 20 minutes in a Tris borate buffer system. Gels were stained with approximately 2 µM SYBR® Gold (MOLECULAR PROBES, Cat No. S11494) for 10 minutes to visualize the bands. The amount of full-length aptamer remaining at each time point was quantified using FlourChem® Q analysis software (ALPHA INNOTECH). If necessary, the intensity of each band was determined following a background subtraction and data are presented as a percentage remaining of full-length input DNA at the zero time point. 5'-hydroxyl containing versions of aptamers with a 3'-3' linked dT "cap" were utilized for these experiments.

For the DNase II aptamer stability assay, polyacrylamide-gel-purified aptamers at a final concentration of 250 nM were incubated with 140 units/mL of porcine DNase II (WORTHINGTON BIOCHEMICAL CORPORATION) in nuclease buffer (0.1M NaOAc pH 4.6, 2.0 mM MgCl$_2$, 15 mM NaCl$_2$) at 37° C. in a total reaction volume of 100 µL. At various times, a 15 µL aliquot was collected and the reaction stopped by adding an equal volume of 2× gel loading buffer (93.85% formamide, 0.2% SDS, 20 mM Na$_2$EDTA, 0.05% xylene cylanol and 0.1% Orange G) and heating at 95° C. for 2 minutes. Digestion products were separated from full-length aptamer by polyacrylamide gel electrophoresis using a 15% polyacrylamide denaturing gel (8 M urea) and electrophoresis performed at 200 V for 20 minutes in a Tris borate EDTA buffer system. Gels were stained with approximately 2 µM SYBR® Gold (MOLECULAR PROBES, Cat No. S11494) for 10 minutes to visualize the bands. The amount of full-length aptamer remaining at each time point was quantified using FlourChem® Q analysis software (ALPHA INNOTECH). If necessary, the intensity of each band was determined following a background subtraction and data presented as a percentage remaining of full-length input DNA at the zero time point. 5'-hydroxyl containing versions of aptamers with a 3'-3' linked dT "cap" were utilized for these experiments.

Figure 7:
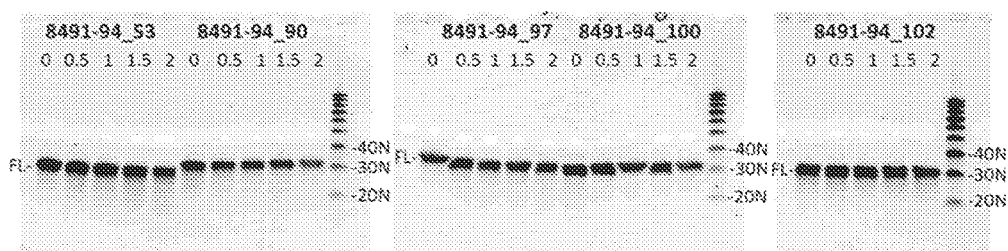
FIGS. 7A and 7B. Aptamers 8491-94_53 (SEQ ID NO: 58), 8491-94_90 (SEQ ID NO: 118), 8491-94_97 (SEQ ID NO: 125), 8491-94_100 (SEQ ID NO: 128) and 8491-94_102 (SEQ ID NO: 130) (250 nM) were digested at 37° C. for the indicated number of hours with 0.002 units/μL DNase I (A) as described in Example 5 and the digestion products separated by polyacrylamide gel electrophoresis. Bands were visualized with SYBR Gold. Size of the full-length (FL) aptamers and of selected molecular length markers where N is the number of nucleotides are as shown. (B) The percent remaining of each full-length aptamer band (SOMAmer) versus time as determined by densitometry. The prefix "OH" indicates an unmodified 5'-terminus.
Figure 7:
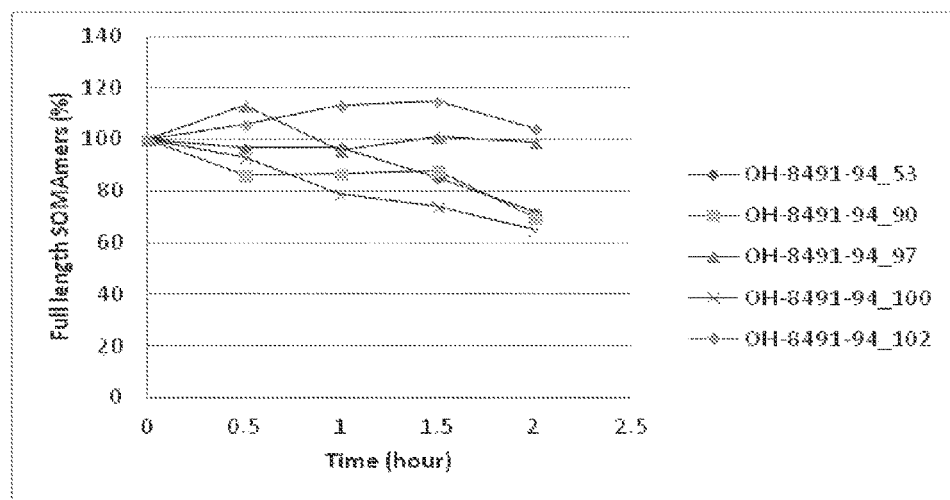
Figure 8:
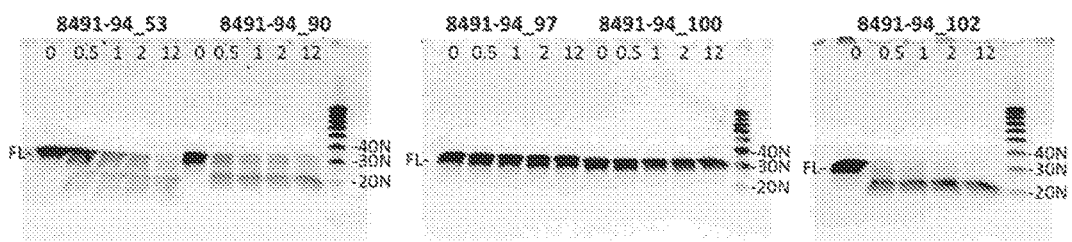
FIGS. 8A and 8B. Aptamers 8491-94_53 (SEQ ID NO: 58), 8491-94_90 (SEQ ID NO: 118), 8491-94_97 (SEQ ID NO: 125), 8491-94_100 (SEQ ID NO: 128) and 8491-94_102 (SEQ ID NO: 130) were digested at 37° C. for the indicated number of hours with 0.014 units/μL DNase II as described in Example 5 and the digestion products separated by polyacrylamide gel electrophoresis. Digestion products were separated by polyacrylamide gel electrophoresis. Bands were visualized with SYBR Gold. Size of the full-length (FL) aptamers and of selected molecular length markers where N is the number of nucleotides are as shown. (B) The percent remaining of each full-length aptamer band (SOMAmer) versus time as determined by densitometry. The prefix "OH" indicates an unmodified 5'-terminus.
Figure 8:
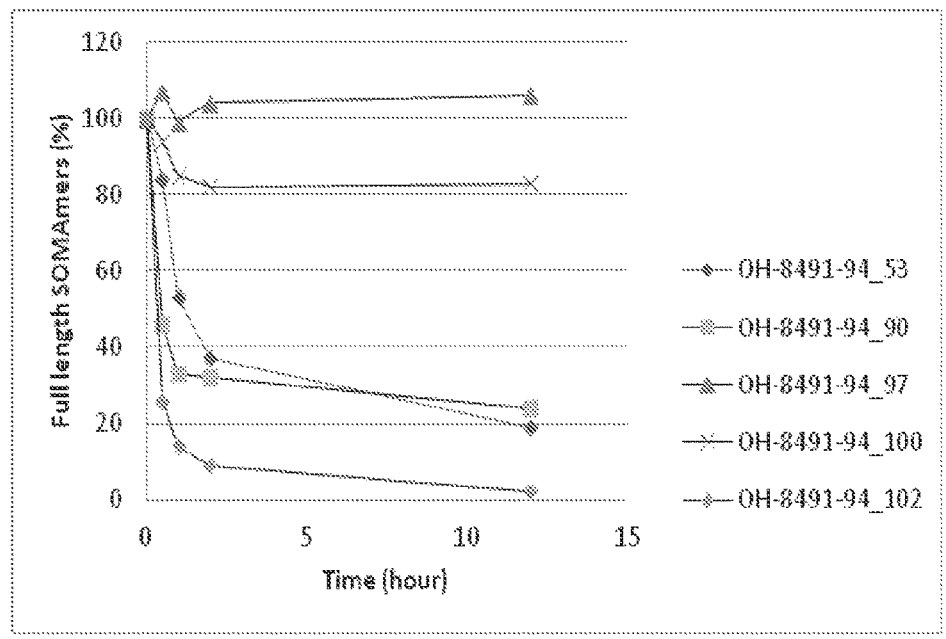
Figure 9:
FIG. 9 shows certain exemplary C-5 modified pyrimidine (or 5-dU modifications), as discussed in Example 15. Each modification structure is attached to dU as shown, e.g., in FIG. 10.
Figure 9:
Figure 9:
Figure 9:
Figure 9:
Figure 9:
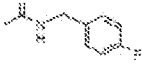
Figure 9:
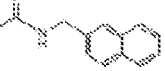
Figure 9:
Figure 9:
Figure 9:
Figure 9:
Figure 9:
Figure 9:
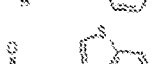
Figure 9:
Figure 9:
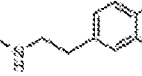
Figure 10:
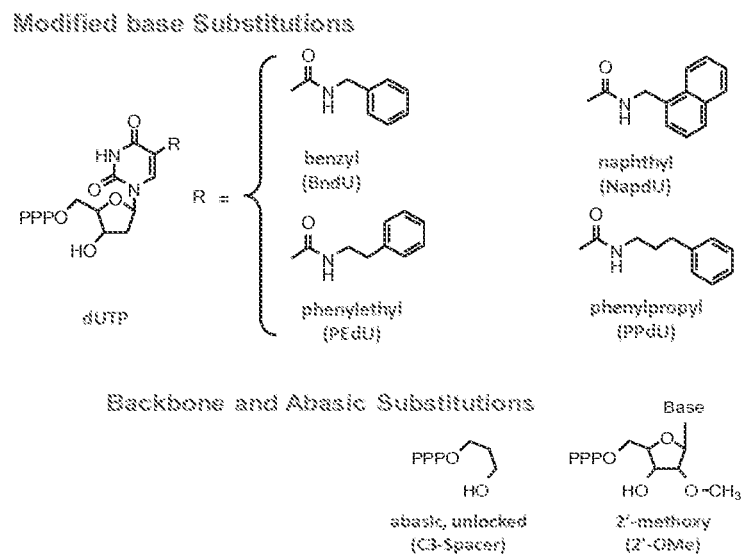
FIG. 10 shows certain C-5 pyrimidine and backbone modifications, as discussed in the Examples section.
Figure 11:
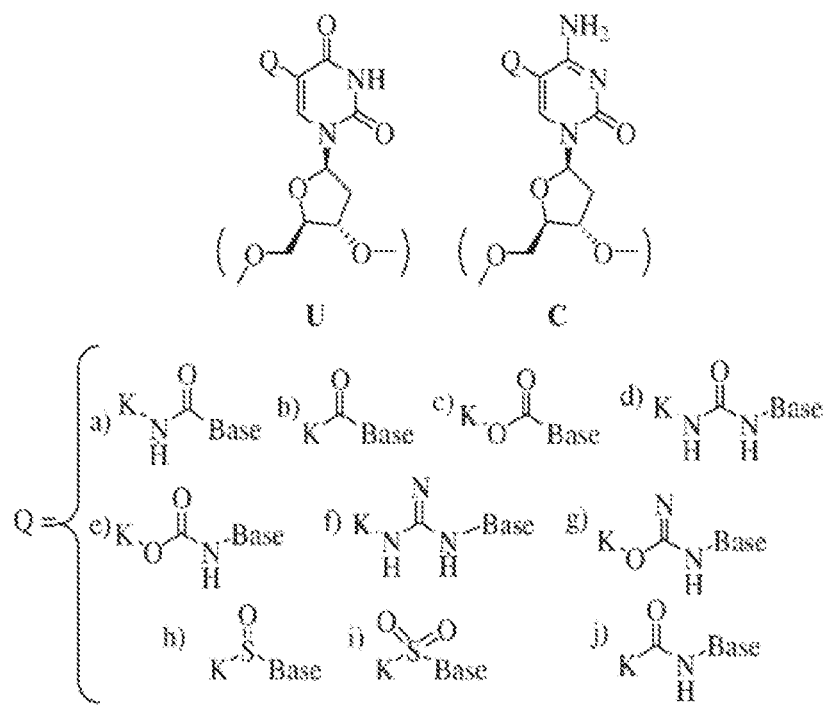
FIG. 11 shows certain exemplary modified pyrimidines (or C-5 modified pyrimidine) that may be incorporated into aptamers, such as slow off-rate aptamers.
Figure 11:
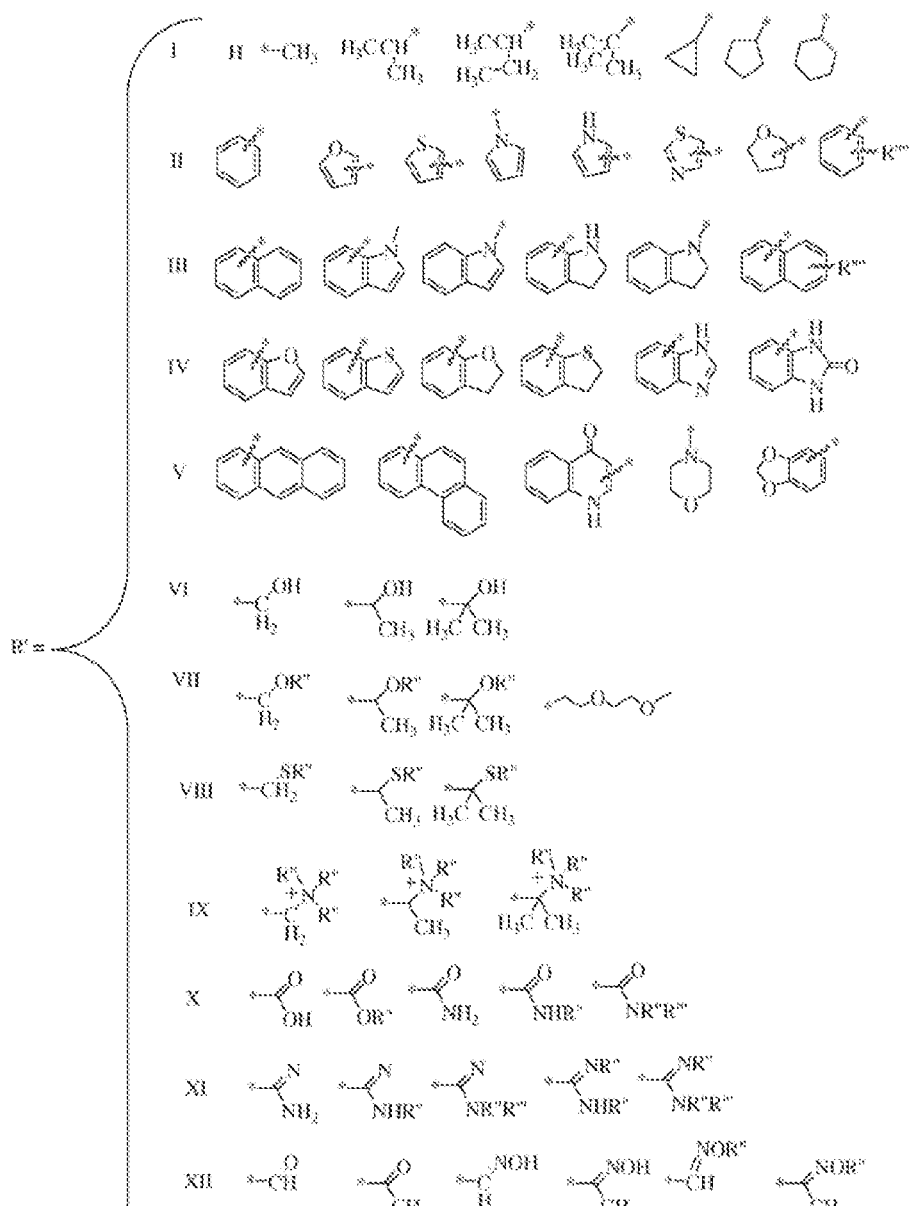

These assays were used to determine if the aptamers with multiple 2'-O-methyl substitutions had enhanced nuclease resistance compared to the aptamers 28-mer 8491-94_53 (SEQ ID NO: 58) which contains no 2'-O-methyl substitutions. The use of NapdU nucleotides, the 2'-OMe substitutions and the addition of an inverted deoxythymidine at the 3'-terminus in 8491-94_53 together may impart a substantial degree of nuclease protection compared with unmodified DNA. Nevertheless, 8491-94_53 is still not fully stable in the presence of nucleases. For example, 8491-94_53 (SEQ ID NO: 58) can be digested by human recombinant DNase I (FIG. 7) and porcine pancreatic DNase II (FIG. 8). As shown in FIG. 7, a decrease in intensity of the full-length 8491-94_53 aptamer (upper band) by approximately 20% over 2 hours and a decrease in intensity by approximately 75% over 12 hours in FIG. 8 indicate sensitivity to digestion by DNase I and DNase II, respectively. Four aptamers with multiple 2'-OMe substitution were also tested for nuclease resistance. These were 8491-94_90 (10 2'-OMe substitutions), 8491-94_97 (17 2'-OMe substitutions), 8491-94_100 (15 2'-OMe substitutions and 3 C3-spacer substitutions) and 8491-94_102 (9 2'-OMe substitutions and 3 C3-spacer substitutions). Aptamers 8491-94_97 (SEQ ID NO: 125) and 8491-94_102 (SEQ ID NO: 130) showed enhanced stability to DNase I while aptamers 8491-94_90 (SEQ ID NO: 118) and 8491-94_100 (SEQ ID NO: 128) did not (FIG. 7). Aptamers 8491-94_97 (SEQ ID NO: 125) and 8491-94_100 (SEQ ID NO: 128) showed enhanced stability to DNase II while aptamers 8491-94_90 (SEQ ID NO: 118) and 8491-94_102 (SEQ ID NO: 130) did not (FIG. 8). Thus, aptamer 8491-94_97 (SEQ ID NO: 125) was one of the four aptamers tested with multiple nuclease stabilizing substitutions that showed enhanced stability against both DNase I and DNase II.

The invention claimed is:

1. An aptamer that binds C3 protein, wherein the aptamer comprises a first region and a second region, wherein:
the first region comprises the sequence 5'-PAGPC-3' (SEQ ID NO: 132) and the second region comprises the sequence 5'-GPAYRPP-3' (SEQ ID NO: 157), wherein each P is independently, and for each occurrence, a C-5 modified pyrimidine nucleoside; Y is C, U, or T; and R is G or A, wherein each C-5 modified pyrimidine nucleoside is independently selected from: 5-(N-1-naphthylmethylcarboxyamide)-2'-deoxyuridine (NapdU), 5-(N-1-naphthylmethylcarboxyamide)-2'-O-methyluridine, 5-(N-1-naphthylmethylcarboxyamide)-2'-fluorouridine, 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine, and
wherein the 3'-end of the first region is covalently linked to the 5'-end of the second region by at least one linker.

2. The aptamer of claim 1, wherein the second region comprises the sequence 5'-GPACGPP-3' (SEQ ID NO: 133), wherein each P is independently, and for each occurrence, a C-5 modified pyrimidine nucleoside independently selected from: 5-(N-1-naphthylmethylcarboxyamide)-2'-deoxyuridine (NapdU), 5-(N-1-naphthylmethylcarboxyamide)-2'-O-methyluridine, 5-(N-1-naphthylmethylcarboxyamide)-2'-fluorouridine, 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine.

3. The aptamer of claim 1, wherein the aptamer comprises a sequence and features of a SEQ ID NO selected from SEQ ID NOs: 4 to 28, 32, 33, 39 to 69, 72, 73, 78 to 118, 121 to 130, and 139 to 151.

4. The aptamer of claim 1, wherein the aptamer is at least 80% identical to a sequence and features of a SEQ ID NO selected from SEQ ID NOs: 4 to 28, 32, 33, 39 to 69, 72, 73, 78 to 118, 121 to 130, and 139 to 151.

5. The aptamer of claim 1, wherein the at least one linker is selected from a nucleotide, a substituted or unsubstituted C2-C20 linker, an alkylene glycol, and a polyalkylene glycol.

6. The aptamer of claim 5, wherein the at least one linker is selected from a nucleotide, a 3-carbon spacer, and a hexaethylene glycol.

7. The aptamer of claim 1, wherein each C-5 modified pyrimidine nucleoside is independently selected from:
5-(N-1-naphthylmethylcarboxyamide)-2'-deoxyuridine (NapdU), 5-(N-1-naphthylmethylcarboxyamide)-2'-O-methyluridine, and 5-(N-1-naphthylmethylcarboxyamide)-2'-fluorouridine.

8. The aptamer of claim 1, wherein each C-5 modified pyrimidine nucleoside is 5-(N-naphthylmethylcarboxyamide)-2'-deoxyuridine (NapdU).

9. The aptamer of claim 1, wherein the aptamer comprises at least one 2'-O-methyl modified nucleotide.

10. The aptamer of claim 1, wherein the aptamer is 24 to 100 nucleotides in length.

11. The aptamer of claim 1, wherein the aptamer inhibits cleavage of C3 protein.

12. The aptamer of claim 1, wherein the C3 protein is human C3 protein.

13. A composition comprising the aptamer of claim 1 and a complement component 3 (C3) protein.

14. The aptamer of claim 2, wherein each C-5 modified pyrimidine nucleoside is 5-(N-naphthylmethylcarboxyamide)-2'-deoxyuridine (NapdU).

15. The aptamer of claim 5, wherein each C-5 modified pyrimidine nucleoside is 5-(N-naphthylmethylcarboxyamide)-2'-deoxyuridine (NapdU).

16. The aptamer of claim 6, wherein each C-5 modified pyrimidine nucleoside is 5-(N-naphthylmethylcarboxyamide)-2'-deoxyuridine (NapdU).

17. The aptamer of claim 8, wherein the aptamer is 24 to 100 nucleotides in length.

18. The aptamer of claim 17, wherein the aptamer inhibits cleavage of C3 protein.

19. The aptamer of claim 14, wherein the aptamer is 24 to 100 nucleotides in length.

20. The aptamer of claim 19, wherein the aptamer inhibits cleavage of C3 protein.

21. The aptamer of claim 15, wherein the aptamer is 24 to 100 nucleotides in length.

22. The aptamer of claim 21, wherein the aptamer inhibits cleavage of C3 protein.

23. The aptamer of claim 16, wherein the aptamer is 24 to 100 nucleotides in length.

24. The aptamer of claim 23, wherein the aptamer inhibits cleavage of C3 protein.

* * * * *

SEQUENCE LISTING

```
<160> NUMBER OF SEQ ID NOS: 157

<210> SEQ ID NO 1
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(2)
<223> OTHER INFORMATION: a-biotin
<220> FEATURE:
<221> NAME/KEY: Variation
<222> LOCATION: (29)..(68)
<223> OTHER INFORMATION: /replace="C" or "G" or "NapdU"
<220> FEATURE:
<221> NAME/KEY: misc_feature
<222> LOCATION: (1)..(86)
<223> OTHER INFORMATION: /note="Variant bases given in the sequence have
      no preference with respect to those in the annotations
      for variant positions"

<400> SEQUENCE: 1 aattttttttt gtgtctgtct gtgtcctcaa aaaaaaaaa aaaaaaaaaa aaaaaaaaa        60 aaaaaaaagg agtggtagag gactgg                                            86

<210> SEQ ID NO 2
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
atatatatcc agtcctctac cactcc                                            26

<210> SEQ ID NO 3
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (1)..(2)
<223> OTHER INFORMATION: a-biotin

<400> SEQUENCE: 3
``` aattttttttt gtgtctgtct gtgtcctc        28

```
<210> SEQ ID NO 4
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(7)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(28)
<223> OTHER INFORMATION: NapdU

<400> SEQUENCE: 4
```
gagcauugac ucaauagucc guacguuugg ccgggcaggg        40

```
<210> SEQ ID NO 5
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
```

```
<222> LOCATION: (24)..(25)
<223> OTHER INFORMATION: NapdU
<220> FEATURE:
<221> NAME/KEY: modified_base
<222> LOCATION: (31)..(31)
<223> OTHER INFORMATION: NapdU

<400> SEQUENCE: 5
ccggugacuc aauaguccgu acguucccgg uccgaacgcg                              40

<210> SEQ ID NO 6
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: NapdU
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (10)..(12)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (27)..(27)
<223> OTHER INFORMATION: NapdU
<220> FEATURE:
<221> NAME/KEY: modified_base
<222> LOCATION: (31)..(34)
<223> OTHER INFORMATION: NapdU
<220> FEATURE:
<221> NAME/KEY: modified_base
<222> LOCATION: (40)..(40)
<223> OTHER INFORMATION: NapdU

<400> SEQUENCE: 6
augucggcgu uuggcucaau aguccguacg uuuuacgcgu                              40

<210> SEQ ID NO 7
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
```

```
<221> NAME/KEY: modified_base
<222> LOCATION: (1)..(1)
<223> OTHER INFORMATION: NapdU
<220> FEATURE:
<221> NAME/KEY: modified_base
<222> LOCATION: (11)..(12)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (27)..(27)
<223> OTHER INFORMATION: NapdU
<220> FEATURE:
<221> NAME/KEY: modified_base
<222> LOCATION: (31)..(33)
<223> OTHER INFORMATION: NapdU
<220> FEATURE:
<221> NAME/KEY: modified_base
<222> LOCATION: (35)..(35)
<223> OTHER INFORMATION: NapdU
<220> FEATURE:
<221> NAME/KEY: modified_base
<222> LOCATION: (39)..(39)
<223> OTHER INFORMATION: NapdU

<400> SEQUENCE: 7
uacaaagcga uuggcucgau agucaguacg uuucucgcuc                                40

<210> SEQ ID NO 8
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (7)..(7)
<223> OTHER INFORMATION: NapdU
<220> FEATURE:
<221> NAME/KEY: modified_base
<222> LOCATION: (10)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
```

-continued

```
<222> LOCATION: (26)..(26)
<223> OTHER INFORMATION: NapdU
<220> FEATURE:
<221> NAME/KEY: modified_base
<222> LOCATION: (30)..(32)
<223> OTHER INFORMATION: NapdU
<220> FEATURE:
<221> NAME/KEY: modified_base
<222> LOCATION: (38)..(39)
<223> OTHER INFORMATION: NapdU

<400> SEQUENCE: 8
agacuguagu ugacuccaua guccguacgu uuacacauug                    40

<210> SEQ ID NO 9
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: NapdU
<220> FEATURE:
<221> NAME/KEY: modified_base
<222> LOCATION: (6)..(7)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(28)
<223> OTHER INFORMATION: NapdU
<220> FEATURE:
<221> NAME/KEY: modified_base
<222> LOCATION: (33)..(33)
<223> OTHER INFORMATION: NapdU

<400> SEQUENCE: 9
uacgguuggc uccauaguca guacguuuac gauacccc                      38

<210> SEQ ID NO 10
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
```

```
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(26)
<223> OTHER INFORMATION: NapdU

<400> SEQUENCE: 10
ccggugacuc aauaguccgu acguuuggcc gggcaggg                              38

<210> SEQ ID NO 11
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(3)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (14)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (26)..(26)
<223> OTHER INFORMATION: NapdU
<220> FEATURE:
<221> NAME/KEY: modified_base
<222> LOCATION: (30)..(30)
<223> OTHER INFORMATION: NapdU
<220> FEATURE:
<221> NAME/KEY: modified_base
<222> LOCATION: (34)..(36)
<223> OTHER INFORMATION: NapdU

<400> SEQUENCE: 11
cuuaaaaggg ucguugacuc cauaguccgu acguuuccga                            40
```

<210> SEQ ID NO 12
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"
<220> FEATURE:
<221> NAME/KEY: modified_base
<222> LOCATION: (2)..(2)
<223> OTHER INFORMATION: NapdU
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(25)
<223> OTHER INFORMATION: NapdU
<220> FEATURE:
<221> NAME/KEY: modified_base
<222> LOCATION: (28)..(28)
<223> OTHER INFORMATION: NapdU
<220> FEATURE:
<221> NAME/KEY: modified_base
<222> LOCATION: (34)..(34)
<223> OTHER INFORMATION: NapdU
<220> FEATURE:
<221> NAME/KEY: modified_base
<222> LOCATION: (37)..(38)
<223> OTHER INFORMATION: NapdU
<220> FEATURE:
<221> NAME/KEY: modified_base
<222> LOCATION: (40)..(40)
<223> OTHER INFORMATION: NapdU

<400> SEQUENCE: 12
gucuggcuaa cuuaguccgu acguucguga gcgugauuau      40

<210> SEQ ID NO 13
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"
<220> FEATURE:
<221> NAME/KEY: modified_base
<222> LOCATION: (1)..(1)
<223> OTHER INFORMATION: NapdU
<220> FEATURE:

```
<221> NAME/KEY: modified_base
<222> LOCATION: (3)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(26)
<223> OTHER INFORMATION: NapdU
<220> FEATURE:
<221> NAME/KEY: modified_base
<222> LOCATION: (34)..(34)
<223> OTHER INFORMATION: NapdU

<400> SEQUENCE: 13
uguugacuca cauaguccgu acguuuacgg caauagcaca                              40

<210> SEQ ID NO 14
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(7)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(28)
<223> OTHER INFORMATION: NapdU
<220> FEATURE:
<221> NAME/KEY: modified_base
<222> LOCATION: (35)..(36)
<223> OTHER INFORMATION: NapdU

<400> SEQUENCE: 14
gagcauugac ucaauagucc guacguuugg cccguucaca ag                          42
```

<210> SEQ ID NO 15
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"
<220> FEATURE:
<221> NAME/KEY: modified_base
<222> LOCATION: (6)..(7)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(27)
<223> OTHER INFORMATION: NapdU
<220> FEATURE:
<221> NAME/KEY: modified_base
<222> LOCATION: (33)..(33)
<223> OTHER INFORMATION: NapdU
<220> FEATURE:
<221> NAME/KEY: modified_base
<222> LOCATION: (35)..(35)
<223> OTHER INFORMATION: NapdU
<220> FEATURE:
<221> NAME/KEY: modified_base
<222> LOCATION: (41)..(41)
<223> OTHER INFORMATION: NapdU

<400> SEQUENCE: 15
gagcauugac ucaauagucc guacguuccc ggucugaacg ug                42

<210> SEQ ID NO 16
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"
<220> FEATURE:
<221> NAME/KEY: modified_base
<222> LOCATION: (2)..(2)
<223> OTHER INFORMATION: NapdU
<220> FEATURE:
<221> NAME/KEY: modified_base
<222> LOCATION: (15)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:

```
<221> NAME/KEY: modified_base
<222> LOCATION: (25)..(25)
<223> OTHER INFORMATION: NapdU
<220> FEATURE:
<221> NAME/KEY: modified_base
<222> LOCATION: (28)..(28)
<223> OTHER INFORMATION: NapdU
<220> FEATURE:
<221> NAME/KEY: modified_base
<222> LOCATION: (32)..(32)
<223> OTHER INFORMATION: NapdU
<220> FEATURE:
<221> NAME/KEY: modified_base
<222> LOCATION: (36)..(38)
<223> OTHER INFORMATION: NapdU

<400> SEQUENCE: 16
cuaacacggc cgaguugacu cccauagucc guacguuugc                              40

<210> SEQ ID NO 17
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: NapdU
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (10)..(12)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (27)..(27)
<223> OTHER INFORMATION: NapdU
<220> FEATURE:
<221> NAME/KEY: modified_base
<222> LOCATION: (31)..(33)
<223> OTHER INFORMATION: NapdU

<400> SEQUENCE: 17
augucggcgu uugacucaau aguccguacg uuuggccggg caggg                        45

<210> SEQ ID NO 18
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(25)
<223> OTHER INFORMATION: NapdU

<400> SEQUENCE: 18
acggugacuc cauaguccgu acguucccgc ggacgcacc                     39

<210> SEQ ID NO 19
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(7)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(32)
<223> OTHER INFORMATION: NapdU

<400> SEQUENCE: 19
gagcauugac ucaauagucc guacguuuuu uugggccggg ggggcag            47

<210> SEQ ID NO 20
<211> LENGTH: 44
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(7)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(30)
<223> OTHER INFORMATION: NapdU

<400> SEQUENCE: 20
gagcauugac ucaauagucc guacguuuuu gaccggggca gggg            44

<210> SEQ ID NO 21
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(7)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(29)
<223> OTHER INFORMATION: NapdU
<220> FEATURE:
<221> NAME/KEY: modified_base
<222> LOCATION: (35)..(35)
<223> OTHER INFORMATION: NapdU

<400> SEQUENCE: 21
gagcauugac ucaauagucc guacguuuua cgcgu                                  35

<210> SEQ ID NO 22
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: NapdU
<220> FEATURE:
<221> NAME/KEY: modified_base
<222> LOCATION: (15)..(17)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (28)..(28)
<223> OTHER INFORMATION: NapdU
<220> FEATURE:
<221> NAME/KEY: modified_base
<222> LOCATION: (32)..(32)
<223> OTHER INFORMATION: NapdU
<220> FEATURE:
<221> NAME/KEY: modified_base
<222> LOCATION: (36)..(39)
<223> OTHER INFORMATION: NapdU

<400> SEQUENCE: 22
ucccacacga cgaauuugac ucaauagucc guacguuuua                             40

<210> SEQ ID NO 23
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (7)..(7)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(15)
<223> OTHER INFORMATION: NapdU
<220> FEATURE:
<221> NAME/KEY: modified_base
<222> LOCATION: (19)..(19)

```
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (26)..(26)
<223> OTHER INFORMATION: NapdU
<220> FEATURE:
<221> NAME/KEY: modified_base
<222> LOCATION: (30)..(30)
<223> OTHER INFORMATION: NapdU
<220> FEATURE:
<221> NAME/KEY: modified_base
<222> LOCATION: (34)..(37)
<223> OTHER INFORMATION: NapdU

<400> SEQUENCE: 23
caagccucuc gguuuggcua aauaguccgu acguuucac                                  40

<210> SEQ ID NO 24
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(2)
<223> OTHER INFORMATION: NapdU
<220> FEATURE:
<221> NAME/KEY: modified_base
<222> LOCATION: (6)..(6)
<223> OTHER INFORMATION: NapdU
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (17)..(17)
<223> OTHER INFORMATION: NapdU
<220> FEATURE:
<221> NAME/KEY: modified_base
<222> LOCATION: (21)..(23)
<223> OTHER INFORMATION: NapdU
<220> FEATURE:
<221> NAME/KEY: modified_base
<222> LOCATION: (30)..(30)
<223> OTHER INFORMATION: NapdU
<220> FEATURE:
<221> NAME/KEY: modified_base
<222> LOCATION: (37)..(37)
<223> OTHER INFORMATION: NapdU

<400> SEQUENCE: 24
uugacucgau aguccguacg uuugcggaau accagcugac                                 40

<210> SEQ ID NO 25
<211> LENGTH: 47
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(19)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(26)
<223> OTHER INFORMATION: NapdU
<220> FEATURE:
<221> NAME/KEY: modified_base
<222> LOCATION: (30)..(35)
<223> OTHER INFORMATION: NapdU

<400> SEQUENCE: 25
gagcuuuuuu gacucaauua guccguacgu uuuuuggccg ggcaggg         47

<210> SEQ ID NO 26
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (7)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (27)..(29)
<223> OTHER INFORMATION: NapdU
<220> FEATURE:
<221> NAME/KEY: modified_base
<222> LOCATION: (31)..(31)
<223> OTHER INFORMATION: NapdU

<400> SEQUENCE: 26
agcaacuuga cucaauaguc cguacguuua ugcgagaaca                                    40

<210> SEQ ID NO 27
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: NapdU
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (14)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(26)
<223> OTHER INFORMATION: NapdU
<220> FEATURE:
<221> NAME/KEY: modified_base
<222> LOCATION: (30)..(31)
<223> OTHER INFORMATION: NapdU
<220> FEATURE:
<221> NAME/KEY: modified_base
<222> LOCATION: (39)..(39)
<223> OTHER INFORMATION: NapdU

<400> SEQUENCE: 27
cuaugagggc ugauucaaua gucaguacgu ucgccccauc                                    40

<210> SEQ ID NO 28
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: NapdU
<220> FEATURE:
<221> NAME/KEY: modified_base
<222> LOCATION: (5)..(7)
<223> OTHER INFORMATION: NapdU
<220> FEATURE:
<221> NAME/KEY: modified_base

```
<222> LOCATION: (11)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(29)
<223> OTHER INFORMATION: NapdU
<220> FEATURE:
<221> NAME/KEY: modified_base
<222> LOCATION: (39)..(39)
<223> OTHER INFORMATION: NapdU

<400> SEQUENCE: 28
ucccuuuggc ucgauagucg guacguuuug gggaggcgug                    40

<210> SEQ ID NO 29
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (7)..(8)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (17)..(17)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(25)
<223> OTHER INFORMATION: NapdU
<220> FEATURE:
<221> NAME/KEY: modified_base
<222> LOCATION: (29)..(31)
<223> OTHER INFORMATION: NapdU

<400> SEQUENCE: 29
gaguacuucg acucaauagu ccguuacguu uggccggcag gc                    42

<210> SEQ ID NO 30
<211> LENGTH: 39
<212> TYPE: DNA
<213> ORGANISM: Artificial Sequence
<220> FEATURE:
```

<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"
<220> FEATURE:
<221> NAME/KEY: modified_base
<222> LOCATION: (3)..(3)
<223> OTHER INFORMATION: NapdU
<220> FEATURE:
<221> NAME/KEY: modified_base
<222> LOCATION: (7)..(7)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(26)
<223> OTHER INFORMATION: NapdU
<220> FEATURE:
<221> NAME/KEY: modified_base
<222> LOCATION: (30)..(30)
<223> OTHER INFORMATION: NapdU

<400> SEQUENCE: 30
cgugacucga ugagucauag ucgguuccgu ccgaacgcg                      39

<210> SEQ ID NO 31

<400> SEQUENCE: 31

000

<210> SEQ ID NO 32
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"
<220> FEATURE:
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)

```
<223> OTHER INFORMATION: NapdU
<220> FEATURE:
<221> NAME/KEY: modified_base
<222> LOCATION: (29)..(30)
<223> OTHER INFORMATION: NapdU
<220> FEATURE:
<221> NAME/KEY: modified_base
<222> LOCATION: (36)..(36)
<223> OTHER INFORMATION: NapdU

<400> SEQUENCE: 32
actccccggt gacucaauag uccguacguu cccgguccga acgcggagga            50

<210> SEQ ID NO 33
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (29)..(30)
<223> OTHER INFORMATION: NapdU
<220> FEATURE:
<221> NAME/KEY: modified_base
<222> LOCATION: (36)..(36)
<223> OTHER INFORMATION: NapdU

<400> SEQUENCE: 33
actccccggu gactcaauag uccguacguu cccgguccga acgcggagga            50

<210> SEQ ID NO 34
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: modified_base
```

```
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (29)..(30)
<223> OTHER INFORMATION: NapdU
<220> FEATURE:
<221> NAME/KEY: modified_base
<222> LOCATION: (36)..(36)
<223> OTHER INFORMATION: NapdU

<400> SEQUENCE: 34
actccccggu gacucaatag uccguacguu cccgguccga acgcggagga          50

<210> SEQ ID NO 35
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (29)..(30)
<223> OTHER INFORMATION: NapdU
<220> FEATURE:
<221> NAME/KEY: modified_base
<222> LOCATION: (36)..(36)
<223> OTHER INFORMATION: NapdU

<400> SEQUENCE: 35
actccccggu gacucaauag tccguacguu cccgguccga acgcggagga          50

<210> SEQ ID NO 36
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
```

```
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (29)..(30)
<223> OTHER INFORMATION: NapdU
<220> FEATURE:
<221> NAME/KEY: modified_base
<222> LOCATION: (36)..(36)
<223> OTHER INFORMATION: NapdU

<400> SEQUENCE: 36
actccccggu gacucaauag uccgtacguu cccgguccga acgcggagga          50

<210> SEQ ID NO 37
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (30)..(30)
<223> OTHER INFORMATION: NapdU
<220> FEATURE:
<221> NAME/KEY: modified_base
<222> LOCATION: (36)..(36)
<223> OTHER INFORMATION: NapdU

<400> SEQUENCE: 37
actccccggu gacucaauag uccguacgtu cccgguccga acgcggagga          50

<210> SEQ ID NO 38
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (29)..(29)
<223> OTHER INFORMATION: NapdU
<220> FEATURE:
<221> NAME/KEY: modified_base
<222> LOCATION: (36)..(36)
<223> OTHER INFORMATION: NapdU

<400> SEQUENCE: 38
actccccggu gacucaauag uccguacgut cccgguccga acgcggagga                  50

<210> SEQ ID NO 39
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (29)..(30)
<223> OTHER INFORMATION: NapdU

<400> SEQUENCE: 39
actccccggu gacucaauag uccguacguu cccggtccga acgcggagga                  50
```

<210> SEQ ID NO 40
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (29)..(30)
<223> OTHER INFORMATION: NapdU
<220> FEATURE:
<221> NAME/KEY: modified_base
<222> LOCATION: (36)..(36)
<223> OTHER INFORMATION: NapdU

<400> SEQUENCE: 40
actccccggu gacucaauag uccguacguu cccgguccga acgcgga        47

<210> SEQ ID NO 41
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU

```
<220> FEATURE:
<221> NAME/KEY: modified_base
<222> LOCATION: (29)..(30)
<223> OTHER INFORMATION: NapdU
<220> FEATURE:
<221> NAME/KEY: modified_base
<222> LOCATION: (36)..(36)
<223> OTHER INFORMATION: NapdU

<400> SEQUENCE: 41
actccccggu gacucaauag uccguacguu cccgguccga acgc      44

<210> SEQ ID NO 42
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (29)..(30)
<223> OTHER INFORMATION: NapdU
<220> FEATURE:
<221> NAME/KEY: modified_base
<222> LOCATION: (36)..(36)
<223> OTHER INFORMATION: NapdU

<400> SEQUENCE: 42
actccccggu gacucaauag uccguacguu cccgguccga a      41

<210> SEQ ID NO 43
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
```

```
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (29)..(30)
<223> OTHER INFORMATION: NapdU
<220> FEATURE:
<221> NAME/KEY: modified_base
<222> LOCATION: (36)..(36)
<223> OTHER INFORMATION: NapdU

<400> SEQUENCE: 43
actccccggu gacucaauag uccguacguu cccggucc                              38

<210> SEQ ID NO 44
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (7)..(7)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(27)
<223> OTHER INFORMATION: NapdU
<220> FEATURE:
<221> NAME/KEY: modified_base
<222> LOCATION: (33)..(33)
<223> OTHER INFORMATION: NapdU

<400> SEQUENCE: 44
ccccggugac ucaauagucc guacguuccc gguccgaacg cggagga                   47

<210> SEQ ID NO 45
<211> LENGTH: 44
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU
<220> FEATURE:
<221> NAME/KEY: modified_base
<222> LOCATION: (30)..(30)
<223> OTHER INFORMATION: NapdU

<400> SEQUENCE: 45
cggugacuca auaguccgua cguucccggu ccgaacgcgg agga                      44

<210> SEQ ID NO 46
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: NapdU
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(21)
<223> OTHER INFORMATION: NapdU
<220> FEATURE:
<221> NAME/KEY: modified_base
<222> LOCATION: (27)..(27)
```

<223> OTHER INFORMATION: NapdU

<400> SEQUENCE: 46
ugacucaaua guccguacgu ucccgguccg aacgcggagg a          41

<210> SEQ ID NO 47
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (29)..(30)
<223> OTHER INFORMATION: NapdU

<400> SEQUENCE: 47
actccccggu gacucaauag uccguacguu cccgg          35

<210> SEQ ID NO 48
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (29)..(30)
<223> OTHER INFORMATION: NapdU

<400> SEQUENCE: 48
actccccggu gacucaauag uccguacguu cc                                    32

<210> SEQ ID NO 49
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: modified_base
<222> LOCATION: (29)..(30)
<223> OTHER INFORMATION: NapdU

<400> SEQUENCE: 49
actccccggu gacucaauag uccguacguu                                       30

<210> SEQ ID NO 50
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(6)
<223> OTHER INFORMATION: NapdU
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:

```
<221> NAME/KEY: modified_base
<222> LOCATION: (17)..(17)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (25)..(26)
<223> OTHER INFORMATION: NapdU
<220> FEATURE:
<221> NAME/KEY: modified_base
<222> LOCATION: (32)..(32)
<223> OTHER INFORMATION: NapdU

<400> SEQUENCE: 50
cccggugacu caauaguccg uacguucccg guccgaacgc ggagga                 46

<210> SEQ ID NO 51
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(25)
<223> OTHER INFORMATION: NapdU
<220> FEATURE:
<221> NAME/KEY: modified_base
<222> LOCATION: (31)..(31)
<223> OTHER INFORMATION: NapdU

<400> SEQUENCE: 51
ccggugacuc aauaguccgu acguucccgg uccgaacgcg gagga                  45

<210> SEQ ID NO 52
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<220> FEATURE:
<221> NAME/KEY: modified_base
<222> LOCATION: (7)..(7)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(27)
<223> OTHER INFORMATION: NapdU
<220> FEATURE:
<221> NAME/KEY: modified_base
<222> LOCATION: (33)..(33)
<223> OTHER INFORMATION: NapdU

<400> SEQUENCE: 52
ccccggugac ucaauagucc guacguuccc ggucc                          35

<210> SEQ ID NO 53
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (7)..(7)
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (26)..(27)
<223> OTHER INFORMATION: NapdU

<400> SEQUENCE: 53
ccccggugac ucaauagucc guacguuccc gg                             32

<210> SEQ ID NO 54
<211> LENGTH: 30
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(25)
<223> OTHER INFORMATION: NapdU

<400> SEQUENCE: 54
ccggugacuc aauaguccgu acguucccgg                                          30

<210> SEQ ID NO 55
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(25)
<223> OTHER INFORMATION: NapdU

<400> SEQUENCE: 55
ccggugacuc aauaguccgu acguucccg                                           29
```

<210> SEQ ID NO 56
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(25)
<223> OTHER INFORMATION: NapdU

<400> SEQUENCE: 56
ccggugacuc aauaguccgu acguuccc                                28

<210> SEQ ID NO 57
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)

<223> OTHER INFORMATION: NapdU

<400> SEQUENCE: 57
cggugacuca auaguccgua cguucccgg                29

<210> SEQ ID NO 58
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 58
cggugacuca auaguccgua cguucccg                 28

<210> SEQ ID NO 59
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base -continued

```
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 59
cggugacuca auaguccgua cguuccg                                              27

<210> SEQ ID NO 60
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: misc_feature
<222> LOCATION: (1)..(1)
<223> OTHER INFORMATION: /note="N-term C3 linker"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 60
cggugacuca auaguccgua cguucccgg                                            29

<210> SEQ ID NO 61
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: misc_feature
<222> LOCATION: (1)..(2)
<223> OTHER INFORMATION: /note="C3 linker between nucleotides"
<220> FEATURE:
```

```
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 61
cggugacuca auaguccgua cguucccgg                                     29

<210> SEQ ID NO 62
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: misc_feature
<222> LOCATION: (2)..(3)
<223> OTHER INFORMATION: /note="C3 linker between nucleotides"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 62
```
ccgugacuca auaguccgua cguucccgg                                29

<210> SEQ ID NO 63
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: misc_feature
<222> LOCATION: (3)..(4)
<223> OTHER INFORMATION: /note="C3 linker between nucleotides"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 63
ccgugacuca auaguccgua cguucccgg                                29

<210> SEQ ID NO 64
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: misc_feature
<222> LOCATION: (5)..(6)
<223> OTHER INFORMATION: /note="C3 linker between nucleotides"
<220> FEATURE:
<221> NAME/KEY: modified_base
<222> LOCATION: (8)..(8)
<223> OTHER INFORMATION: NapdU
<220> FEATURE:

```
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 64
ccgguacuca auaguccgua cguucccgg                                      29

<210> SEQ ID NO 65
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: misc_feature
<222> LOCATION: (6)..(7)
<223> OTHER INFORMATION: /note="C3 linker between nucleotides"
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 65
ccggugcuca auaguccgua cguucccgg                                      29

<210> SEQ ID NO 66
<211> LENGTH: 29
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: misc_feature
<222> LOCATION: (7)..(8)
<223> OTHER INFORMATION: /note="C3 linker between nucleotides"
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 66
ccggugauca auaguccgua cguucccgg                                      29

<210> SEQ ID NO 67
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: misc_feature
<222> LOCATION: (9)..(10)
<223> OTHER INFORMATION: /note="C3 linker between nucleotides"
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
```

```
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 67
ccggugacua auaguccgua cguucccgg                                          29

<210> SEQ ID NO 68
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: misc_feature
<222> LOCATION: (10)..(11)
<223> OTHER INFORMATION: /note="C3 linker between nucleotides"
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 68
ccggugacuc auaguccgua cguucccgg                                          29

<210> SEQ ID NO 69
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

-continued

```
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: misc_feature
<222> LOCATION: (11)..(12)
<223> OTHER INFORMATION: /note="C3 linker between nucleotides"
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 69
ccggugacuc auaguccgua cguucccgg                                29

<210> SEQ ID NO 70
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: misc_feature
<222> LOCATION: (13)..(14)
<223> OTHER INFORMATION: /note="C3 linker between nucleotides"
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
```

```
<221> NAME/KEY: modified_base
<222> LOCATION: (24)..(24)
<223> OTHER INFORMATION: NapdU

<400> SEQUENCE: 70
ccggugacuc aauguccgua cguucccgg                                              29

<210> SEQ ID NO 71
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: misc_feature
<222> LOCATION: (14)..(15)
<223> OTHER INFORMATION: /note="C3 linker between nucleotides"
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 71
ccggugacuc aauauccgua cguucccgg                                              29

<210> SEQ ID NO 72
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
```

```
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: misc_feature
<222> LOCATION: (16)..(17)
<223> OTHER INFORMATION: /note="C3 linker between nucleotides"
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 72
ccggugacuc aauagucgua cguucccgg                                              29

<210> SEQ ID NO 73
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: misc_feature
<222> LOCATION: (17)..(18)
<223> OTHER INFORMATION: /note="C3 linker between nucleotides"
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 73
ccggugacuc aauagucgua cguucccgg                                              29
```

```
<210> SEQ ID NO 74
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: misc_feature
<222> LOCATION: (18)..(19)
<223> OTHER INFORMATION: /note="C3 linker between nucleotides"
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 74
ccggugacuc aauaguccua cguucccgg                                           29

<210> SEQ ID NO 75
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
```

```
<220> FEATURE:
<221> NAME/KEY: modified_base
<222> LOCATION: (20)..(20)
<223> OTHER INFORMATION: NapdU
<220> FEATURE:
<221> NAME/KEY: misc_feature
<222> LOCATION: (20)..(21)
<223> OTHER INFORMATION: /note="C3 linker between nucleotides"
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 75
ccggugacuc aauaguccgu cguucccgg                                              29

<210> SEQ ID NO 76
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: misc_feature
<222> LOCATION: (21)..(22)
<223> OTHER INFORMATION: /note="C3 linker between nucleotides"
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 76
ccggugacuc aauaguccgu aguucccgg                                              29

<210> SEQ ID NO 77
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
```

```
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: misc_feature
<222> LOCATION: (22)..(23)
<223> OTHER INFORMATION: /note="C3 linker between nucleotides"
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 77
ccggugacuc aauaguccgu acuucccgg                                    29

<210> SEQ ID NO 78
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(24)
<223> OTHER INFORMATION: NapdU
```

```
<220> FEATURE:
<221> NAME/KEY: modified_base
<222> LOCATION: (25)..(25)
<223> OTHER INFORMATION: NapdU
<220> FEATURE:
<221> NAME/KEY: misc_feature
<222> LOCATION: (25)..(26)
<223> OTHER INFORMATION: /note="C3 linker between nucleotides"

<400> SEQUENCE: 78
ccggugacuc aauaguccgu acguuccgg                                           29

<210> SEQ ID NO 79
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(24)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: misc_feature
<222> LOCATION: (26)..(27)
<223> OTHER INFORMATION: /note="C3 linker between nucleotides"

<400> SEQUENCE: 79
ccggugacuc aauaguccgu acguuccgg                                           29

<210> SEQ ID NO 80
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
```

```
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(24)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: misc_feature
<222> LOCATION: (27)..(28)
<223> OTHER INFORMATION: /note="C3 linker between nucleotides"

<400> SEQUENCE: 80
ccggugacuc aauaguccgu acguuccgg                                         29

<210> SEQ ID NO 81
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(24)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: misc_feature
<222> LOCATION: (28)..(29)
<223> OTHER INFORMATION: /note="C3 linker between nucleotides"
```

<400> SEQUENCE: 81
ccggugacuc aauaguccgu acguucccg                                29

<210> SEQ ID NO 82
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (5)..(5)
<223> OTHER INFORMATION: NapdU
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (24)..(24)
<223> OTHER INFORMATION: NapdU
<220> FEATURE:
<221> NAME/KEY: modified_base
<222> LOCATION: (25)..(25)
<223> OTHER INFORMATION: NapdU
<220> FEATURE:
<221> NAME/KEY: misc_feature
<222> LOCATION: (29)..(29)
<223> OTHER INFORMATION: /note="C-term C3 linker"

<400> SEQUENCE: 82
ccggugacuc aauaguccgu acguucccg                                29

<210> SEQ ID NO 83
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: misc_feature
<222> LOCATION: (6)..(7)
<223> OTHER INFORMATION: /note="C3 linker between nucleotides"
<220> FEATURE:
<221> NAME/KEY: modified_base
<222> LOCATION: (7)..(7)

```
<223> OTHER INFORMATION: NapdU
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (14)..(14)
<223> OTHER INFORMATION: NapdU
<220> FEATURE:
<221> NAME/KEY: misc_feature
<222> LOCATION: (15)..(16)
<223> OTHER INFORMATION: /note="C3 linker between nucleotides"
<220> FEATURE:
<221> NAME/KEY: modified_base
<222> LOCATION: (17)..(17)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: misc_feature
<222> LOCATION: (22)..(23)
<223> OTHER INFORMATION: /note="C3 linker between nucleotides"

<400> SEQUENCE: 83
cggugaucaa uagucguacg uuccg                                          25

<210> SEQ ID NO 84
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: misc_feature
<222> LOCATION: (6)..(7)
<223> OTHER INFORMATION: /note="C3 linker between nucleotides"
<220> FEATURE:
<221> NAME/KEY: modified_base
<222> LOCATION: (7)..(7)
<223> OTHER INFORMATION: NapdU
<220> FEATURE:
<221> NAME/KEY: misc_feature
<222> LOCATION: (7)..(8)
<223> OTHER INFORMATION: /note="C3 linker between nucleotides"
<220> FEATURE:
<221> NAME/KEY: modified_base
<222> LOCATION: (10)..(10)
<223> OTHER INFORMATION: NapdU
<220> FEATURE:
<221> NAME/KEY: modified_base
<222> LOCATION: (13)..(13)
<223> OTHER INFORMATION: NapdU
<220> FEATURE:
<221> NAME/KEY: misc_feature
<222> LOCATION: (14)..(15)
<223> OTHER INFORMATION: /note="C3 linker between nucleotides"
<220> FEATURE:
<221> NAME/KEY: modified_base
<222> LOCATION: (16)..(16)
<223> OTHER INFORMATION: NapdU
```

-continued

```
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: misc_feature
<222> LOCATION: (21)..(22)
<223> OTHER INFORMATION: /note="C3 linker between nucleotides"

<400> SEQUENCE: 84
cggugauaau agucguacgu uccg                                                24

<210> SEQ ID NO 85
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: misc_feature
<222> LOCATION: (16)..(17)
<223> OTHER INFORMATION: /note="C3 linker between nucleotides"
<220> FEATURE:
<221> NAME/KEY: modified_base
<222> LOCATION: (18)..(18)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: misc_feature
<222> LOCATION: (23)..(24)
<223> OTHER INFORMATION: /note="C3 linker between nucleotides"

<400> SEQUENCE: 85
cggugacuca auagucguac guuccg                                              26

<210> SEQ ID NO 86
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
```

```
        Synthetic oligonucleotide"
<220> FEATURE:
<221> NAME/KEY: source
<223> OTHER INFORMATION: /note="Description of Combined DNA/RNA
        Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: misc_feature
<222> LOCATION: (8)..(9)
<223> OTHER INFORMATION: /note="Heg linker between nucleotides"
<220> FEATURE:
<221> NAME/KEY: modified_base
<222> LOCATION: (9)..(9)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (16)..(16)
<223> OTHER INFORMATION: NapdU
<220> FEATURE:
<221> NAME/KEY: modified_base
<222> LOCATION: (20)..(20)
<223> OTHER INFORMATION: NapdU
<220> FEATURE:
<221> NAME/KEY: modified_base
<222> LOCATION: (21)..(21)
<223> OTHER INFORMATION: NapdU

<400> SEQUENCE: 86
cggugacuua guccguacgu ucccg                                          25

<210> SEQ ID NO 87
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"
<220> FEATURE:
<221> NAME/KEY: source
<223> OTHER INFORMATION: /note="Description of Combined DNA/RNA
        Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: misc_feature
<222> LOCATION: (16)..(17)
<223> OTHER INFORMATION: /note="C3 linker between nucleotides"
<220> FEATURE:
<221> NAME/KEY: modified_base
<222> LOCATION: (18)..(18)
<223> OTHER INFORMATION: NapdU
```

```
<220> FEATURE:
<221> NAME/KEY: modified_base
<222> LOCATION: (22)..(22)
<223> OTHER INFORMATION: NapdU
<220> FEATURE:
<221> NAME/KEY: modified_base
<222> LOCATION: (23)..(23)
<223> OTHER INFORMATION: NapdU

<400> SEQUENCE: 87
cggugacuca auagucguac guucccg                                              27

<210> SEQ ID NO 88
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 88
cggugacuca auaguccgua cguucccg                                             28

<210> SEQ ID NO 89
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (4)..(4)
```

```
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 89
cggugacuca auaguccgua cguucccg                                              28

<210> SEQ ID NO 90
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 90
cggugacuca auaguccgua cguucccg                                              28

<210> SEQ ID NO 91
<211> LENGTH: 28
<212> TYPE: DNA
<213> ORGANISM: Artificial Sequence
<220> FEATURE:
<221> NAME/KEY: source
```

<223> OTHER INFORMATION: /note="Description of Artificial Sequence:
       Synthetic oligonucleotide"
<220> FEATURE:
<221> NAME/KEY: source
<223> OTHER INFORMATION: /note="Description of Combined DNA/RNA
       Molecule: Synthetic oligonucleotide"
<220> FEATURE:
<221> NAME/KEY: modified_base
<222> LOCATION: (4)..(4)
<223> OTHER INFORMATION: 2'-O-methyl-NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 91
cggugacuca auaguccgua cguucccg                                        28

<210> SEQ ID NO 92
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: source
<223> OTHER INFORMATION: /note="Description of Combined DNA/RNA
       Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 92
cggugacuca auaguccgua cguucccg                28

<210> SEQ ID NO 93
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (6)..(6)
<223> OTHER INFORMATION: 2'-O-methyl-a
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 93
cggugacuca auaguccgua cguucccg                28

<210> SEQ ID NO 94
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base

```
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 94
cggugacuca auaguccgua cguucccg                                    28

<210> SEQ ID NO 95
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: 2'-O-methyl-NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 95
cggugacuca auaguccgua cguucccg                                    28

<210> SEQ ID NO 96
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
```

<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 96
cggugacuca auaguccgua cguucccg                                              28

<210> SEQ ID NO 97
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 97
cggugacuca auaguccgua cguucccg                                              28

<210> SEQ ID NO 98
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (11)..(11)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 98
cggugacuca auaguccgua cguucccg                                           28

<210> SEQ ID NO 99
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: 2'-O-methyl-NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 99
cggugacuca auaguccgua cguucccg                                           28
```

```
<210> SEQ ID NO 100
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 100
cggugacuca auaguccgua cguucccg                                            28

<210> SEQ ID NO 101
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (14)..(14)
<223> OTHER INFORMATION: 2'-O-methyl-g
<220> FEATURE:
<221> NAME/KEY: modified_base
<222> LOCATION: (15)..(15)
<223> OTHER INFORMATION: NapdU
```

```
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 101
cggugacuca auaguccgua cguucccg                                              28

<210> SEQ ID NO 102
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: 2'-O-methyl-NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 102
cggugacuca auaguccgua cguucccg                                              28

<210> SEQ ID NO 103
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
```

```
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (16)..(16)
<223> OTHER INFORMATION: 2'-O-methyl-c
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(24)
<223> OTHER INFORMATION: NapdU

<400> SEQUENCE: 103
cggugacuca auaguccgua cguucccg                                              28

<210> SEQ ID NO 104
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (17)..(17)
<223> OTHER INFORMATION: 2'-O-methyl-c
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 104
cggugacuca auaguccgua cguucccg                                              28

<210> SEQ ID NO 105
<211> LENGTH: 28
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (18)..(18)
<223> OTHER INFORMATION: 2'-O-methyl-g
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 105
cggugacuca auaguccgua cguucccg                                           28

<210> SEQ ID NO 106
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
```

```
<223> OTHER INFORMATION: 2'-O-methyl-NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 106
cggugacuca auaguccgua cguucccg                                          28

<210> SEQ ID NO 107
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (20)..(20)
<223> OTHER INFORMATION: 2'-O-methyl-a
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 107
cggugacuca auaguccgua cguucccg                                          28

<210> SEQ ID NO 108
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
```

```
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (21)..(21)
<223> OTHER INFORMATION: 2'-O-methyl-c
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU

<400> SEQUENCE: 108
cggugacuca auaguccgua cguucccg                                              28

<210> SEQ ID NO 109
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (22)..(22)
<223> OTHER INFORMATION: 2'-O-methyl-g
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
```

```
<223> OTHER INFORMATION: NapdU

<400> SEQUENCE: 109
cggugacuca auaguccgua cguucccg                                              28

<210> SEQ ID NO 110
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: NapdU

<400> SEQUENCE: 110
cggugacuca auaguccgua cguucccg                                              28

<210> SEQ ID NO 111
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
```

```
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: 2'-O-methyl-NapdU

<400> SEQUENCE: 111
cggugacuca auaguccgua cguucccg                                          28

<210> SEQ ID NO 112
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU
<220> FEATURE:
<221> NAME/KEY: modified_base
<222> LOCATION: (25)..(25)
<223> OTHER INFORMATION: 2'-O-methyl-c

<400> SEQUENCE: 112
cggugacuca auaguccgua cguucccg                                          28

<210> SEQ ID NO 113
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

-continued

```
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU
<220> FEATURE:
<221> NAME/KEY: modified_base
<222> LOCATION: (26)..(26)
<223> OTHER INFORMATION: 2'-O-methyl-c

<400> SEQUENCE: 113
cggugacuca auaguccgua cguucccg                                       28

<210> SEQ ID NO 114
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
```

```
<222> LOCATION: (24)..(24)
<223> OTHER INFORMATION: NapdU
<220> FEATURE:
<221> NAME/KEY: modified_base
<222> LOCATION: (27)..(27)
<223> OTHER INFORMATION: 2'-O-methyl-c

<400> SEQUENCE: 114
cggugacuca auaguccgua cguucccg                                      28

<210> SEQ ID NO 115
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU
<220> FEATURE:
<221> NAME/KEY: modified_base
<222> LOCATION: (28)..(28)
<223> OTHER INFORMATION: 2'-O-methyl-g

<400> SEQUENCE: 115
cggugacuca auaguccgua cguucccg                                      28

<210> SEQ ID NO 116
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
```

```
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU
<220> FEATURE:
<221> NAME/KEY: modified_base
<222> LOCATION: (28)..(28)
<223> OTHER INFORMATION: 2'-O-methyl-g

<400> SEQUENCE: 116
cggugacuca auaguccgua cguucccg                                          28

<210> SEQ ID NO 117
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
```

```
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU
<220> FEATURE:
<221> NAME/KEY: modified_base
<222> LOCATION: (28)..(28)
<223> OTHER INFORMATION: 2'-O-methyl-g

<400> SEQUENCE: 117
cggugacuca auaguccgua cguucccg                                            28

<210> SEQ ID NO 118
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
```

```
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-g

<400> SEQUENCE: 118
cggugacuca auaguccgua cguucccg                                          28

<210> SEQ ID NO 119
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
```

```
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (28)..(28)
<223> OTHER INFORMATION: 2'-O-methyl-g

<400> SEQUENCE: 119
cggugacuca auaguccgua cguucccg                                           28

<210> SEQ ID NO 120
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
```

<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-g

<400> SEQUENCE: 120
cggugacuca auaguccgua cguucccg                                           28

<210> SEQ ID NO 121
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base

```
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-g

<400> SEQUENCE: 121
cggugacuca auaguccgua cguucccg                                          28

<210> SEQ ID NO 122
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
```

<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-g

<400> SEQUENCE: 122
cggugacuca auaguccgua cguucccg				28

<210> SEQ ID NO 123
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (20)..(20)
<223> OTHER INFORMATION: 2'-O-methyl-a
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-g

<400> SEQUENCE: 123
```
cggugacuca auaguccgua cguucccg    28

<210> SEQ ID NO 124
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (20)..(20)
<223> OTHER INFORMATION: 2'-O-methyl-a
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU

```
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-g

<400> SEQUENCE: 124
cggugacuca auaguccgua cguucccg                                              28

<210> SEQ ID NO 125
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
```

```
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (20)..(20)
<223> OTHER INFORMATION: 2'-O-methyl-a
<220> FEATURE:
<221> NAME/KEY: modified_base
<222> LOCATION: (22)..(22)
<223> OTHER INFORMATION: 2'-O-methyl-g
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-g

<400> SEQUENCE: 125
cggugacuca auaguccgua cguucccg                                            28

<210> SEQ ID NO 126
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
```

<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: misc_feature
<222> LOCATION: (16)..(17)
<223> OTHER INFORMATION: /note="C3 linker between nucleotides"
<220> FEATURE:
<221> NAME/KEY: modified_base
<222> LOCATION: (18)..(18)
<223> OTHER INFORMATION: 2'-O-methyl-NapdU
<220> FEATURE:
<221> NAME/KEY: modified_base
<222> LOCATION: (19)..(19)
<223> OTHER INFORMATION: 2'-O-methyl-a
<220> FEATURE:
<221> NAME/KEY: modified_base
<222> LOCATION: (21)..(21)
<223> OTHER INFORMATION: 2'-O-methyl-g
<220> FEATURE:
<221> NAME/KEY: modified_base
<222> LOCATION: (22)..(22)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-c
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-g

<400> SEQUENCE: 126
cggugacuca auagucguac guucccg                                            27

<210> SEQ ID NO 127
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:

```
          Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: misc_feature
<222> LOCATION: (16)..(17)
<223> OTHER INFORMATION: /note="C3 linker between nucleotides"
<220> FEATURE:
<221> NAME/KEY: modified_base
<222> LOCATION: (18)..(18)
<223> OTHER INFORMATION: 2'-O-methyl-NapdU
<220> FEATURE:
<221> NAME/KEY: modified_base
<222> LOCATION: (19)..(19)
<223> OTHER INFORMATION: 2'-O-methyl-a
<220> FEATURE:
<221> NAME/KEY: modified_base
<222> LOCATION: (21)..(21)
<223> OTHER INFORMATION: 2'-O-methyl-g
<220> FEATURE:
<221> NAME/KEY: modified_base
<222> LOCATION: (22)..(22)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: misc_feature
```

```
<222> LOCATION: (23)..(24)
<223> OTHER INFORMATION: /note="C3 linker between nucleotides"
<220> FEATURE:
<221> NAME/KEY: modified_base
<222> LOCATION: (24)..(24)
<223> OTHER INFORMATION: 2'-O-methyl-c
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-g

<400> SEQUENCE: 127
cggugacuca auagucguac guuccg                                           26

<210> SEQ ID NO 128
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: misc_feature
<222> LOCATION: (6)..(7)
<223> OTHER INFORMATION: /note="C3 linker between nucleotides"
<220> FEATURE:
<221> NAME/KEY: modified_base
<222> LOCATION: (7)..(7)
<223> OTHER INFORMATION: NapdU
<220> FEATURE:
<221> NAME/KEY: modified_base
<222> LOCATION: (8)..(8)
<223> OTHER INFORMATION: 2'-O-methyl-c
<220> FEATURE:
<221> NAME/KEY: modified_base
<222> LOCATION: (9)..(9)
<223> OTHER INFORMATION: 2'-O-methyl-a
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (12)..(12)
<223> OTHER INFORMATION: 2'-O-methyl-a
<220> FEATURE:
<221> NAME/KEY: modified_base
<222> LOCATION: (14)..(14)
```

```
<223> OTHER INFORMATION: NapdU
<220> FEATURE:
<221> NAME/KEY: misc_feature
<222> LOCATION: (15)..(16)
<223> OTHER INFORMATION: /note="C3 linker between nucleotides"
<220> FEATURE:
<221> NAME/KEY: modified_base
<222> LOCATION: (17)..(17)
<223> OTHER INFORMATION: 2'-O-methyl-NapdU
<220> FEATURE:
<221> NAME/KEY: modified_base
<222> LOCATION: (18)..(18)
<223> OTHER INFORMATION: 2'-O-methyl-a
<220> FEATURE:
<221> NAME/KEY: modified_base
<222> LOCATION: (20)..(20)
<223> OTHER INFORMATION: 2'-O-methyl-g
<220> FEATURE:
<221> NAME/KEY: modified_base
<222> LOCATION: (21)..(21)
<223> OTHER INFORMATION: 2'-O-methyl-NapdU
<220> FEATURE:
<221> NAME/KEY: modified_base
<222> LOCATION: (22)..(22)
<223> OTHER INFORMATION: 2'-O-methyl-NapdU
<220> FEATURE:
<221> NAME/KEY: misc_feature
<222> LOCATION: (22)..(23)
<223> OTHER INFORMATION: /note="C3 linker between nucleotides"
<220> FEATURE:
<221> NAME/KEY: modified_base
<222> LOCATION: (23)..(23)
<223> OTHER INFORMATION: 2'-O-methyl-c
<220> FEATURE:
<221> NAME/KEY: modified_base
<222> LOCATION: (24)..(24)
<223> OTHER INFORMATION: 2'-O-methyl-c
<220> FEATURE:
<221> NAME/KEY: modified_base
<222> LOCATION: (25)..(25)
<223> OTHER INFORMATION: 2'-O-methyl-g

<400> SEQUENCE: 128
cggugaucaa uagucguacg uuccg                                        25

<210> SEQ ID NO 129
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
```

<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: NapdU
<220> FEATURE:
<221> NAME/KEY: modified_base
<222> LOCATION: (20)..(20)
<223> OTHER INFORMATION: 2'-O-methyl-a
<220> FEATURE:
<221> NAME/KEY: modified_base
<222> LOCATION: (22)..(22)
<223> OTHER INFORMATION: 2'-O-methyl-g
<220> FEATURE:
<221> NAME/KEY: modified_base
<222> LOCATION: (23)..(23)
<223> OTHER INFORMATION: NapdU
<220> FEATURE:
<221> NAME/KEY: modified_base
<222> LOCATION: (24)..(24)
<223> OTHER INFORMATION: NapdU
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-g

<400> SEQUENCE: 129
cggugacuca auaguccgua cguucccg                                          28

<210> SEQ ID NO 130
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:

-continued

```
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: misc_feature
<222> LOCATION: (6)..(7)
<223> OTHER INFORMATION: /note="C3 linker between nucleotides"
<220> FEATURE:
<221> NAME/KEY: modified_base
<222> LOCATION: (7)..(7)
<223> OTHER INFORMATION: NapdU
<220> FEATURE:
<221> NAME/KEY: modified_base
<222> LOCATION: (9)..(9)
<223> OTHER INFORMATION: 2'-O-methyl-a
<220> FEATURE:
<221> NAME/KEY: modified_base
<222> LOCATION: (11)..(11)
<223> OTHER INFORMATION: NapdU
<220> FEATURE:
<221> NAME/KEY: modified_base
<222> LOCATION: (12)..(12)
<223> OTHER INFORMATION: 2'-O-methyl-a
<220> FEATURE:
<221> NAME/KEY: modified_base
<222> LOCATION: (14)..(14)
<223> OTHER INFORMATION: NapdU
<220> FEATURE:
<221> NAME/KEY: misc_feature
<222> LOCATION: (15)..(16)
<223> OTHER INFORMATION: /note="C3 linker between nucleotides"
<220> FEATURE:
<221> NAME/KEY: modified_base
<222> LOCATION: (17)..(17)
<223> OTHER INFORMATION: NapdU
<220> FEATURE:
<221> NAME/KEY: modified_base
<222> LOCATION: (21)..(21)
<223> OTHER INFORMATION: NapdU
<220> FEATURE:
<221> NAME/KEY: modified_base
<222> LOCATION: (22)..(22)
<223> OTHER INFORMATION: NapdU
<220> FEATURE:
<221> NAME/KEY: misc_feature
<222> LOCATION: (22)..(23)
<223> OTHER INFORMATION: /note="C3 linker between nucleotides"
<220> FEATURE:
<221> NAME/KEY: modified_base
<222> LOCATION: (23)..(23)
<223> OTHER INFORMATION: 2'-O-methyl-c
<220> FEATURE:
<221> NAME/KEY: modified_base
<222> LOCATION: (24)..(24)
<223> OTHER INFORMATION: 2'-O-methyl-c
<220> FEATURE:
<221> NAME/KEY: modified_base
<222> LOCATION: (25)..(25)
<223> OTHER INFORMATION: 2'-O-methyl-g
```

-continued

```
<400> SEQUENCE: 130
cggugaucaa uagucguacg uuccg                                           25

<210> SEQ ID NO 131
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: Variation
<222> LOCATION: (1)..(1)
<223> OTHER INFORMATION: /replace="C-5 modified pyrimidine" or "U" or
      "T" or "G" or " "
<220> FEATURE:
<221> NAME/KEY: misc_feature
<222> LOCATION: (1)..(2)
<223> OTHER INFORMATION: /note="If the nucleotide at the first indicated
      position is absent there may be a 3-carbon spacer present at this
      position"
<220> FEATURE:
<221> NAME/KEY: modified_base
<222> LOCATION: (2)..(2)
<223> OTHER INFORMATION: Independently selected from any C-5 modified
      pyrimidine
<220> FEATURE:
<221> NAME/KEY: Variation
<222> LOCATION: (5)..(5)
<223> OTHER INFORMATION: /replace="U" or "T" or "C-5 modified
      pyrimidine" or " "
<220> FEATURE:
<221> NAME/KEY: misc_feature
<222> LOCATION: (5)..(6)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (6)..(6)
<223> OTHER INFORMATION: Independently selected from any C-5 modified
      pyrimidine
<220> FEATURE:
<221> NAME/KEY: Variation
<222> LOCATION: (7)..(7)
<223> OTHER INFORMATION: /replace="C" or " "
<220> FEATURE:
<221> NAME/KEY: misc_feature
<222> LOCATION: (7)..(8)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (8)..(8)
<223> OTHER INFORMATION: /replace="G" or "C" or " "
<220> FEATURE:
<221> NAME/KEY: misc_feature
<222> LOCATION: (8)..(9)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (9)..(9)
<223> OTHER INFORMATION: /replace="C" or " "
<220> FEATURE:
<221> NAME/KEY: misc_feature
<222> LOCATION: (9)..(10)
<223> OTHER INFORMATION: /note="If the nucleotide at the first indicated
      position is absent there may be a 3-carbon spacer present between
```

```
          bases"
<220> FEATURE:
<221> NAME/KEY: Variation
<222> LOCATION: (10)..(10)
<223> OTHER INFORMATION: /replace="U" or "T" or "C-5 modified
      pyrimidine"
<220> FEATURE:
<221> NAME/KEY: modified_base
<222> LOCATION: (11)..(11)
<223> OTHER INFORMATION: Independently selected from any C-5 modified
      pyrimidine
<220> FEATURE:
<221> NAME/KEY: Variation
<222> LOCATION: (13)..(13)
<223> OTHER INFORMATION: /replace=" "
<220> FEATURE:
<221> NAME/KEY: misc_feature
<222> LOCATION: (13)..(14)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (14)..(14)
<223> OTHER INFORMATION: Independently selected from any C-5 modified
      pyrimidine
<220> FEATURE:
<221> NAME/KEY: Variation
<222> LOCATION: (15)..(15)
<223> OTHER INFORMATION: /replace=" "
<220> FEATURE:
<221> NAME/KEY: misc_feature
<222> LOCATION: (15)..(16)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (16)..(16)
<223> OTHER INFORMATION: /replace="G" or "C" or " "
<220> FEATURE:
<221> NAME/KEY: misc_feature
<222> LOCATION: (16)..(17)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (18)..(18)
<223> OTHER INFORMATION: Independently selected from any C-5 modified
      pyrimidine
<220> FEATURE:
<221> NAME/KEY: modified_base
<222> LOCATION: (22)..(22)
<223> OTHER INFORMATION: Independently selected from any C-5 modified
      pyrimidine
<220> FEATURE:
<221> NAME/KEY: modified_base
<222> LOCATION: (23)..(23)
<223> OTHER INFORMATION: Independently selected from any C-5 modified
      pyrimidine
<220> FEATURE:
<221> NAME/KEY: misc_feature
<222> LOCATION: (1)..(23)
<223> OTHER INFORMATION: /note="Variant bases given in the sequence have
      no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 131
cngrcnaaaa nagncagnac gnn                                            23

<210> SEQ ID NO 132
<211> LENGTH: 5
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: Independently selected from any C-5 modified
      pyrimidine
<220> FEATURE:
<221> NAME/KEY: modified_base
<222> LOCATION: (4)..(4)
<223> OTHER INFORMATION: Independently selected from any C-5 modified
      pyrimidine
<220> FEATURE:
<221> NAME/KEY: source
<223> OTHER INFORMATION: /note="See specification as filed for detailed
      description of substitutions and preferred embodiments"

<400> SEQUENCE: 132 nagnc                                                                    5

<210> SEQ ID NO 133
<211> LENGTH: 7
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Independently selected from any C-5 modified
      pyrimidine
<220> FEATURE:
<221> NAME/KEY: modified_base
<222> LOCATION: (6)..(6)
<223> OTHER INFORMATION: Independently selected from any C-5 modified
      pyrimidine
<220> FEATURE:
<221> NAME/KEY: modified_base
<222> LOCATION: (7)..(7)
<223> OTHER INFORMATION: Independently selected from any C-5 modified
      pyrimidine
<220> FEATURE:
<221> NAME/KEY: source
<223> OTHER INFORMATION: /note="See specification as filed for detailed
      description of substitutions and preferred embodiments"

<400> SEQUENCE: 133 gnacgnn                                                                  7

<210> SEQ ID NO 134
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<220> FEATURE:
<221> NAME/KEY: modified_base
<222> LOCATION: (1)..(1)
<223> OTHER INFORMATION: Independently selected from any C-5 modified
      pyrimidine
<220> FEATURE:
<221> NAME/KEY: Variation
<222> LOCATION: (3)..(3)
<223> OTHER INFORMATION: /replace=" "
<220> FEATURE:
<221> NAME/KEY: misc_feature
<222> LOCATION: (3)..(4)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (4)..(4)
<223> OTHER INFORMATION: Independently selected from any C-5 modified
      pyrimidine
<220> FEATURE:
<221> NAME/KEY: Variation
<222> LOCATION: (5)..(5)
<223> OTHER INFORMATION: /replace=" "
<220> FEATURE:
<221> NAME/KEY: misc_feature
<222> LOCATION: (5)..(6)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (8)..(8)
<223> OTHER INFORMATION: Independently selected from any C-5 modified
      pyrimidine
<220> FEATURE:
<221> NAME/KEY: modified_base
<222> LOCATION: (12)..(12)
<223> OTHER INFORMATION: Independently selected from any C-5 modified
      pyrimidine
<220> FEATURE:
<221> NAME/KEY: modified_base
<222> LOCATION: (13)..(13)
<223> OTHER INFORMATION: Independently selected from any C-5 modified
      pyrimidine
<220> FEATURE:
<221> NAME/KEY: misc_feature
<222> LOCATION: (1)..(13)
<223> OTHER INFORMATION: /note="Variant bases given in the sequence have
      no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 134
nagncvgnac gnn                                                           13

<210> SEQ ID NO 135
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: Variation
<222> LOCATION: (1)..(1)
<223> OTHER INFORMATION: /replace="C-5 modified pyrimidine" or "U" or
      "T" or "G" or " "
<220> FEATURE:
```

```
<221> NAME/KEY: misc_feature
<222> LOCATION: (1)..(2)
<223> OTHER INFORMATION: /note="If the nucleotide at the first indicated
      position is absent there may be a 3-carbon spacer present at this
      position"
<220> FEATURE:
<221> NAME/KEY: modified_base
<222> LOCATION: (2)..(2)
<223> OTHER INFORMATION: Independently selected from any C-5 modified
      pyrimidine
<220> FEATURE:
<221> NAME/KEY: Variation
<222> LOCATION: (5)..(5)
<223> OTHER INFORMATION: /replace="U" or "T" or "C-5 modified
      pyrimidine" or " "
<220> FEATURE:
<221> NAME/KEY: misc_feature
<222> LOCATION: (5)..(6)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (6)..(6)
<223> OTHER INFORMATION: Independently selected from any C-5 modified
      pyrimidine
<220> FEATURE:
<221> NAME/KEY: Variation
<222> LOCATION: (7)..(7)
<223> OTHER INFORMATION: /replace="C" or " "
<220> FEATURE:
<221> NAME/KEY: misc_feature
<222> LOCATION: (7)..(8)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (8)..(8)
<223> OTHER INFORMATION: /replace="G" or "C" or " "
<220> FEATURE:
<221> NAME/KEY: misc_feature
<222> LOCATION: (8)..(9)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (9)..(9)
<223> OTHER INFORMATION: /replace="C" or " "
<220> FEATURE:
<221> NAME/KEY: misc_feature
<222> LOCATION: (9)..(10)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (10)..(10)
<223> OTHER INFORMATION: /replace="U" or "T" or "C-5 modified
      pyrimidine"
<220> FEATURE:
<221> NAME/KEY: modified_base
<222> LOCATION: (11)..(11)
<223> OTHER INFORMATION: Independently selected from any C-5 modified
      pyrimidine
<220> FEATURE:
<221> NAME/KEY: Variation
<222> LOCATION: (13)..(13)
<223> OTHER INFORMATION: /replace=" "
<220> FEATURE:
<221> NAME/KEY: misc_feature
<222> LOCATION: (13)..(14)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (14)..(14)
```

```
<223> OTHER INFORMATION: Independently selected from any C-5 modified
      pyrimidine
<220> FEATURE:
<221> NAME/KEY: Variation
<222> LOCATION: (15)..(15)
<223> OTHER INFORMATION: /replace=" "
<220> FEATURE:
<221> NAME/KEY: misc_feature
<222> LOCATION: (15)..(16)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (16)..(16)
<223> OTHER INFORMATION: /replace="G" or "C" or " "
<220> FEATURE:
<221> NAME/KEY: misc_feature
<222> LOCATION: (16)..(17)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (18)..(18)
<223> OTHER INFORMATION: Independently selected from any C-5 modified
      pyrimidine
<220> FEATURE:
<221> NAME/KEY: modified_base
<222> LOCATION: (22)..(22)
<223> OTHER INFORMATION: Independently selected from any C-5 modified
      pyrimidine
<220> FEATURE:
<221> NAME/KEY: modified_base
<222> LOCATION: (23)..(23)
<223> OTHER INFORMATION: Independently selected from any C-5 modified
      pyrimidine
<220> FEATURE:
<221> NAME/KEY: Variation
<222> LOCATION: (24)..(24)
<223> OTHER INFORMATION: /replace="U" or "T" or "C-5 modified
      pyrimidine" or " "
<220> FEATURE:
<221> NAME/KEY: misc_feature
<222> LOCATION: (24)..(24)
<223> OTHER INFORMATION: /note="If the nucleotide at the first indicated
      position is absent there may be a 3-carbon spacer present at this
      position"
<220> FEATURE:
<221> NAME/KEY: misc_feature
<222> LOCATION: (1)..(24)
<223> OTHER INFORMATION: /note="Variant bases given in the sequence have
      no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 135
cngrcnaaaa nagncagnac gnnc                                              24

<210> SEQ ID NO 136
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: Variation
<222> LOCATION: (1)..(1)
```

```
<223> OTHER INFORMATION: /replace="C-5 modified pyrimidine" or "U" or
      "T" or "G" or " "
<220> FEATURE:
<221> NAME/KEY: misc_feature
<222> LOCATION: (1)..(2)
<223> OTHER INFORMATION: /note="If the nucleotide at the first indicated
      position is absent there may be a 3-carbon spacer present at this
      position"
<220> FEATURE:
<221> NAME/KEY: modified_base
<222> LOCATION: (2)..(2)
<223> OTHER INFORMATION: Independently selected from any C-5 modified
      pyrimidine
<220> FEATURE:
<221> NAME/KEY: Variation
<222> LOCATION: (5)..(5)
<223> OTHER INFORMATION: /replace="U" or "T" or "C-5 modified
      pyrimidine" or " "
<220> FEATURE:
<221> NAME/KEY: misc_feature
<222> LOCATION: (5)..(6)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (6)..(6)
<223> OTHER INFORMATION: Independently selected from any C-5 modified
      pyrimidine
<220> FEATURE:
<221> NAME/KEY: misc_feature
<222> LOCATION: (6)..(7)
<223> OTHER INFORMATION: /note="Substituted or unsubstituted C2-C20
      linker, an alkylene glycol, and a polyalkylene glycol between
      nucleotides"
<220> FEATURE:
<221> NAME/KEY: modified_base
<222> LOCATION: (7)..(7)
<223> OTHER INFORMATION: Independently selected from any C-5 modified
      pyrimidine
<220> FEATURE:
<221> NAME/KEY: Variation
<222> LOCATION: (9)..(9)
<223> OTHER INFORMATION: /replace=" "
<220> FEATURE:
<221> NAME/KEY: misc_feature
<222> LOCATION: (9)..(10)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (10)..(10)
<223> OTHER INFORMATION: Independently selected from any C-5 modified
      pyrimidine
<220> FEATURE:
<221> NAME/KEY: Variation
<222> LOCATION: (11)..(11)
<223> OTHER INFORMATION: /replace=" "
<220> FEATURE:
<221> NAME/KEY: misc_feature
<222> LOCATION: (11)..(12)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (12)..(12)
<223> OTHER INFORMATION: /replace="G" or "C" or " "
<220> FEATURE:
<221> NAME/KEY: misc_feature
<222> LOCATION: (12)..(13)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (14)..(14)
<223> OTHER INFORMATION: Independently selected from any C-5 modified
```

```
             pyrimidine
<220> FEATURE:
<221> NAME/KEY: modified_base
<222> LOCATION: (18)..(18)
<223> OTHER INFORMATION: Independently selected from any C-5 modified
      pyrimidine
<220> FEATURE:
<221> NAME/KEY: modified_base
<222> LOCATION: (19)..(19)
<223> OTHER INFORMATION: Independently selected from any C-5 modified
      pyrimidine
<220> FEATURE:
<221> NAME/KEY: misc_feature
<222> LOCATION: (1)..(19)
<223> OTHER INFORMATION: /note="Variant bases given in the sequence have
      no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 136
cngrcnnagn cagnacgnn                                                  19

<210> SEQ ID NO 137
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: Variation
<222> LOCATION: (1)..(1)
<223> OTHER INFORMATION: /replace="C-5 modified pyrimidine" or "U" or
      "T" or "G" or " "
<220> FEATURE:
<221> NAME/KEY: misc_feature
<222> LOCATION: (1)..(2)
<223> OTHER INFORMATION: /note="If the nucleotide at the first indicated
      position is absent there may be a 3-carbon spacer present at this
      position"
<220> FEATURE:
<221> NAME/KEY: modified_base
<222> LOCATION: (2)..(2)
<223> OTHER INFORMATION: Independently selected from any C-5 modified
      pyrimidine
<220> FEATURE:
<221> NAME/KEY: Variation
<222> LOCATION: (5)..(5)
<223> OTHER INFORMATION: /replace="U" or "T" or "C-5 modified
      pyrimidine" or " "
<220> FEATURE:
<221> NAME/KEY: misc_feature
<222> LOCATION: (5)..(6)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (6)..(6)
<223> OTHER INFORMATION: Independently selected from any C-5 modified
      pyrimidine
<220> FEATURE:
<221> NAME/KEY: misc_feature
<222> LOCATION: (6)..(7)
<223> OTHER INFORMATION: /note="Substituted or unsubstituted C2-C20
      linker, an alkylene glycol, and a polyalkylene glycol between
      nucleotides"
<220> FEATURE:
<221> NAME/KEY: modified_base
```

```
<222> LOCATION: (7)..(7)
<223> OTHER INFORMATION: Independently selected from any C-5 modified
      pyrimidine
<220> FEATURE:
<221> NAME/KEY: Variation
<222> LOCATION: (9)..(9)
<223> OTHER INFORMATION: /replace=" "
<220> FEATURE:
<221> NAME/KEY: misc_feature
<222> LOCATION: (9)..(10)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (10)..(10)
<223> OTHER INFORMATION: Independently selected from any C-5 modified
      pyrimidine
<220> FEATURE:
<221> NAME/KEY: Variation
<222> LOCATION: (11)..(11)
<223> OTHER INFORMATION: /replace=" "
<220> FEATURE:
<221> NAME/KEY: misc_feature
<222> LOCATION: (11)..(12)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (12)..(12)
<223> OTHER INFORMATION: /replace="G" or "C" or " "
<220> FEATURE:
<221> NAME/KEY: misc_feature
<222> LOCATION: (12)..(13)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (14)..(14)
<223> OTHER INFORMATION: Independently selected from any C-5 modified
      pyrimidine
<220> FEATURE:
<221> NAME/KEY: modified_base
<222> LOCATION: (18)..(18)
<223> OTHER INFORMATION: Independently selected from any C-5 modified
      pyrimidine
<220> FEATURE:
<221> NAME/KEY: modified_base
<222> LOCATION: (19)..(19)
<223> OTHER INFORMATION: Independently selected from any C-5 modified
      pyrimidine
<220> FEATURE:
<221> NAME/KEY: Variation
<222> LOCATION: (20)..(20)
<223> OTHER INFORMATION: /replace="U" or "T" or "C-5 modified
      pyrimidine" or " "
<220> FEATURE:
<221> NAME/KEY: misc_feature
<222> LOCATION: (20)..(20)
<223> OTHER INFORMATION: /note="If the nucleotide at the first indicated
      position is absent there may be a 3-carbon spacer present at this
      position"
<220> FEATURE:
<221> NAME/KEY: misc_feature
<222> LOCATION: (1)..(20)
<223> OTHER INFORMATION: /note="Variant bases given in the sequence have
      no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 137
cngrcnnagn cagnacgnnc                                                20
```

<210> SEQ ID NO 138
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (20)..(20)
<223> OTHER INFORMATION: 2'-O-methyl-a
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base

```
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c

<400> SEQUENCE: 138
cagugacuca auaguccaua cauuccca                                              28

<210> SEQ ID NO 139
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-g
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (20)..(20)
```

```
<223> OTHER INFORMATION: 2'-O-methyl-a
<220> FEATURE:
<221> NAME/KEY: modified_base
<222> LOCATION: (22)..(22)
<223> OTHER INFORMATION: 2'-O-methyl-g
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-c

<400> SEQUENCE: 139
gggugacuca auaguccgua cguucccc                                          28

<210> SEQ ID NO 140
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
```

```
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (20)..(20)
<223> OTHER INFORMATION: 2'-O-methyl-a
<220> FEATURE:
<221> NAME/KEY: modified_base
<222> LOCATION: (22)..(22)
<223> OTHER INFORMATION: 2'-O-methyl-g
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-a

<400> SEQUENCE: 140
tggugacuca auaguccgua cguuccca                                              28

<210> SEQ ID NO 141
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
```

```
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: misc_feature
<222> LOCATION: (16)..(17)
<223> OTHER INFORMATION: /note="C3 linker between nucleotides"
<220> FEATURE:
<221> NAME/KEY: modified_base
<222> LOCATION: (18)..(18)
<223> OTHER INFORMATION: 2'-O-methyl-NapdU
<220> FEATURE:
<221> NAME/KEY: modified_base
<222> LOCATION: (19)..(19)
<223> OTHER INFORMATION: 2'-O-methyl-a
<220> FEATURE:
<221> NAME/KEY: modified_base
<222> LOCATION: (21)..(21)
<223> OTHER INFORMATION: 2'-O-methyl-g
<220> FEATURE:
<221> NAME/KEY: modified_base
<222> LOCATION: (22)..(22)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-c
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-a

<400> SEQUENCE: 141
tggugacuca auagucguac guuccca                                    27

<210> SEQ ID NO 142
<211> LENGTH: 28
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (20)..(20)
<223> OTHER INFORMATION: 2'-O-methyl-a
<220> FEATURE:
<221> NAME/KEY: modified_base
<222> LOCATION: (22)..(22)
<223> OTHER INFORMATION: 2'-O-methyl-g
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (25)..(25)
<223> OTHER INFORMATION: 2'-O-methyl-c
<220> FEATURE:
```

```
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-a

<400> SEQUENCE: 142
tggugacuca auaguccgua tguuccca                                          28

<210> SEQ ID NO 143
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: misc_feature
<222> LOCATION: (16)..(17)
<223> OTHER INFORMATION: /note="C3 linker between nucleotides"
<220> FEATURE:
<221> NAME/KEY: modified_base
```

```
<222> LOCATION: (18)..(18)
<223> OTHER INFORMATION: 2'-O-methyl-NapdU
<220> FEATURE:
<221> NAME/KEY: modified_base
<222> LOCATION: (19)..(19)
<223> OTHER INFORMATION: 2'-O-methyl-a
<220> FEATURE:
<221> NAME/KEY: modified_base
<222> LOCATION: (21)..(21)
<223> OTHER INFORMATION: 2'-O-methyl-g
<220> FEATURE:
<221> NAME/KEY: modified_base
<222> LOCATION: (22)..(22)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-c
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-a

<400> SEQUENCE: 143
tggugacuca auagucguat guuccca                                           27

<210> SEQ ID NO 144
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
```

```
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (20)..(20)
<223> OTHER INFORMATION: 2'-O-methyl-a
<220> FEATURE:
<221> NAME/KEY: modified_base
<222> LOCATION: (22)..(22)
<223> OTHER INFORMATION: 2'-O-methyl-g
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-g

<400> SEQUENCE: 144
cggugacuca auaguccgua tguucccg                                              28

<210> SEQ ID NO 145
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-c
```

```
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: misc_feature
<222> LOCATION: (16)..(17)
<223> OTHER INFORMATION: /note="C3 linker between nucleotides"
<220> FEATURE:
<221> NAME/KEY: modified_base
<222> LOCATION: (18)..(18)
<223> OTHER INFORMATION: 2'-O-methyl-NapdU
<220> FEATURE:
<221> NAME/KEY: modified_base
<222> LOCATION: (19)..(19)
<223> OTHER INFORMATION: 2'-O-methyl-a
<220> FEATURE:
<221> NAME/KEY: modified_base
<222> LOCATION: (21)..(21)
<223> OTHER INFORMATION: 2'-O-methyl-g
<220> FEATURE:
<221> NAME/KEY: modified_base
<222> LOCATION: (22)..(22)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-c
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
```

-continued

```
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-g

<400> SEQUENCE: 145
cggugacuca auagucguat guucccg                                        27

<210> SEQ ID NO 146
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-g
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: misc_feature
<222> LOCATION: (16)..(17)
<223> OTHER INFORMATION: /note="C3 linker between nucleotides"
<220> FEATURE:
<221> NAME/KEY: modified_base
<222> LOCATION: (18)..(18)
<223> OTHER INFORMATION: 2'-O-methyl-NapdU
```

```
<220> FEATURE:
<221> NAME/KEY: modified_base
<222> LOCATION: (19)..(19)
<223> OTHER INFORMATION: 2'-O-methyl-a
<220> FEATURE:
<221> NAME/KEY: modified_base
<222> LOCATION: (21)..(21)
<223> OTHER INFORMATION: 2'-O-methyl-g
<220> FEATURE:
<221> NAME/KEY: modified_base
<222> LOCATION: (22)..(22)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-c
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c

<400> SEQUENCE: 146
gggugacuca auagucguac guucccc                                           27

<210> SEQ ID NO 147
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-g
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
```

```
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (20)..(20)
<223> OTHER INFORMATION: 2'-O-methyl-a
<220> FEATURE:
<221> NAME/KEY: modified_base
<222> LOCATION: (22)..(22)
<223> OTHER INFORMATION: 2'-O-methyl-a
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
<223> OTHER INFORMATION: 2'-O-methyl-c

<400> SEQUENCE: 147
gggugacuca auaguccgua cauucccc                                           28

<210> SEQ ID NO 148
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-g
<220> FEATURE:
<221> NAME/KEY: modified_base
```

```
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: misc_feature
<222> LOCATION: (16)..(17)
<223> OTHER INFORMATION: /note="C3 linker between nucleotides"
<220> FEATURE:
<221> NAME/KEY: modified_base
<222> LOCATION: (18)..(18)
<223> OTHER INFORMATION: 2'-O-methyl-NapdU
<220> FEATURE:
<221> NAME/KEY: modified_base
<222> LOCATION: (19)..(19)
<223> OTHER INFORMATION: 2'-O-methyl-a
<220> FEATURE:
<221> NAME/KEY: modified_base
<222> LOCATION: (21)..(21)
<223> OTHER INFORMATION: 2'-O-methyl-a
<220> FEATURE:
<221> NAME/KEY: modified_base
<222> LOCATION: (22)..(22)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-c
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
```

<221> NAME/KEY: modified_base
<222> LOCATION: (27)..(27)
<223> OTHER INFORMATION: 2'-O-methyl-c

<400> SEQUENCE: 148
gggugacuca auagucguac auucccc                                    27

<210> SEQ ID NO 149
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-u
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: misc_feature
<222> LOCATION: (16)..(17)
<223> OTHER INFORMATION: /note="C3 linker between nucleotides"
<220> FEATURE:
<221> NAME/KEY: modified_base
<222> LOCATION: (18)..(18)
<223> OTHER INFORMATION: 2'-O-methyl-NapdU
<220> FEATURE:
<221> NAME/KEY: modified_base

```
<222> LOCATION: (19)..(19)
<223> OTHER INFORMATION: 2'-O-methyl-a
<220> FEATURE:
<221> NAME/KEY: modified_base
<222> LOCATION: (21)..(21)
<223> OTHER INFORMATION: 2'-O-methyl-g
<220> FEATURE:
<221> NAME/KEY: modified_base
<222> LOCATION: (22)..(22)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-c
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-a

<400> SEQUENCE: 149
uggugacuca auagucguac guuccca                                           27

<210> SEQ ID NO 150
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-u
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
```

```
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: misc_feature
<222> LOCATION: (16)..(17)
<223> OTHER INFORMATION: /note="C3 linker between nucleotides"
<220> FEATURE:
<221> NAME/KEY: modified_base
<222> LOCATION: (18)..(18)
<223> OTHER INFORMATION: 2'-O-methyl-NapdU
<220> FEATURE:
<221> NAME/KEY: modified_base
<222> LOCATION: (19)..(19)
<223> OTHER INFORMATION: 2'-O-methyl-a
<220> FEATURE:
<221> NAME/KEY: modified_base
<222> LOCATION: (21)..(21)
<223> OTHER INFORMATION: 2'-O-methyl-a
<220> FEATURE:
<221> NAME/KEY: modified_base
<222> LOCATION: (22)..(22)
<223> OTHER INFORMATION: 2'-O-methyl-NapdU
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-c
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-a

<400> SEQUENCE: 150
uggugacuca auagucguac auuccca                                        27

<210> SEQ ID NO 151
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'-O-methyl-u
```

```
<220> FEATURE:
<221> NAME/KEY: modified_base
<222> LOCATION: (2)..(2)
<223> OTHER INFORMATION: 2'-O-methyl-g
<220> FEATURE:
<221> NAME/KEY: modified_base
<222> LOCATION: (3)..(3)
<223> OTHER INFORMATION: 2'-O-methyl-g
<220> FEATURE:
<221> NAME/KEY: modified_base
<222> LOCATION: (4)..(4)
<223> OTHER INFORMATION: NapdU
<220> FEATURE:
<221> NAME/KEY: modified_base
<222> LOCATION: (5)..(5)
<223> OTHER INFORMATION: 2'-O-methyl-g
<220> FEATURE:
<221> NAME/KEY: modified_base
<222> LOCATION: (7)..(7)
<223> OTHER INFORMATION: 2'-O-methyl-c
<220> FEATURE:
<221> NAME/KEY: modified_base
<222> LOCATION: (8)..(8)
<223> OTHER INFORMATION: NapdU
<220> FEATURE:
<221> NAME/KEY: modified_base
<222> LOCATION: (9)..(9)
<223> OTHER INFORMATION: 2'-O-methyl-c
<220> FEATURE:
<221> NAME/KEY: modified_base
<222> LOCATION: (10)..(10)
<223> OTHER INFORMATION: 2'-O-methyl-a
<220> FEATURE:
<221> NAME/KEY: modified_base
<222> LOCATION: (12)..(12)
<223> OTHER INFORMATION: NapdU
<220> FEATURE:
<221> NAME/KEY: modified_base
<222> LOCATION: (13)..(13)
<223> OTHER INFORMATION: 2'-O-methyl-a
<220> FEATURE:
<221> NAME/KEY: modified_base
<222> LOCATION: (15)..(15)
<223> OTHER INFORMATION: NapdU
<220> FEATURE:
<221> NAME/KEY: modified_base
<222> LOCATION: (19)..(19)
<223> OTHER INFORMATION: 2'-O-methyl-NapdU
<220> FEATURE:
<221> NAME/KEY: modified_base
<222> LOCATION: (20)..(20)
<223> OTHER INFORMATION: 2'-O-methyl-a
<220> FEATURE:
<221> NAME/KEY: modified_base
<222> LOCATION: (22)..(22)
<223> OTHER INFORMATION: 2'-O-methyl-a
<220> FEATURE:
<221> NAME/KEY: modified_base
<222> LOCATION: (23)..(23)
<223> OTHER INFORMATION: 2'-O-methyl-NapdU
<220> FEATURE:
<221> NAME/KEY: modified_base
<222> LOCATION: (24)..(24)
<223> OTHER INFORMATION: 2'-O-methyl-NapdU
<220> FEATURE:
<221> NAME/KEY: modified_base
<222> LOCATION: (25)..(25)
<223> OTHER INFORMATION: 2'-O-methyl-c
<220> FEATURE:
<221> NAME/KEY: modified_base
<222> LOCATION: (26)..(26)
<223> OTHER INFORMATION: 2'-O-methyl-c
<220> FEATURE:
<221> NAME/KEY: modified_base
<222> LOCATION: (27)..(27)
<223> OTHER INFORMATION: 2'-O-methyl-c
<220> FEATURE:
<221> NAME/KEY: modified_base
<222> LOCATION: (28)..(28)
```

<223> OTHER INFORMATION: 2'-O-methyl-a

<400> SEQUENCE: 151
uggugacuca auaguccgua cauuccca        28

<210> SEQ ID NO 152
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: Variation
<222> LOCATION: (1)..(1)
<223> OTHER INFORMATION: /replace="C-5 modified pyrimidine" or "U" or
      "T" or "G" or " "
<220> FEATURE:
<221> NAME/KEY: misc_feature
<222> LOCATION: (1)..(2)
<223> OTHER INFORMATION: /note="If the nucleotide at the first indicated
      position is absent there may be a 3-carbon spacer present at this
      position"
<220> FEATURE:
<221> NAME/KEY: modified_base
<222> LOCATION: (2)..(2)
<223> OTHER INFORMATION: Independently selected from any C-5 modified
      pyrimidine
<220> FEATURE:
<221> NAME/KEY: Variation
<222> LOCATION: (5)..(5)
<223> OTHER INFORMATION: /replace="U" or "T" or "C-5 modified
      pyrimidine" or " "
<220> FEATURE:
<221> NAME/KEY: misc_feature
<222> LOCATION: (5)..(6)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (6)..(6)
<223> OTHER INFORMATION: Independently selected from any C-5 modified
      pyrimidine
<220> FEATURE:
<221> NAME/KEY: Variation
<222> LOCATION: (7)..(7)
<223> OTHER INFORMATION: /replace="C" or " "
<220> FEATURE:
<221> NAME/KEY: misc_feature
<222> LOCATION: (7)..(8)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (8)..(8)
<223> OTHER INFORMATION: /replace="G" or "C" or " "
<220> FEATURE:
<221> NAME/KEY: misc_feature
<222> LOCATION: (8)..(9)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (9)..(9)
<223> OTHER INFORMATION: /replace="C" or " "
<220> FEATURE:
<221> NAME/KEY: misc_feature
<222> LOCATION: (9)..(10)
<223> OTHER INFORMATION: /note="If the nucleotide at the first indicated position is absent there may be a 3-carbon spacer present between
bases"
<220> FEATURE:
<221> NAME/KEY: Variation
<222> LOCATION: (10)..(10)
<223> OTHER INFORMATION: /replace="U" or "T" or "C-5 modified
pyrimidine"
<220> FEATURE:
<221> NAME/KEY: modified_base
<222> LOCATION: (11)..(11)
<223> OTHER INFORMATION: Independently selected from any C-5 modified
pyrimidine
<220> FEATURE:
<221> NAME/KEY: Variation
<222> LOCATION: (13)..(13)
<223> OTHER INFORMATION: /replace=" "
<220> FEATURE:
<221> NAME/KEY: misc_feature
<222> LOCATION: (13)..(14)
<223> OTHER INFORMATION: /note="If the nucleotide at the first indicated
position is absent there may be a 3-carbon spacer present between
bases"
<220> FEATURE:
<221> NAME/KEY: modified_base
<222> LOCATION: (14)..(14)
<223> OTHER INFORMATION: Independently selected from any C-5 modified
pyrimidine
<220> FEATURE:
<221> NAME/KEY: Variation
<222> LOCATION: (15)..(15)
<223> OTHER INFORMATION: /replace=" "
<220> FEATURE:
<221> NAME/KEY: misc_feature
<222> LOCATION: (15)..(16)
<223> OTHER INFORMATION: /note="If the nucleotide at the first indicated
position is absent there may be a 3-carbon spacer present between
bases"
<220> FEATURE:
<221> NAME/KEY: Variation
<222> LOCATION: (16)..(16)
<223> OTHER INFORMATION: /replace="G" or "C" or " "
<220> FEATURE:
<221> NAME/KEY: misc_feature
<222> LOCATION: (16)..(17)
<223> OTHER INFORMATION: /note="If the nucleotide at the first indicated
position is absent there may be a 3-carbon spacer present between
bases"
<220> FEATURE:
<221> NAME/KEY: modified_base
<222> LOCATION: (18)..(18)
<223> OTHER INFORMATION: Independently selected from any C-5 modified
pyrimidine
<220> FEATURE:
<221> NAME/KEY: Variation
<222> LOCATION: (20)..(20)
<223> OTHER INFORMATION: /replace="U" or "T"
<220> FEATURE:
<221> NAME/KEY: modified_base
<222> LOCATION: (22)..(22)
<223> OTHER INFORMATION: Independently selected from any C-5 modified
pyrimidine
<220> FEATURE:
<221> NAME/KEY: modified_base
<222> LOCATION: (23)..(23)
<223> OTHER INFORMATION: Independently selected from any C-5 modified
pyrimidine
<220> FEATURE:
<221> NAME/KEY: misc_feature
<222> LOCATION: (1)..(23)
<223> OTHER INFORMATION: /note="Variant bases given in the sequence have
no preference with respect to those in the annotations
for variant positions"
<220> FEATURE:
<221> NAME/KEY: source
<223> OTHER INFORMATION: /note="See specification as filed for detailed
description of substitutions and preferred embodiments"

<400> SEQUENCE: 152
cngrcnaaaa nagncagnac rnn 23

```
<210> SEQ ID NO 153
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: Variation
<222> LOCATION: (1)..(1)
<223> OTHER INFORMATION: /replace="C-5 modified pyrimidine" or "U" or
      "T" or "G" or " "
<220> FEATURE:
<221> NAME/KEY: misc_feature
<222> LOCATION: (1)..(2)
<223> OTHER INFORMATION: /note="If the nucleotide at the first indicated
      position is absent there may be a 3-carbon spacer present at this
      position"
<220> FEATURE:
<221> NAME/KEY: modified_base
<222> LOCATION: (2)..(2)
<223> OTHER INFORMATION: Independently selected from any C-5 modified
      pyrimidine
<220> FEATURE:
<221> NAME/KEY: Variation
<222> LOCATION: (5)..(5)
<223> OTHER INFORMATION: /replace="U" or "T" or "C-5 modified
      pyrimidine" or " "
<220> FEATURE:
<221> NAME/KEY: misc_feature
<222> LOCATION: (5)..(6)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (6)..(6)
<223> OTHER INFORMATION: Independently selected from any C-5 modified
      pyrimidine
<220> FEATURE:
<221> NAME/KEY: Variation
<222> LOCATION: (7)..(7)
<223> OTHER INFORMATION: /replace="C" or " "
<220> FEATURE:
<221> NAME/KEY: misc_feature
<222> LOCATION: (7)..(8)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (8)..(8)
<223> OTHER INFORMATION: /replace="G" or "C" or " "
<220> FEATURE:
<221> NAME/KEY: misc_feature
<222> LOCATION: (8)..(9)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (9)..(9)
<223> OTHER INFORMATION: /replace="C" or " "
<220> FEATURE:
<221> NAME/KEY: misc_feature
<222> LOCATION: (9)..(10)
<223> OTHER INFORMATION: /note="If the nucleotide at the first indicated
      position is absent there may be a 3-carbon spacer present between
      bases"
<220> FEATURE:
<221> NAME/KEY: Variation
```

-continued

```
<222> LOCATION: (10)..(10)
<223> OTHER INFORMATION: /replace="U" or "T" or "C-5 modified
      pyrimidine"
<220> FEATURE:
<221> NAME/KEY: modified_base
<222> LOCATION: (11)..(11)
<223> OTHER INFORMATION: Independently selected from any C-5 modified
      pyrimidine
<220> FEATURE:
<221> NAME/KEY: Variation
<222> LOCATION: (13)..(13)
<223> OTHER INFORMATION: /replace=" "
<220> FEATURE:
<221> NAME/KEY: misc_feature
<222> LOCATION: (13)..(14)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (14)..(14)
<223> OTHER INFORMATION: Independently selected from any C-5 modified
      pyrimidine
<220> FEATURE:
<221> NAME/KEY: Variation
<222> LOCATION: (15)..(15)
<223> OTHER INFORMATION: /replace=" "
<220> FEATURE:
<221> NAME/KEY: misc_feature
<222> LOCATION: (15)..(16)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (16)..(16)
<223> OTHER INFORMATION: /replace="G" or "C" or " "
<220> FEATURE:
<221> NAME/KEY: misc_feature
<222> LOCATION: (16)..(17)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (18)..(18)
<223> OTHER INFORMATION: Independently selected from any C-5 modified
      pyrimidine
<220> FEATURE:
<221> NAME/KEY: Variation
<222> LOCATION: (20)..(20)
<223> OTHER INFORMATION: /replace="U" or "T"
<220> FEATURE:
<221> NAME/KEY: modified_base
<222> LOCATION: (22)..(22)
<223> OTHER INFORMATION: Independently selected from any C-5 modified
      pyrimidine
<220> FEATURE:
<221> NAME/KEY: modified_base
<222> LOCATION: (23)..(23)
<223> OTHER INFORMATION: Independently selected from any C-5 modified
      pyrimidine
<220> FEATURE:
<221> NAME/KEY: Variation
<222> LOCATION: (24)..(24)
<223> OTHER INFORMATION: /replace="U" or "T" or "C-5 modified
      pyrimidine" or " "
<220> FEATURE:
<221> NAME/KEY: misc_feature
<222> LOCATION: (24)..(24)
<223> OTHER INFORMATION: /note="If the nucleotide at the first indicated
      position is absent there may be a 3-carbon spacer present at this
      position"
<220> FEATURE:
<221> NAME/KEY: misc_feature
<222> LOCATION: (1)..(24)
<223> OTHER INFORMATION: /note="Variant bases given in the sequence have
      no preference with respect to those in the annotations
      for variant positions"
```

```
<220> FEATURE:
<221> NAME/KEY: source
<223> OTHER INFORMATION: /note="See specification as filed for detailed
      description of substitutions and preferred embodiments"

<400> SEQUENCE: 153
cngrcnaaaa nagncagnac rnnc                                              24

<210> SEQ ID NO 154
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: Variation
<222> LOCATION: (1)..(1)
<223> OTHER INFORMATION: /replace="C-5 modified pyrimidine" or "U" or
      "T" or "G" or " "
<220> FEATURE:
<221> NAME/KEY: misc_feature
<222> LOCATION: (1)..(2)
<223> OTHER INFORMATION: /note="If the nucleotide at the first indicated
      position is absent there may be a 3-carbon spacer present at this
      position"
<220> FEATURE:
<221> NAME/KEY: modified_base
<222> LOCATION: (2)..(2)
<223> OTHER INFORMATION: Independently selected from any C-5 modified
      pyrimidine
<220> FEATURE:
<221> NAME/KEY: Variation
<222> LOCATION: (5)..(5)
<223> OTHER INFORMATION: /replace="U" or "T" or "C-5 modified
      pyrimidine" or " "
<220> FEATURE:
<221> NAME/KEY: misc_feature
<222> LOCATION: (5)..(6)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (6)..(6)
<223> OTHER INFORMATION: Independently selected from any C-5 modified
      pyrimidine
<220> FEATURE:
<221> NAME/KEY: misc_feature
<222> LOCATION: (6)..(7)
<223> OTHER INFORMATION: /note="Substituted or unsubstituted C2-C20
      linker, an alkylene glycol, and a polyalkylene glycol between
      nucleotides"
<220> FEATURE:
<221> NAME/KEY: modified_base
<222> LOCATION: (7)..(7)
<223> OTHER INFORMATION: Independently selected from any C-5 modified
      pyrimidine
<220> FEATURE:
<221> NAME/KEY: Variation
<222> LOCATION: (9)..(9)
<223> OTHER INFORMATION: /replace=" "
<220> FEATURE:
<221> NAME/KEY: misc_feature
<222> LOCATION: (9)..(10)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (10)..(10)
<223> OTHER INFORMATION: Independently selected from any C-5 modified
```

```
          pyrimidine
<220> FEATURE:
<221> NAME/KEY: Variation
<222> LOCATION: (11)..(11)
<223> OTHER INFORMATION: /replace=" "
<220> FEATURE:
<221> NAME/KEY: misc_feature
<222> LOCATION: (11)..(12)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (12)..(12)
<223> OTHER INFORMATION: /replace="G" or "C" or " "
<220> FEATURE:
<221> NAME/KEY: misc_feature
<222> LOCATION: (12)..(13)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (14)..(14)
<223> OTHER INFORMATION: Independently selected from any C-5 modified
      pyrimidine
<220> FEATURE:
<221> NAME/KEY: Variation
<222> LOCATION: (16)..(16)
<223> OTHER INFORMATION: /replace="U" or "T"
<220> FEATURE:
<221> NAME/KEY: modified_base
<222> LOCATION: (18)..(18)
<223> OTHER INFORMATION: Independently selected from any C-5 modified
      pyrimidine
<220> FEATURE:
<221> NAME/KEY: modified_base
<222> LOCATION: (19)..(19)
<223> OTHER INFORMATION: Independently selected from any C-5 modified
      pyrimidine
<220> FEATURE:
<221> NAME/KEY: misc_feature
<222> LOCATION: (1)..(19)
<223> OTHER INFORMATION: /note="Variant bases given in the sequence have
      no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 154
cngrcnnagn cagnacrnn                                                    19

<210> SEQ ID NO 155
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: Variation
<222> LOCATION: (1)..(1)
<223> OTHER INFORMATION: /replace="C-5 modified pyrimidine" or "U" or
      "T" or "G" or " "
<220> FEATURE:
<221> NAME/KEY: misc_feature
<222> LOCATION: (1)..(2)
<223> OTHER INFORMATION: /note="If the nucleotide at the first indicated
      position is absent there may be a 3-carbon spacer present at this
      position"
```

```
-continued

<220> FEATURE:
<221> NAME/KEY: modified_base
<222> LOCATION: (2)..(2)
<223> OTHER INFORMATION: Independently selected from any C-5 modified
      pyrimidine
<220> FEATURE:
<221> NAME/KEY: Variation
<222> LOCATION: (5)..(5)
<223> OTHER INFORMATION: /replace="U" or "T" or "C-5 modified
      pyrimidine" or " "
<220> FEATURE:
<221> NAME/KEY: misc_feature
<222> LOCATION: (5)..(6)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (6)..(6)
<223> OTHER INFORMATION: Independently selected from any C-5 modified
      pyrimidine
<220> FEATURE:
<221> NAME/KEY: misc_feature
<222> LOCATION: (6)..(7)
<223> OTHER INFORMATION: /note="Substituted or unsubstituted C2-C20
      linker, an alkylene glycol, and a polyalkylene glycol between
      nucleotides"
<220> FEATURE:
<221> NAME/KEY: modified_base
<222> LOCATION: (7)..(7)
<223> OTHER INFORMATION: Independently selected from any C-5 modified
      pyrimidine
<220> FEATURE:
<221> NAME/KEY: Variation
<222> LOCATION: (9)..(9)
<223> OTHER INFORMATION: /replace=" "
<220> FEATURE:
<221> NAME/KEY: misc_feature
<222> LOCATION: (9)..(10)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (10)..(10)
<223> OTHER INFORMATION: Independently selected from any C-5 modified
      pyrimidine
<220> FEATURE:
<221> NAME/KEY: Variation
<222> LOCATION: (11)..(11)
<223> OTHER INFORMATION: /replace=" "
<220> FEATURE:
<221> NAME/KEY: misc_feature
<222> LOCATION: (11)..(12)
<223> OTHER INFORMATION: /note="If the nucleotide at the first indicated
      position is absent there may be a 3-carbon spacer present between
      bases"
<220> FEATURE:
<221> NAME/KEY: Variation
<222> LOCATION: (12)..(12)
<223> OTHER INFORMATION: /replace="G" or "C" or " "
<220> FEATURE:
<221> NAME/KEY: misc_feature
<222> LOCATION: (12)..(13)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (14)..(14)
<223> OTHER INFORMATION: Independently selected from any C-5 modified
      pyrimidine
<220> FEATURE:
<221> NAME/KEY: Variation
<222> LOCATION: (16)..(16)
<223> OTHER INFORMATION: /replace="U" or "T"
<220> FEATURE:
<221> NAME/KEY: modified_base
<222> LOCATION: (18)..(18)
```

```
<223> OTHER INFORMATION: Independently selected from any C-5 modified
      pyrimidine
<220> FEATURE:
<221> NAME/KEY: modified_base
<222> LOCATION: (19)..(19)
<223> OTHER INFORMATION: Independently selected from any C-5 modified
      pyrimidine
<220> FEATURE:
<221> NAME/KEY: Variation
<222> LOCATION: (20)..(20)
<223> OTHER INFORMATION: /replace="U" or "T" or "C-5 modified
      pyrimidine" or " "
<220> FEATURE:
<221> NAME/KEY: misc_feature
<222> LOCATION: (20)..(20)
<223> OTHER INFORMATION: /note="If the nucleotide at the first indicated
      position is absent there may be a 3-carbon spacer present at this
      position"
<220> FEATURE:
<221> NAME/KEY: misc_feature
<222> LOCATION: (1)..(20)
<223> OTHER INFORMATION: /note="Variant bases given in the sequence have
      no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 155
cngrcnnagn cagnacrnnc                                             20

<210> SEQ ID NO 156
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: Independently selected from any C-5 modified
      pyrimidine
<220> FEATURE:
<221> NAME/KEY: Variation
<222> LOCATION: (3)..(3)
<223> OTHER INFORMATION: /replace=" "
<220> FEATURE:
<221> NAME/KEY: misc_feature
<222> LOCATION: (3)..(4)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (4)..(4)
<223> OTHER INFORMATION: Independently selected from any C-5 modified
      pyrimidine
<220> FEATURE:
<221> NAME/KEY: Variation
<222> LOCATION: (5)..(5)
<223> OTHER INFORMATION: /replace=" "
<220> FEATURE:
<221> NAME/KEY: misc_feature
<222> LOCATION: (5)..(6)
<223> OTHER INFORMATION: /note="If the nucleotide at the first indicated
      position is absent there may be a 3-carbon spacer present between
      bases"
<220> FEATURE:
<221> NAME/KEY: modified_base
<222> LOCATION: (8)..(8)
```

-continued

```
<223> OTHER INFORMATION: Independently selected from any C-5 modified
      pyrimidine
<220> FEATURE:
<221> NAME/KEY: Variation
<222> LOCATION: (10)..(10)
<223> OTHER INFORMATION: /replace="U" or "T"
<220> FEATURE:
<221> NAME/KEY: modified_base
<222> LOCATION: (12)..(12)
<223> OTHER INFORMATION: Independently selected from any C-5 modified
      pyrimidine
<220> FEATURE:
<221> NAME/KEY: modified_base
<222> LOCATION: (13)..(13)
<223> OTHER INFORMATION: Independently selected from any C-5 modified
      pyrimidine
<220> FEATURE:
<221> NAME/KEY: misc_feature
<222> LOCATION: (1)..(13)
<223> OTHER INFORMATION: /note="Variant bases given in the sequence have
      no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 156
nagncvgnac rnn                                                         13

<210> SEQ ID NO 157
<211> LENGTH: 7
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (2)..(2)
<223> OTHER INFORMATION: Independently selected from any C-5 modified
      pyrimidine
<220> FEATURE:
<221> NAME/KEY: Variation
<222> LOCATION: (4)..(4)
<223> OTHER INFORMATION: /replace="U" or "T"
<220> FEATURE:
<221> NAME/KEY: modified_base
<222> LOCATION: (6)..(6)
<223> OTHER INFORMATION: Independently selected from any C-5 modified
      pyrimidine
<220> FEATURE:
<221> NAME/KEY: modified_base
<222> LOCATION: (7)..(7)
<223> OTHER INFORMATION: Independently selected from any C-5 modified
      pyrimidine
<220> FEATURE:
<221> NAME/KEY: misc_feature
<222> LOCATION: (1)..(7)
<223> OTHER INFORMATION: /note="Variant bases given in the sequence have
      no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 157 gnacrnn                                                                 7
```